(12) United States Patent
Peters et al.

(10) Patent No.: US 9,050,343 B2
(45) Date of Patent: Jun. 9, 2015

(54) COMBINATION OF PIMAVANSERIN AND RISPERIDONE FOR THE TREATMENT OF PSYCHOSIS

(71) Applicants: Perry Peters, San Diego, CA (US); David Furlano, San Diego, CA (US); Daun Bahr, San Diego, CA (US); Daniel Van Kammen, San Diego, CA (US)

(72) Inventors: Perry Peters, San Diego, CA (US); David Furlano, San Diego, CA (US); Daun Bahr, San Diego, CA (US); Daniel Van Kammen, San Diego, CA (US); Mark Brann, Rye, NH (US)

(73) Assignee: ACADIA Pharmaceuticals Inc., San Diego, CA (US)

( * ) Notice: Subject to any disclaimer, the term of this patent is extended or adjusted under 35 U.S.C. 154(b) by 89 days.

(21) Appl. No.: 13/754,769

(22) Filed: Jan. 30, 2013

(65) Prior Publication Data
US 2013/0143901 A1 Jun. 6, 2013

Related U.S. Application Data

(62) Division of application No. 12/051,807, filed on Mar. 19, 2008, now abandoned.

(60) Provisional application No. 60/895,735, filed on Mar. 19, 2007, provisional application No. 60/908,921, filed on Mar. 29, 2007, provisional application No. 61/012,771, filed on Dec. 10, 2007, provisional application No. 61/026,092, filed on Feb. 4, 2008.

(51) Int. Cl.
| A61K 31/519 | (2006.01) |
| A61K 31/4468 | (2006.01) |
| A61K 31/45 | (2006.01) |
| A61K 31/00 | (2006.01) |
| A61K 31/4515 | (2006.01) |
| A61K 31/5513 | (2006.01) |
| A61K 31/554 | (2006.01) |

(52) U.S. Cl.
CPC .............. *A61K 31/519* (2013.01); *A61K 31/00* (2013.01); *A61K 31/4468* (2013.01); *A61K 31/4515* (2013.01); *A61K 31/5513* (2013.01); *A61K 31/554* (2013.01)

(58) Field of Classification Search
None
See application file for complete search history.

(56) References Cited

U.S. PATENT DOCUMENTS

| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,853,394 A | 8/1989 | King et al. |
| 5,025,013 A | 6/1991 | Barreau et al. |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda et al. |
| 5,707,798 A | 1/1998 | Brann |
| 5,795,894 A | 8/1998 | Shue et al. |
| 5,837,730 A | 11/1998 | Javitt |
| 5,869,488 A | 2/1999 | Shue et al. |
| 5,877,173 A | 3/1999 | Olney et al. |
| 5,912,132 A | 6/1999 | Brann |
| 5,955,281 A | 9/1999 | Brann |
| 6,107,324 A | 8/2000 | Behan et al. |
| 6,140,509 A | 10/2000 | Behan et al. |
| 6,150,393 A | 11/2000 | Behan et al. |
| 6,358,698 B1 | 3/2002 | Weiner et al. |
| 6,479,480 B1 | 11/2002 | Moyes et al. |
| 6,486,153 B1 | 11/2002 | Castro Pineiro et al. |
| 6,670,137 B2 | 12/2003 | VanMechelen et al. |
| 6,756,393 B2 | 6/2004 | Andersson et al. |
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 7,115,634 B2 | 10/2006 | Thurieau et al. |
| 7,253,186 B2 | 8/2007 | Andersson et al. |
| 7,601,740 B2 | 10/2009 | Weiner et al. |

(Continued)

FOREIGN PATENT DOCUMENTS

| CA | 984843 | 3/1976 |
| EP | 0 005 318 | 11/1979 |

(Continued)

OTHER PUBLICATIONS

Poewe (Movement Disorders vol. 18, Suppl. 6, 2003, pp. S80-S87).*

(Continued)

*Primary Examiner* — David J Blanchard
*Assistant Examiner* — Garen Gotfredson
(74) *Attorney, Agent, or Firm* — Jones Day

(57) ABSTRACT

Combinations of 5-HT2A inverse agonists or antagonists such as pimavanserin with antipsychotics such as risperidone are shown to induce a rapid onset of antipsychotic action and increase the number of responders when compared to therapy with the antipsychotic alone. These effects can be achieved at a low dose of the antipsychotic, thereby reducing the incidence of side effects. The combinations are also effective at decreases the incidence of weight gain and increased glucose or prolactin levels caused by the antipsychotic.

6 Claims, 42 Drawing Sheets

(56) References Cited

U.S. PATENT DOCUMENTS

| | | |
|---|---|---|
| 7,659,285 B2 | 2/2010 | Weiner et al. |
| 7,732,462 B2 | 6/2010 | Weiner et al. |
| 7,994,193 B2 | 8/2011 | Weiner et al. |
| 8,227,487 B2 | 7/2012 | Weiner et al. |
| 8,377,959 B2 | 2/2013 | Weiner et al. |
| 2002/0156068 A1 | 10/2002 | Behan et al. |
| 2002/0165225 A1 | 11/2002 | Kankan et al. |
| 2004/0006081 A1 | 1/2004 | Burrows et al. |
| 2004/0106600 A1 | 6/2004 | Andersson et al. |
| 2004/0213816 A1 | 10/2004 | Weiner et al. |
| 2005/0014757 A1 | 1/2005 | Andersson et al. |
| 2005/0148018 A1 | 7/2005 | Weiner et al. |
| 2005/0244862 A1 | 11/2005 | Brann |
| 2005/0256108 A1 | 11/2005 | Schlienger |
| 2005/0261278 A1 | 11/2005 | Weiner et al. |
| 2005/0261340 A1 | 11/2005 | Weiner et al. |
| 2005/0288328 A1 | 12/2005 | Weiner et al. |
| 2006/0094758 A1 | 5/2006 | Andersson et al. |
| 2006/0106063 A1 | 5/2006 | Thhygesen et al. |
| 2006/0111399 A1 | 5/2006 | Thhygesen et al. |
| 2006/0194778 A1 | 8/2006 | Andersson et al. |
| 2006/0194834 A1 | 8/2006 | Andersson et al. |
| 2006/0199794 A1 | 9/2006 | Schlienger |
| 2006/0199818 A1 | 9/2006 | Andersson et al. |
| 2006/0199842 A1 | 9/2006 | Weiner et al. |
| 2006/0204486 A1 | 9/2006 | Pyke et al. |
| 2006/0205710 A1 | 9/2006 | Schlienger et al. |
| 2006/0205722 A1 | 9/2006 | Andersson et al. |
| 2006/0205780 A1 | 9/2006 | Thygesen et al. |
| 2006/0205781 A1 | 9/2006 | Thygesen et al. |
| 2006/0264465 A1 | 11/2006 | Weiner et al. |
| 2006/0264466 A1 | 11/2006 | Weiner et al. |
| 2006/0286610 A1 | 12/2006 | Brann |
| 2006/0292606 A1 | 12/2006 | Brann |
| 2009/0053329 A1 | 2/2009 | Peters et al. |

FOREIGN PATENT DOCUMENTS

| | | |
|---|---|---|
| EP | 0 061 333 | 9/1982 |
| EP | 0 379 441 | 7/1990 |
| EP | 0 548 015 | 6/1993 |
| EP | 0 260 070 | 8/1993 |
| EP | 0 625 507 | 11/1994 |
| FR | 2802206 | 6/2001 |
| HU | 157325 | 3/1998 |
| JP | 51052176 | 5/1976 |
| JP | 5208517 | 7/1977 |
| WO | WO 94/27967 | 12/1994 |
| WO | WO 97/08166 | 3/1997 |
| WO | WO 97/11940 | 4/1997 |
| WO | WO 97/38665 | 10/1997 |
| WO | WO 97/38984 | 10/1997 |
| WO | WO 98/11128 | 3/1998 |
| WO | WO 98/17646 | 4/1998 |
| WO | WO 98/44921 | 10/1998 |
| WO | WO 98/50534 | 11/1998 |
| WO | WO 99/52927 | 10/1999 |
| WO | WO 00/23076 | 4/2000 |
| WO | WO 00/56335 | 9/2000 |
| WO | WO 00/59497 | 10/2000 |
| WO | WO 00/69810 | 11/2000 |
| WO | WO 01/44191 | 6/2001 |
| WO | WO 01/66521 | 9/2001 |
| WO | WO 01/87839 | 11/2001 |
| WO | WO 02/24649 | 3/2002 |
| WO | WO 02/076464 | 10/2002 |
| WO | WO 02/079186 | 10/2002 |
| WO | WO 03/057698 | 7/2003 |
| WO | WO 03/062206 | 7/2003 |
| WO | WO 03/070246 | 8/2003 |
| WO | WO 03/086400 | 10/2003 |
| WO | WO 2004/000808 | 12/2003 |
| WO | WO 2004/064738 | 8/2004 |
| WO | WO 2004/064753 | 8/2004 |
| WO | WO 2005/053796 | 6/2005 |
| WO | WO 2005/063254 | 7/2005 |
| WO | WO 2005/112927 | 12/2005 |
| WO | WO 2005112927 A1 * | 12/2005 |
| WO | WO 2006/036874 | 4/2006 |
| WO | WO 2006/037043 | 4/2006 |
| WO | WO 2006/104826 | 10/2006 |
| WO | WO 2004/039322 | 5/2007 |
| WO | WO2007/133802 | 11/2007 |

OTHER PUBLICATIONS

Adam, et al. 1989. Effects of repeated ritanserin on middle-aged poor sleepers. *Psychopharmacology*, 99:219-221.

Adell, et al. 2005. Strategies for producing faster acting antidepressants. *Drug Discovery Today*, 10(8):578-585.

Akin, et al. 2004. Decreased serotonin $5\text{-HT}_{2A}$ receptor-stimulated phosphoinositide signaling in fibroblasts from melancholic depressed patients. *Neuropsychopharmacology*, 29:2081-2087.

Alvisi, N. 1892. Sulla formazione di derivati pirazolici dalle dicloridrine e dalla tribromidrina della glicerina ordinaria, *Gazz. Chem. Ital.* 22:158-168.

Antilla, et al. 2001. Copper-catalyzed coupling of arylboronic acids and amines. *Organic Letters*, 3(13):2077-2079.

Antilla, et al. 2002. The copper-catalyzed N-arylation of indoles. *J. Am. Chem. Soc.*, 124:11684-11688.

Antunes, et al., 2012. The novel object recognition memory: neurobiology, test procedure, and its modifications. *Cogn Process* 13:93-110.

Archibald, et al., 1974 "1,4-Bis-(2-indol-3-ylethyl)piperdines" *J. Medicinal Chemistry*, 17(7):745-747.

Archibald, et al., 1974 "Benzamidopiperdines. 2. Heterocyclic Compounds Related to Indoramin" *J. Medicinal Chemistry*, 17(7):736-739.

Archibald, et al., 1974 "Benzamidopiperdines. 3. Heterocyclic Compounds Related to Indoramin" *J. Medicinal Chemistry*, 17(7):739-744.

Artico, et al. 1992. Aromatic hydrazides as specific inhibitors of bovine serum amine oxidase. *Eur. J. Med. Chem.*, 27:219-228.

Bakshi, et al. 1994. Clozapine antagonizes phencyclidine-induced deficits in sensorimotor gating of the startle response. *The Journal of Pharmacology and Experimental Therapeutics*, 271 (2):787-794.

Barchas, J. 1973. *Serotonin and Behavior*. New York: Academic Press.

Barnes, et al. 1999. A review of central 5-HT receptors and their function. *Neuropharmacology*, 38:1083-1152.

Barr, et al. 1997. Agonist-independent activation of $G_z$ by the 5-hydroxytryptamine$_{1A}$ receptor coexpressed in *Spodoptera frugiperda* cells. *The Journal of Biological Chemistry*, 272(52):32979-32987.

Bassus, et al. 1974. Psychotropes potentiels. X. Synthese de butyrophenones a cycle piperidine-spiro-tetrahydrooxazinone douees d'activite neuroleptique. *Eur. J. Med. Chem.—Chimica Therapeutica*, 9(4):416-423.

Bennett, et al. 1993. Suppression of dyskinesias in advanced Parkinson's disease. II. Increasing daily clozapine doses suppress dyskinesias and improve parkinsonism symptoms. *Neurology*, 43:1551-1555.

Bhatia, et al. 1996. 5-Lipoxygenase inhibitors: Synthesis and structure-activity relationships of a series of 1-Aryl-2H,4H-tetrahydro-1 ,2,4-triazin-3-ones. *J. Med. Chem.*, 39:3938-3950.

Biagi, et al. 1988. 1,2,3-Triazoles: Structural changes on two effective inhibitors of the prostaglandin synthesis in vitro. *Farmaco Ed. Sci.*, 43:597-612.

Bibbiani, et al. 2001. Serotonin 5-HT1A agonist improves motor complications in rodent and primate parkinsonian models. *Neurology*, 57:1829-1834.

Birkmayer, et al. 1974. Nucleus ruber and L-Dopa psychosis: Biochemical post-mortem findings. *Journal of Neural Transmission*, 35:93-116.

Blakley, et al. 2001. Bidirectional changes in ethanol consumption in rats with site-specific antisense down-regulation of 5-hydroxytryptamine$_{2A}$ receptors in brain. *The Journal of Pharmacology and Experimental Therapeutics*, 299(1):277-289.

(56) References Cited

OTHER PUBLICATIONS

Blier, et al. 2001. Putative mechanisms of action of antidepressant drugs in affective and anxiety disorders and pain. *Journal of Psychiatry & Neuroscience*, 26(1):37-43.

Blier, et al. 2005. Potential mechanisms of action of atypical antipsychotic medications in treatment-resistant depression and anxiety. *J. Clin. Psychiatry*, 66(suppl 8):30-40.

Bond et al. 1995. Physiological effects of inverse agonists in transgenic mice with myocardial overexpression of the $\beta_2$-adrenoceptor. *Nature*, 374:272-276.

Borman et al., "5-HT$_{2B}$ receptors play a key role in mediating the excitatory effects of 5-HT in human colon in vitro," *Br. J. Pharmacol.*, vol. 135, No. 5, pp. 1144-1151 (2002).

Boullin D. J. 1978. *Serotonin in Mental Abnormalities* (p. 316). New York: Wiley.

Brann, M. R. 1998. Identification of ligands by selective amplification of cells transfected with receptors and marker enzymes. *Chemical Abstracts*, 128:111548.

Brown, et al. 1924. Catalytic alkylation of aniline, *J. Am. Chem. Soc.*, 46(8):1836-1839.

Buchi et al. 1969. Synthesis of (±)-nuciferal. *J. Org. Chem.*, 34(4):1122-1123.

Butcher, et al. 1970. L-Dopa induced changes in central monoamine neurons after peripheral decarboxylase inhibition. *Letters to the Editor, J. Pharm. Pharmac.*, 22:313-316.

Buu-Hoi, et al. 1951. Further studies in the alkylation of phenols and thiophenols, *J. Org. Chem.*, 16:988-994.

Cacchi, et al. 2003. Palladium-catalyzed reaction of aryl iodides with acetic anhydride. A carbon monoxide-free synthesis of acetophenones. *Organic Letters*, 5(3):289-291.

Carman, et al. 1998. A further synthesis of an analogue of the antifungal/antiherbivore lipid from avocado. *Aust. J. Chem.*, 51:955-959.

Caroon, et al. 1981. Synthesis and antihypertensive activity of a series of 8-substituted 1-Oxa-3,8-diazaspiro[4.5]decan-2-ones. *J. Med. Chem.*, 24:1320-1328.

Carroll, et al. 1992. Synthesis and muscarinic receptor activity of ester derivatives of 2-substituted 2-azabicyclo[2.2.1]heptan-5-ol and -6-ol. *J. Med. Chem.*, 35:2184-2191.

Catarzi, et al. 2001. Synthesis, ionotropic glutamate receptor binding affinity, and structure-activity relationships of a new set of 4,5-dihydro-8-heteroaryl-4-Oxo-1,2,4-triazolo[1,5-alquinoxaline-2-carboxylates analogues of TQX-173. *J. Med Chem.*, 44:3157-3165.

Cerione, et al. 1984. The mammalian 2-adrenergic receptor: Reconsitution of functional interactions between pure receptor and pure stimlatory nucleotide binding protein of the adenylate cyclase system. *Biochemistry*, 23:4519-4525.

Chemical Abstracts, 73:25305. Benke, et al. 1970.

Cherkasov, et al. 1985. Organothiophosphorus reagents in organic synthesis. *Tetrahedron*, 41(13):2567-2624.

Choi et al., "5HT2B receptor-mediated serotonin morphogenic functions in mouse cranial neural crest and myocardiac cells," *Development*, vol. 124, pp. 1745-1755, (1997).

Clark et al. 1983. Antihypertensive 9-substituted 1-Oxa-4,9-diazaspiro[5.5]undecan-3-ones. *J. Med. Chem.*, 26:855-861.

Clifton, et al. 1982. Arylethanolamines Derived from Salicylamide with α- and β-Adrenoceptor Blocking Activities. Preparation of Labetalol, its Enantiomers, and Related Salicyclamides. *J. Med. Chem.*, 25:670-679.

Cox, R., "Medicinal Chemistry—28$^{th}$ International Symposium: Jun. 8-12, 2002, San Diego, CA, USA," *IDrugs*, vol. 5, No. 7, pp. 626-632 (2002).

DeClerck, et al. 1987. Increase in slow-wave sleep in humans with the serotonin-S$_2$ antagonist ritanserin. *Current Therapeutic Research*, 41(4):427-432.

Delecluse, et al. 1998. A case of tardive tremor successfully treated with clozapine. *Movement Disorders*, 13(5):846-847.

Dunn, et al. 1986. Analgetic and antiinflammatory 7-aroylbenzofuran-5-ylacetic acids and 7-aroylbenzothiophene-5-ylacetic acids. *J. Med. Chem.*, 29:2326-2329.

Durif, et al. 1997. Low-dose clozapine improves dyskinesias in Parkinson's disease. *Neurology*, 48:658-662.

Eichelbaum, et al. 1996. Influence of pharmacogenetics on drug disposition and response. *Clinical and Experimental Pharmacology and Physiology*, 23:983-985.

Emerson, et al. 1938. The reductive alkylation of aniline. *J. Am. Chem. Soc.*, 60:2023-2025.

Ermakov, et al. 1981. Use of Mass spectrometry in structural and stereochemical studies. *Chemistry of Heterocyclic Compounds*, 1:72-77.

Everett, et al. 1970. L-Dopa: Effect on concentrations of dopamine, norepinephrine, and serotonin in brains of mice. *Science*, 168:849-850.

Factor, et al. 1992. Clozapine prevents recurrence of psychosis in Parkinson's disease. *Movement Disorders*, 7(2):125-131.

Factor, et al. 2001. Clozapine for the treatment of drug-induced psychosis in Parkinson's disease: Results of the 12 week open label extension in the Psyclops trial. *Movement Disorders*, 16(1):135-139.

Finar, et al. 1954. The preparation and properties of some derivatives of 1-phenylpyrazole, *J. Chem. Soc.*, pp. 2293-2298.

Fisera, et al. 1994. Synthesis of spiro-substituted 1,3-oxazines by a new sequence leading to spiroheterocycles. *Monatshefte für Chemie*, 125:909-919.

Fitzgerald et al., "Possible Role of Vavular Serotonin 5-HT$_{2B}$ Receptors in the Cardiopathy Associated with Fenfluramine," *Molecular Pharmacol.* vol. 57, pp. 75-81 (1999).

Friedman, et al. 1999. Low-dose clozapine for the treatment of drug-induced psychosis in Parkinson's disease. *N. Engl. J. Med.*, 340(10):757-763.

Friedman, et al. 2000. Atypical antipsychotics in the treatment of drug-induced psychosis in Parkinson's disease. *Movement Disorders*, 15(2):201-211.

Friedman, J. H. 1994. Clozapine treatment of psychosis in patients with tardive dystonia: Report of three cases. *Movement Disorders*, 9(3):321-324.

Fuller, R. W. 1982. Drugs acting on serotonergic neuronal systems. In N. N. Osborne (Ed.), *Biology of Serotonergic Transmission*, Chap. 9, pp. 221-247. New York: Wiley.

Gainetdinov, et al. 2001. Genetic animal models: Focus on schizophrenia. *Trends in Neurosciences*, 24(9)527-533.

Gamma, et al. 2000. 3,4-Methylenedioxymethamphetamine (MDMA) modulates cortical and limbic brain activity as measured by [H$_2$$^{15}$O]-PET in healthy humans. *Neuropsychopharmacology*, 23(4):388-395.

Gawley, R. E., & Aubé, J. 1996. *Principles of Asymmetric Synthesis*. New York: Pergamon.

Gershon, M. D., Mawe, G. M., & Branchek, 1. A. 1989. 5-Hydroxytryptamine and enteric neurones. In J. R. Fozard (Ed.), *The Peripheral Actions of 5-Hydroxytryptamine* (pp. 247-273). New York: Oxford University Press.

Gillman, P. K. 2005. Monoamine oxidase inhibitors, opioid analgesics and serotonin toxicity. *British Journal of Anaesthesia*, 95(4):434-441.

Glazer, W.M., "Extrapyramidal side effects, tardive dyskinesia, and the concept of atypicality," *J. Clin. Psychiatry*, vol. 61, Supp. 3, pp. 16-21 (2000).

Glennon, R. A. 1990. Serotonin receptors: Clinical implications. *Neuroscience & Biobehavioral Reviews*, 14:35-47.

Gooben, et al. 2001. Palladium-catalyzed synthesis of aryl ketones from boronic acids and carboxylic acids or anhydrides. *Angew. Chem. Int. Ed.*, 40:3458-3460.

Goodman and Gilman's, 1985. The Pharmacological Basis of Therapeutics, 7$^{th}$ Edition, pp. 340-343 and 403-404.

Gstach et al. 1990. Rearrangement of 3,3-disubstituted 1-aryl-4,5-dihydro-5-oxo-3H-1,2,4-triazolium tetrafluoroborates; Part 1. A versatile synthesis of 1,5-disubstituted 2-aryl-1,2-dihydro-3H-1,2,4-triazol-3-one tetrafluoroborates. *Synthesis*, pp. 803-808.

Guthrie, et al. 1993. The tetrahedral intermediate from the hydration of N-methylformanilide. *Can. J. Chem.*, 71:2109-2122.

Harper, et al. 1964. The chemistry and pharmacology of some 4-aminopiperidines and their derivatives. *J. Med. Chem.*, 44:729-732.

(56) References Cited

OTHER PUBLICATIONS

Hartwig, J. F. 1998. Transition metal catalyzed synthesis of arylamines and aryl ethers from aryl halides and triflates: Scope and mechanism. *Angew. Chem. Int. Ed.*, 37:2047-2067.

Herrick-Davis, et al. 2000. Inverse agonist activity of atypical antipsychotic drugs at human 5-hydroxytryptamine2C receptors. *The Journal of Pharmacology and Experimental Therapeutics*, 295(1):226-232.

Hickinbottom, W. J. 1930. The preparation of secondary alkylarylamines and their purification. *J. Chem. Soc.*, pp. 992-994.

Hirst, et al. 1895. A method for preparing the formyl derivatives of the aromatic amines. *J. Chem. Soc.*, 67:829-831.

Idzikowski, et al. 1991. A dose response study examining the effects of ritanserin on human slow wave sleep. *Br. J. Clin. Pharmac.*, 31:193-196.

Irikura et al., 1971 "New Anticulcer Agents. 1. Synthesis and Biological Activities of 1-Acyl-2-,-3-, -4-substituted Benzamidopiperdines" *J. Medicinal Chemistry* 14(4): 357-361.

Ito et al., "Prediction of Human Drug Clearance from in Vitro and Preclinical Data Using Physiologically Based and Emperical Approaches," *Pharm. Res.*, vol. 22, No. 1, pp. 103-112 (2005).

Jaeger, et al. 1941. Two ketones of the stilboestrol group. *J. Chem. Soc.*, 744-747.

Johnston et al., "Drugs in Development for Parkinson's Disease: An Update," *Current Opin. Investig. Drugs*, vol. 7, No. 1, pp. 25-32 (2006).

Julius, et al. 1990. The 5HT2 receptor defines a family of structurally distinct but functionally conserved serotonin receptors. *Proc. Natl. Acad. Sci. USA*, 87:928-932.

Kalgutkar, et al. 1995. Selective inhibitors of monoamine oxidase (MAO-A and MAO-B) as probes of its catalytic site and mechanism. *Medicinal Research Reviews*, 15(4)325-388. XP002034298.

Kanayama, et al. 2005. New treatment of lumbar disc herniation involving 5-hydroxytryptamine$_{2A}$ receptor inhibitor: A randomized controlled trial. *J. Neurosurg: Spine*, 2:441-446.

Kay, G.G., "The effects of antihistamines in cognition and performance," *J. Allergy Clin. Immunol.*, vol. 105, No. 6, Pt. 2, pp. S622-S627 (2000).

Klapars, et al. 2001. A general and efficient copper catalyst for the amidation of aryl halides and the N-arylation of nitrogen heterocycles. *J. Am. Chem. Soc.*, 123:7727-7729.

Klapars, et al. 2002. A general and efficient copper catalyst for the amidation of aryl halides. *J. Arn. Chem. Soc.*, 124:7421-7428.

Kuehne, et al. 1991(a). Enantioselective syntheses of vinblastine, leurosidine, vincovaline, and 20'-epi-vincovaline. *J. Org. Chem.*, 56(2):513-528.

Kuehne, et al. 1991(b). Total syntheses of Yohimbe alkaloids, with stereoselection for the normal, allo, and 3-epiallo series, based on annelations of 4-methoxy-1,2-dihydropyridones. *J. Org. Chem.*, 56(8):2701-2712.

Kwong, et al. 2002(a). Copper-catalyzed coupling of alkylamines and aryl iodides: An efficient system even in an air atmosphere. *Organic Letters*, 4(4):581-584.

Kwong, et al. 2002(b). A general, efficient, and inexpensive catalyst system for the coupling of aryl iodides and thiols. *Organic Letters*, 4(20):3517-3520.

Kwong, et al. 2003. Mild and efficient copper-catalyzed amination of aryl bromides and primary alkylamines. *Organic Letters*, 5(6):793-796.

Landini, et al. 1974. A convenient synthesis of primary and secondary dialkyl and aryl alkyl sulfides in the presence of phase-transfer catalysts. *Synthesis*, pp. 565-566.

Landolt, et al. 1999. Serotonin-2 receptors and human sleep: Effect of a selective antagonist on EEG power spectra. *Neuropsychopharmacology*, 21(3):455-466.

Letter in response to Written Opinion of the Preliminary Examining Authority in PCT/US2004/001234, dated Mar. 14, 2005.

Leysen, et al. 1978. Serotonergic component of neuroleptic receptors. *Nature*, 272:168-171.

Li, G. Y. 2002. Highly active, air-stable palladium catalysts for the C-C and C-S bond-forming reactions of vinyl and aryl cholrides: Use of commercially available [(t-Bu)$_2$P(OH)]$_2$PdCl$_2$, [(-Bu)$_2$P(OH)PdCl$_2$]$_2$, and [[(t-Bu)$_2$PO...H...OP(t-Bu)$_2$]PdCl]$_2$ as catalysts. *J. Org. Chem.*, 67:3643-3650.

Liechti, et al. 2001. Effects of MDMA (ecstasy) on prepulse inhibition and habituation of startle in humans after pretreament with Citalopram, Haloperidol, or Ketanserin. *Neuropsychopharmacology*, 24(3):240-252.

Linder, et al. 1997. Pharmacogenetics: A laboratory tool for optimizing therapeutic efficiency. *Clinical Chemistry*, 43(2):254-266.

Lowe, et al. 1994. Aza-tricyclic substance P antagonists. *J. Med. Chem.*, 37:2831-2840.

Mansbach, et al. 1988. Dopaminergic stimulation disrupts sensorimotor gating in the rat. *Psychopharmacology*, 94:507-514.

Marek, et al. 2003. Synergistic action of 5-HT$_{2A}$ antagonists and selective serotonin reuptake inhibitors in neuropsychiatric disorders. *Neuropsychopharmacology*, 28:402-412.

Marek, et al. 2005. The selective 5-HT$_{2A}$ receptor antagonist M100907 enhances antidepressant-like behavioral effects of the SSRI fluoxetine. *Neuropsychopharmacology*, 30:2205-2215.

Maubach, K., "Psychiatric Drug Discovery and Development," *Expert Opin. Investig. Drugs.*, vol. 12, No. 9, pp. 1571-1575 (2003).

Mavunkel, et al. 1996. Synthesis and characterization of pseudopeptide bradykinin B2 receptor antagonists containing the 1,3,8-triazaspiro[4.5]decan-4-one ring system. *J. Med. Chem.*, 39:3169-3173.

Mayer, et al. 2003. Ritanserin improves sleep quality in narcolepsy. *Pharmacopsychiatry*, 364:150-155.

Meltzer et al., "Serotonin Receptors: Their Key Role in Drugs to Treat Schizophrenia," *Progress in Neuro-Pyschopharmacology & Biol. Psych.*, vol. 27, pp. 1159-1172 (2003).

Meltzer, et al., Plasma clozapine levels and the treatment of L-DOPA-induced psychosis in Parkinson's disease. *Neuropsychopharmacology*, 12(1):39-45 (1995).

Meltzer, H. Y., The role of serotonin in antipsychotic drug action. *Neuropsychopharmacology*, 21 (2S):106S-115S (1999).

Meng, et al. 1991. Synthetic approaches toward glidobamine, the core structure of the glidobactin antibiotics. *Tetrahedron*, 47(32):62510-6264.

Micovic, et al. 1991. A simple method for preparation of secondary aromatic amines. *Synthesis*, 11:1043-1045.

Miyata, et al. 2000. Sarpogrelate, a selective 5-HT$_{2A}$ serotonergic receptor antagonist, inhibits serotonin-induced coronary artery spasm in a porcine model. *Journal of Cardiovascular Pharmacology*, 35(2) 294-301.

Möehrle, et al. 1990. Sodium mercury edetate dehydrogenation of N-aliphatic substituted 1,2,3,6-tetrahydropyridine derivatives. *Arch. Pharm. (Weinheim)*, 323:109-115.

Morgan et al., "Emerging Drugs for Parkinson's Disease," *Expert Opin. Emerging Drugs.*, vol. 11, No. 3, pp. 403-417 (2006).

Moulignier, A. 1994. Récepteurs centraux de la sérotonine principaux aspects fondamentaux et fonctionnels application thérapeutiques. *Rev. Neurol.*, 150:3-15.

Moune, et al. 1997. Total synthesis of dolatrienoic acid: a subunit of dolastatin 14. *J. Org. Chem.*, 62:3332-3339.

Mullen et al. 2000. (-)-Spiro[1-azabicyclo[2.2.2]octane-3,5'-oxazolidin-2'one], a conformationally restricted analogue of acetylcholine, is a highly selective full agonist at the a7 nicotinic acetylcholine receptor. *J. Med. Chem.*, 43:4045-4050.

Muri, et al. 1998. Synthesis of new benzylic ethers of oximes derived from 1-phenyl-pyrazole compounds. *Synthetic Communications*, 28(7):1299-1321.

Naritomi et al., "Prediction of human hepatic clearance from in vivo animal experiments and in vitro metabolic studies with liver microsomes from animals and humans," *Drug Metab. Dispos.*, vol. 29, No. 10, pp. 1316-1324 (2001).

Negibil et al., "Ablation of Serotonin 5-HT2B Receptors in Mice Leads to Abnormal Cardiac Structure and Function," *Circulation*, vol. 103, pp. 2973-2979 (2001).

Negibil et al., "Serotonin 2B receptor is required for heart development," *PNAS*, vol. 97, No. 17, pp. 9508-9513 (2000).

(56) References Cited

OTHER PUBLICATIONS

Negibil et al., "Serotonin is a novel survival factor of cardiomyocytes: mitochondria as a target of 5-HT$_{2B}$-receptor signaling," *FASEB J.*, vol. 27, No. 10, pp. 1373-1375 (2003).

Ng, et al. 1970. L-dopa-induced release of cerebral monoamines. *Science*, 170:76-77.

Nigam, et al. 1957a. Studies with acetylenes. Part II. Some reactions of Grignard reagents with propargylic halides. Model Iinoleic and Iinolenic acid systems. *J. Chem Soc.*, pp. 3868-3873.

Nigam, et al. 1957b. The conversion of fatty acids into aldehydes. *J. Chem. Soc.*, pp. 3320-3321.

Nordstrom, et al. 1993. High 5-HT$_2$ receptor occupancy in clozapine treated patients demonstrated by PET. *Psychopharmacology*, 110:365-367.

Obach et al., "The Prediction of Human Pharmacolinetic Parameters from Preclinical and In Vitro Metabolism Data," *J. Pharm. Exp. Therap.*, vol. 283, No. 1, pp. 46-58 (1997).

Ogawa, et al. 2005. Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis. European Journal of Pharmacology, 521:156-163.

Olah, et al. 1956. Notiz über die n-formylierung von aminen mit formylfluorid. *Chem. Ber.*, 89:2211-2212.

Old, et al. 2002. Efficient palladium-catalyzed n-arylation of indoles. *Organic Letters*, 2(10):1403-1406.

Pace, et al. 1991. A mutant a subunit of G$_{i2}$ induces neoplastic transformation of Rat-1 cells. *Proc. Natl. Acad. Sci. USA*, vol. 88:7031-7035.

Paiva, et al. 1988. Effects of ritanserin on sleep disturbances of dysthymic patients. *Psychopharmacology*, 96:395-399.

Patel, et al. 2004. The highly selective 5-hydroxytryptamine (5-HT)$_{2A}$ receptor antagonist, EMD 281014, significantly increases swimming and decreases immobility in male congenital learned helpless rats in the forced swim test. *Synapse*, 52:73-75.

Pierce, et al. 1995. 5-hydroxytryptamine-induced synovial plasma extravasation is mediated via 5-hydroxytryptamine2A receptors on sympathetic efferent terminals. *The Journal of Pharmacology and Experimental Therapeutics*, 275(1):502-508.

Pollak, et al. 1999. Clozapine in drug-induced psychosis in Parkinson's disease. *The Lancet*, 353:2041-2042.

R&D Focus Drug News (Jan. 24, 2000). Pimvaserin Acadia lead compounds identified.

R&D Focus Drug News (Nov. 12, 2001). Pimvaserin Acadia preclinical data.

Read, W. T. 1922. Researches on hydantoins. Synthesis of the soporific, 4,4-phenylethylhydantoin(nirvanol). *J. Am. Chem. Soc.*, 44:1746-1755.

Ricci, A. 2000. *Modern Animation Methods*. New York: Wiley-VCH.

Rice, et al. 1955. Raney nickel catalyzed n-alkylation of aniline and benzidine with alcohols. *J. Am. Chem. Soc.*, 77:4052-4054.

Rubiralta, M., Giralt, E., & Diez, A. 1991. *Studies in Organic Chemistry 43. Piperidine: Structure, Preparation, Reactivity and Synthetic Applications of Piperidine and its Derivatives*. New York: Elsevier.

Sadzot, et al. 1989. Hallucinogenic drug interactions at human brain 5-HT$_2$ receptors: Implications for treating LSD-induced hallucinogenesis. Psychopharmacology, 98:495-499.

Saltzman, et al. 1991. Cloning of the human serotonin 5-HT2 and 5-HT1C receptor subtypes. *Biochemical and Biophysical Research Communications*, 181(3):1469-1478.

Saxena, et al. 1990. Cardiovascular effects of serotonin agonists and antagonists. *Journal of Cardiovascular Pharmacology*, 15(Supp. 7):S17-S34.

Scheibye, et al. 1978. Studies on organophosphorus compounds XXI. The dimer of p-methoxyphenylthionophosphine sulfide as thiation reagent. A new route to thiocarboxamides. *Bull. Soc. Chim. Belg.*, 87:229-238.

Schins, et al. 2003. Increased coronary events in depressed cardiovascular patients: 5-HT$_{2A}$ receptor as missing link? *Psychosomatic Medicine*, 65:729-737.

Screttas, et al. 1978. Hydrolithiation of a-olefins by a regiospecific two-step process. Transformation of alkyl phenyl sulfides to alkyl-lithium reagents. *J. Org. Chem.*, 43(6):1064-1071.

Scriabine, A., "Psychiatric Drug Discovery and Development," *CNS Drug Rev.*, vol. 9, No. 3, pp. 319-326 (2003).

Sharpley, et al. 1994. Slow wave sleep in humans: Role of 5-HT$_{2A}$ and 5-HT$_{2C}$ receptors. *Neuropharmacology*, 33(3/4):467-471.

Sica, D.A., "Alpha$_1$-Adrenergic Blockers: Currant Usage Considerations," *J. Clin. Hypertension*, vol. 7, pp. 757-762 (2005).

Smith, et al. 1995. New spiropiperdines as potent and selective non-peptide tachykinin NK$_2$ receptor antagonists. *J. Med. Chem.*, 38(19):3772-3779.

Stefancich, et al. 1984. Agenti antiinfiammatori non-steroidei: Nota III-sintesi ed attività analgesica-antiinfiammatoria di 4-(pirrol-1-il)-fenilacetamidi e di 4-(pirrol-1-il)fenetilamine. *Farmaco Ed. Sci.*, 39(9):752-764.

Stoner et al., "Integrated oral bioavailability projection using in vitro screening data as a selection tool in drug discovery," *Int. J. Pharm.*, vol. 269, No. 1, pp. 241-249 (2004).

Stryjer, et al. 2003. Treatment of neuroleptic-induced akathisia with the 5-HT$_{2A}$ antagonist trazodone. *Clinical Neuropharmacology*, 26(3):137-141.

Tolstikov et al.1991 "Synthesis and Reactivity of N-substituted aminoamides, antiarrhythmic and local anaesthetic activity" *Russian Chemical Reviews* 60(4):420434.

Tsukamoto, et al. 1995. Synthesis and structure-activity studies of a series of 1-oxa-2,8-diazaspiro[4.5]decan-3-ones and related compounds as M$_1$ muscarinic agonists. *Chem. Pharm. Bull.*, 43(9):1523-1529.

Vallar, et al. 1987. Altered G$_s$ and adenylate cyclase activity in human GH-secreting pituitary adenomas. *Nature*, 330:566-568.

Van Laar, et al. 2001. Subchronic effects of the GABA-agonist lorazepam and the 5-HT$_{2A/2C}$ antagonist ritanserin on driving performance, slow wave sleep and daytime sleepiness in healthy volunteers. *Psychopharmacology*, 154:189-197.

Vanover et al., "ACP-103, A 5-HT2A Receptor Inverse Agonist, a Novel Potential Treatment for Psychosis," *Schizophrenia Research*, vol. 60, No. 1, Supp. [S], p. 317 (2003).

Vanover et al., "ACP-103, A 5-HT2A Receptor Inverse Agonist: Safety, Tolerability and Pharmacokinetics in Healthy Volunteers," *International J. Neuropsychopharmacology*, vol. 7, No. Supp. 2, pp. S253 (2004).

Vanover et al., "Pharmacological Characterization of AC-90179 [2-(4-Methoxy-phenyl)-N-(4-methyl-benzyl)-N-(1-methyl-piperidiny-4-yl)-acetamide Hydrochloride]: A Selective Serotonin 2A Receptor Inverse Agonist," *J. Pharmacology & Experimental Therapeutics*, vol. 310, No. 3, pp. 943-951 (2004).

Varma, et al. 1999. Microwave-accelerated solvent-free synthesis of thioketones, thiolactones, thioamides, thionoesters, and thioflavonoids. *Organic Letters*, 1(5):697-700.

Viola, et al. 2002. Ritanserin, a serotonin-2 receptor antagonist, improves ultradian sleep rhythmicity in young poor sleepers. *Clinical Neurophysiology*, 113:429-434.

Vogel, A. I. 1948. Physical properties and chemical constitution. Part XIX. Five-membered and six-membered carbon rings. *J. Chem. Soc.*, pp. 1809-1813.

Vogl, et al. 2002. Palladium-catalyzed monoarylation of nitroalkanes. *J. Org. Chem.*, 67(1):106-111.

Wade, et al. 2000. Application of base cleavable safety catch linkers to solid phase library production. *J. Comb. Chem.*, 2(3):266-275.

Weiner, et al. 2001. 5-Hydroxytryptamine$_{2A}$ receptor inverse agonists as antipsychotics. *The Journal of Pharmacology and Experimental Therapeutics*, 299(1):268-276.

Whitmore, et al. 1942. Abnormal Grignard reactions. XII. Sterically hindered aliphatic carbonyl compounds. II. Ketones containing the dineopentylcarbinyl group. *J. Am. Chem. Soc.*, 64:1247-1251.

Whitmore, et al. 1947. Higher hydrocarbons. IV. Six phenyleicosanes and six cyclohexyleicosanes. *J. Am. Chem. Soc.*, 69:235-237.

Wirshing et al., "Novel Antipsychotics: Comparison of Weight Gain Liabilities," *J. Clin. Psychiatry*, vol. 21, No. 6, pp. 579-587 (1999).

Wolf, V. V. 1952. Über alkin-amine I. Aryl-propargyl-amine. *Liebigs Ann. Chem.*, 576:35-45.

(56) References Cited

OTHER PUBLICATIONS

Wolfe, et al. 1996. An improved catalyst system for aromatic carbon-nitrogen bond formation: The possible involvement of bis(phosphine) palladium complexes as key intermediates. *J. Am. Chem. Soc.*, 118:7215-7216.
Yamada, et al. 1998. Alternative synthesis of TTF donors with a dioxolane ring, and synthesis of their dithiolane and oxathiolane analogues. *Tetrahedron Letters*, 39:7709-7712.
Yang, et al. 1999. Palladium-catalyzed amination of aryl halides and sulfonates. *Journal of Organometallic Chemistry*, 576: 125-146.
Yasuhara, et al. 2000. An activated phosphate for an efficient amide and peptide coupling reagent. *J. Chem. Soc., Perkin Trans.* 1,17:2901-2902.
Yin, et al. 2002. Pd-catalyzed intermolecular amidation of aryl halides: The discovery that xantphos can be trans-chelating in a palladium complex. *J. Am. Chem. Soc.*, 124:6043-6048.
Yoshida, et al. 1998. Marked improvement of tardive dystonia after replacing haloperidol with risperidone in a schizophrenic patient. *Clinical Neuropharmacology*, 21(1):68-69.
Examiner's Amendment dated Sep. 1, 2009, from U.S. Appl. No. 10/759,561, filed Jan. 15, 2004.
International Preliminary Examination Report dated Jan. 15, 2004, for PCT/US02/41476.
International Preliminary Examination Report dated Mar. 18, 2003, for PCT/US01/07187.
International Preliminary Examination Report for PCT/US03/19797 dated Jul. 28, 2004.
International Preliminary Report on Patentability dated Mar. 27, 2007, for PCT/US2005/034376.
International Preliminary Report on Patentability dated Mar. 27, 2007, for PCT/US2005/034813.
International Preliminary Report on Patentability for PCT/US2004/001234 dated Apr. 14, 2005.
International Search Report and Written Opinion dated Sep. 29, 2005, for PCT/US2005/017808.
International Search Report dated Jan. 30, 2006, for PCT/US2005/034376.
International Search Report dated Jan. 30, 2006, for PCT/US2005/034813.
International Search Report dated Jul. 17, 2001 for PCT/US01/07187.
International Search Report dated May 8, 2003 for PCT/US02/41476.
International Search Report for PCT/US03/19797 dated Dec. 3, 2003.
International Search Report for PCT/US2004/001234 dated Sep. 8, 2004.
International Written Opinion for PCT/US2004/001234 dated Sep. 8, 2004.
Interview Summary dated Nov. 17, 1998, from U.S. Appl. No. 08/965,947, filed Nov. 7, 1997, now U.S. Pat. No. 5,955,281.
Interview Summary dated Jan. 28, 2009, from U.S. Appl. No. 10/759,561, filed Jan. 15, 2004.
Notice of Allowability dated Dec. 8, 2003, from U.S. Appl. No. 09/800,096, filed Mar. 6, 2001, now U.S. Pat. No. 6,815,458.
Notice of Allowability, Notice of Allowance and Fee(s) Due, and Interview Summary dated Dec. 15, 2006, from U.S. Appl. No. 11/154,083, filed Jun. 16, 2005.
Notice of Allowance and Fee(s) Due and Notice of Allowability dated Dec. 5, 2003, from U.S. Appl. No. 10/409,782, filed Apr. 7, 2003, now U.S. Pat. No. 6,756,393.
Notice of Allowance and Fee(s) Due and Notice of Allowability dated Feb. 11, 2005, from U.S. Appl. No. 10/329,719, filed Dec. 23, 2002, now U.S. Pat. No. 6,911,452.
Notice of Allowance and Fee(s) Due and Notice of Allowability dated Jul. 12, 2005, from U.S. Appl. No. 10/601,070, filed Jun. 20, 2003.
Notice of Allowance and Fee(s) Due and Notice of Allowability dated Jun. 19, 2007, from U.S. Appl. No. 11/418,322, filed May 3, 2006.
Notice of Allowance and Fee(s) Due and Notice of Allowability dated Mar. 29, 2006, from U.S. Appl. No. 10/601,070, filed Jun. 20, 2003.
Notice of Allowance and Fee(s) Due and Notice of Allowability dated Mar. 5, 2007, from U.S. Appl. No. 10/601,070, filed Jun. 20, 2003.
Notice of Allowance and Fee(s) Due and Notice of Allowability dated May 15, 1997, from U.S. Appl. No. 08/273,669, filed Jul. 12, 1994, now U.S. Pat. No. 5,707,798.
Notice of Allowance and Fee(s) Due and Notice of Allowability dated Nov. 20, 2001, from U.S. Appl. No. 09/413,626, filed Oct. 6, 1999, now U.S. Pat. No. 6,358,698.
Notice of Allowance and Fee(s) Due and Notice of Allowability dated Sep. 4, 1998, from U.S. Appl. No. 08/954,724, filed Oct. 20, 1997, now U.S. Pat. No. 5,912,132.
Notice of Allowance and Fee(s) Due and Notice of Allowability dated Jun. 17, 2009, from U.S. Appl. No. 10/759,561, filed Jan. 15, 2004.
Notice of Allowance and Fee(s) Due and Notice of Allowability dated Jan. 26, 2010 from U.S. Appl. No. 11/416,527, filed May 3, 2006, now U.S. Pat. No. 7,732,462.
Notice of Allowance and Fee(s) Due and Notice of Allowability dated Sep. 22, 2009 from U.S. Appl. No. 11/416,855, filed May 3, 2006, now U.S. Pat. No. 7,659,285.
Notice of Allowance and Fee(s) Due and Notice of Allowability dated Nov. 23, 2010 from U.S. Appl. No. 12/759,664, filed Apr. 13, 2010.
Notice of Allowance and Fee(s) Due and Notice of Allowability dated Mar. 3, 2011, from U.S. Appl. No. 12/759,664, filed Apr. 13, 2010.
Notice of Allowance and Fee(s) Due and Notice of Allowability dated Feb. 6, 2008, from U.S. Appl. No. 11/122,293, filed May 4, 2005, now U.S. Pat. No. 7,393,861.
Notice of Allowance and Fee(s) Due and Notice of Allowability dated Jul. 23, 2008, from U.S. Appl. No. 11/299,566, filed Dec. 12, 2005, now U.S. Pat. No. 7,538,222.
Notice of Allowance and Fee(s) Due and Notice of Allowability dated Sep. 9, 2008, from U.S. Appl. No. 11/417,866, filed May 3, 2006, now U.S. Pat. No. 7,476,682.
Office Action dated Apr. 25, 2002, from U.S. Appl. No. 09/800,096, now U.S. Pat. No. 6,815,458.
Office Action dated Apr. 6, 2007, from U.S. Appl. No. 11/418,322, filed May 3, 2006.
Office Action dated Aug. 22, 2007 in U.S. Appl. No. 11/122,293, filed May 4, 2005.
Office Action dated Feb. 28, 2001, from U.S. Appl. No. 09/413,626, filed Oct. 6, 1999, now U.S. Pat. No. 6,358,698.
Office Action dated Feb. 5, 2007, from U.S. Appl. No. 11/299,566, filed Dec. 17, 2007.
Office Action dated Jan. 17, 2006, from U.S. Appl. No. 11/154,083, filed Jun. 26, 2005.
Office Action dated Jan. 21, 2003, from U.S. Appl. No. 09/800,096, now U.S. Pat. No. 6,815,458.
Office Action dated Jan. 23, 2007, from U.S. Appl. No. 11/418,322, filed May 3, 2006.
Office Action dated Jul. 15, 2003, from U.S. Appl. No. 09/800,096, now U.S. Pat. No. 6,815,458.
Office Action dated Jun. 26, 2006, from U.S. Appl. No. 11/154,083, filed Jun. 26, 2006.
Office Action dated Mar. 27, 1998, from U.S. Appl. No. 08/954,724, filed Oct. 20, 1997, now U.S. Pat. No. 5,912,132.
Office Action dated May 21, 2004, from U.S. Appl. No. 10/329,719, filed Dec. 23, 2002, now U.S. Pat. No. 6,911,452.
Office Action dated May 8, 2007, from U.S. Appl. No. 11/417,866, filed May 3, 2006.
Office Action dated Nov. 4, 2004, from U.S. Appl. No. 10/601,070, filed Jun. 20, 2003.
Office Action dated Oct. 10, 2007, from U.S. Appl. No. 10/759,561, filed Jan. 15, 2004.
Office Action dated Oct. 5, 2006, from U.S. Appl. No. 11/418,322, filed May 3, 2006.
Office Action dated Sep. 14, 1998, from U.S. Appl. No. 08/965,947, filed Nov. 7, 1997, now U.S. Pat. No. 5,955,281.
Office Action dated Sep. 30, 2010 from U.S. Appl. No. 12/759,664, filed Apr. 13, 2010.
Official Communication in European Patent Application No. 04702584.6-2123, dated Apr. 5, 2006.
Official Communication in European Patent Application No. 04702584.6-2123, dated Feb. 23, 2007.

(56) References Cited

OTHER PUBLICATIONS

Reply to Communication in European Patent Application No. 04702584.6-2123, dated Aug. 16, 2006.
Reply to Communication in European Patent Application No. 04702584.6-2123, dated May 4, 2007.
Written Opinion dated Nov. 22, 2002 for PCT/US01/07187.
Written Opinion dated Sep. 9, 2003, for PCT/US02/41476.
Written Opinion for PCT/US03/19797 dated Apr. 5, 2004.
Written Opinion of the International Searching Authority dated Jan. 30, 2006, for PCT/US2005/034376.
Written Opinion of the International Searching Authority dated Jan. 30, 2006, for PCT/US2005/034813.
Written Opinion of the Preliminary Examining Authority in in PCT/US2004/001234, dated Dec. 15, 2004.
Ballard, et al. 2013. Pimavanserin for patients with Parkinson's disease psychosis: a randomized, placebo-controlled phase 3 trial. *Lancet.* (published online Nov. 1, 2013 at http://dx.doi.org/10.1016/S0140-6736(13)62157-1).
"ACP-103," Drugs of the Future, Prous Science, ES, vol. 31(11):939-943 (2006).
Grahnen et al., "Reduction of Haloperidol-induced Side Effects by ACP-103 in Healthy Volunteers," Clin. Pharmacol. Ther. 77(2):P98 (2005).
Li et al., "ACP-103, a 5-HT2A/2C inverse agonist, potentiates haloperidol-induced dopamine release in rat medical prefrontal cortex and nucleus accumbens," Psychopharmacology, vol. 183(2):144-153 (2005).
Meltzer et al., "Co-therapy with pimavanserin and risperidone 2 mg provides an improved clinical profile," Schizophrenia Res., vol. 98:16 (2008).
Non-Final Office Action dated Jan. 6, 2009, in U.S. Appl. No. 10/759,561, filed Jan. 15, 2004.
Non-Final Office Action dated Jul. 11, 2008, in U.S. Appl. No. 10/759,561, filed Jan. 15, 2004.
Roberts, C., 2006, "Drug Evaluation: ACP-103, a 5-HT2A Receptor Inverse Agonist," *Current Opinion Investigative Drugs*, vol. 7(7):653-660.
Vanover et al., 2006, "Pharmacological and Behavioral Profile of N-(4-fluorophenylmethyl)-N-(1-methylpiperidin'4-y1)-N'-(4-(2-methylpropyloxy)phenylmethyl) Carbamide (2R, 3R)-Dihydroxybutanedioate (2:1) (ACP-103), a Novel 5-Hydroxytrptamine 2A Receptor Inverse Agonist," J. Pharmacology & Experimental Therapeutics, vol. 317(2):910-918.
Poewe, Werner, "Psychosis in Parkinson's Disease," Movement Disorders, 18(6):S80-S87 (2003).

\* cited by examiner

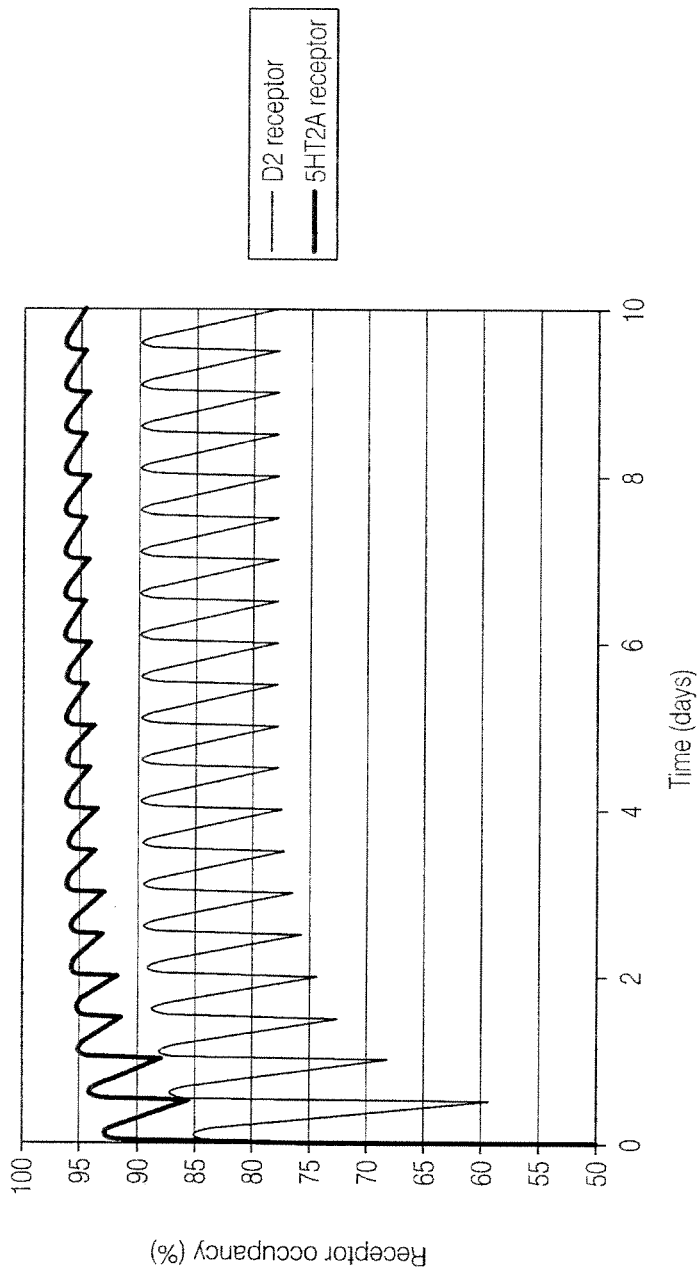

COMBINATION OF PIMAVANSERIN AND RISPERIDONE FOR THE TREATMENT OF PSYCHOSIS

RELATED APPLICATIONS

This application is a divisional of U.S. application Ser. No. 12/051,807, filed Mar. 19, 2008, which claims the benefit of U.S. Provisional Application Nos. 60/895,735, filed Mar. 19, 2007; 60/908,921, filed Mar. 29, 2007; 61/012,771, filed Dec. 10, 2007; and 61/026,092, filed Feb. 4, 2008, all of which are entitled "COMBINATIONS OF N-(1-METHYLPIPERI-DIN-4YL)-N-(4-FLUOROPHENYLMETHYL)-N'-(4-(2-(METHYLPROPYLOXY)PHENYLMETHYL) WITH ANTIPSYCHOTICS" and are incorporated herein by reference in their entirety.

BACKGROUND OF THE INVENTION

1. Field of the Invention

The present invention relates to the fields of chemistry and medicine. More particularly, some embodiments of the invention relate to co-administration of 5-HT2A receptor inverse agonists or antagonists with antipsychotics.

2. Description of the Related Art

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, *Rev. Neurol.* 150:3-15, (1994)). Peripheral functions in the cardiovascular, hematological and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, *Biology of Serotonergic Transmission*, 1982; Boullin, *Serotonin In Mental Abnormalities* 1:316 (1978); Barchas, et al., *Serotonin and Behavior*, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al., *The Peripheral Actions of 5-Hydroxytryptamine*, 246 (1989); Saxena, et al., *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s).

Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology*, 21:106S-115S (1999); Barnes & Sharp, *Neuropharmacology*, 38:1083-1152 (1999); Glennon, *Neurosci. Biohehavioral Rev.*, 14:35 (1990)).

Given the broad distribution of serotonin within the body and its role in a wide range of physiological and pathological processes, it is understandable that there is tremendous interest in drugs that affect serotonergic systems (Gershon, et al., *The Peripheral Actions of 5-Hydroxytryptamine*, 246 (1989); Saxena, et al., *J. Cardiovascular Pharmacol.* 15: Supp. 7 (1990)).

The effects of serotonin are mediated by at least 15 genetically distinct 5-HT receptor subtypes have been identified and assigned to one of seven families (5-HT1-7). Each subtype displays a unique distribution, preference for various ligands, and functional correlate(s). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis. Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

Schizophrenia is a particularly devastating neuropsychiatric disorder that affects approximately 1% of the human population. It has been estimated that the total financial cost for the diagnosis, treatment, and lost societal productivity of individuals affected by this disease exceeds 2% of the gross national product (GNP) of the United States. Current treatment primarily involves pharmacotherapy with a class of drugs known as antipsychotics. Antipsychotics are effective in ameliorating positive symptoms (e.g., hallucinations and delusions), yet they frequently do not improve negative symptoms (e.g., social and emotional withdrawal, apathy, and poverty of speech).

Currently, nine major classes of antipsychotics are prescribed to treat psychotic symptoms. Use of these compounds is limited, however, by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of some of these adverse effects. However, atypical agents also have the potential for serious side effects including increased risk of stroke, abnormal shifts in sleep patterns, extreme tiredness and weakness, metabolic disorders (including hyperglycemia and diabetes), and weight gain. One of the most common reasons for noncompliance and discontinued use of antipsychotic medication is weight gain. Noncompliance can lead to increased hospitalization and health care costs.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects as well as some additional undesired effects of antipsychotic therapies such as a worsening of depression symptoms, anhedonia and impairment of cognitive processes. Antagonism of 5-HT2A receptors is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects or other undesired effects associated with blockade of dopamine $D_2$ receptors.

Traditionally, GPCRS such as the 5-HT2A receptor have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor responses.

SUMMARY OF THE INVENTION

Some embodiments described herein include a method of treating a condition amenable to treatment with an antipsychotic, comprising administering a first amount of a 5-HT2A inverse agonist or antagonist and administering a second amount of an antipsychotic agent, wherein the first and second amounts are such that an efficacious effect is achieved faster than when the antipsychotic agent is administered alone at an efficacious dose. In some embodiments, the second amount is less than a maximal dose of the antipsychotic agent when it is administered alone. In some embodiments, the second amount is less than an efficacious dose of the antipsychotic agent when it is administered alone.

In some embodiments, the first and second amounts are such that the severity or onset of one or more side effects due to the antipsychotic agent are reduced as compared to administration of an efficacious dose of the antipsychotic agent alone. In some embodiments, the side effect is weight gain. In some embodiments, the side effect is selected from the group consisting of an extrapyramidal side effect, a histaminic side effect, an alpha adrenergic side effect, and an anticholinergic side effect. In some embodiments, the side effect is selected from the group consisting of stroke, tremors, sedation, gastrointestinal problems, neurological problems, increased risk of death, cerebrovascular events, movement disorder, dystonia, akathisia, parkinsoniam movement disorder, tardive dyskinesia, cognitive disorders, prolactinemia, catalepsy, psychosis, neuroleptic malignant syndrome, heart problems, pulmonary problems, diabetes, liver failure, suicidality, sedation, orthostatic hypotension, choking, dizziness, tachycardia, blood abnormalities, abnormal triglyceride levels, increased cholesterol levels, dyslipidemia, hyperglycemia, syncope, seizures, dysphagia, priapism, thrombotic thrombocytopenic purpura, disruption of body temperature regulation, insomnia, agitation, anxiety, somnolence, aggressive reaction, headache, constipation, nausea, dyspepsia, vomiting, abdominal pain, saliva increase, toothache, rhinitis, coughing, sinusitis, pharyngitis, dyspnea, back pain, chest pain, fever, rash, dry skin, seborrhea, increased upper respiratory infection, abnormal vision, arthralgia, hypoaesthesia, manic reaction, concentration impairment, dry mouth, pain, fatigue, acne, pruritus, myalgia, skeletal pain, hypertension, diarrhea, confusion, asthenia, urinary incontinence, sleepiness, increased duration of sleep, accommodation disturbance, palpitations, erectile dysfunction, ejaculatory dysfunction, orgastic dysfunction, lassitude, increased pigmentation, increased appetite, automatism, increased dream activity, diminished sexual desire, nervousness, depression, apathy, catatonic reaction, euphoria, increased libido, amnesia, emotional liability, nightmares, delirium, yawning, dysarthria, vertigo, stupor, paraesthesia, aphasia, hypoesthesia, tongue paralysis, leg cramps, torticollis, hypotonia, coma, migrain, hyperreflexia, choreoathetosis, anorexia, flatulence, stomatitis, melena, hemorrhoids, gastritis, fecal incontinence, erutation, gastroeophageal reflux, gastroenteritis, esophagitis, tongue discoloration, choleithiasis, tongue edema, diverticulitis, gingivitis, discolored feces, gastrointestinal hemorrhage, hematemesis, edema, rigors, malaise, pallor, enlarged abdomen, ascites, sarcoidosis, flushing, hyperventilation, bronchospasm, pneumonia, tridor, asthma, increased sputum, aspiration, photosensitivity, increased sweating, acne, decreased sweating, alopecia, hyperkeratosis, skin exfoliation, bullous eruption, skin ulceration, aggravated psoriasis, furunculosis, verruca, dermatitis lichenoid, hypertrichosis, genital pruritus, urticaria, ventricular tachycardia, angina pectoris, premature atrial contractions, T wave inversion, ventricular extrasystoles, ST depression, AV block, myocarditis, abnormal accommodation, xerophthalmia, diplopia, eye pain, blepharitis, photopsia, photophobia, abnormal lacrimation, hyponatremia, creatine phosphokinase increase, thirst, weight decrease, decreased serum iron, cachexia, dehydration, hypokalemia, hypoproteinemia, hyperphosphatemia, hypertrigylceridemia, hyperuricemia, hypoglycemia, polyuria, polydipsia, hemturia, dysuria, urinary retention, cystitis, renal insufficiency, arthrosis, synostosis, bursitis, arthritis, menorrhagia, dry vagina, nonpeurperal lactation, amenorrhea, female breast pain, leukorrhea, mastitis, dysmenorrhea, female perineal pain, intermenstrual bleeding, vaginal hemorrhage, increased SGOT, increased SGPT, cholestatic hepatitis, cholecystitis, choleithiasis, hepatitis, hepatocellular damage, epistaxis, superficial phlebitis, thromboplebitis, thrombocytopenia, tinnitus, hyperacusis, decreased hearing, anemia, hypochromic anemia, normocytic anemia, granulocytopenia, leukocytosis, lymphadenopathy, leucopenia, Pelger-Huet anomaly, gynecomastia, male breast pain, antidiuretic hormone disorder, bitter taste, micturition disturbances, oculogyric crisis, abnormal gait, involuntary muscle contraction, and increased injury.

In some embodiments, the condition is psychosis and the efficacious effect is an antipsychotic effect. In some embodiments, the psychosis is associated with schizophrenia. In some embodiments, the psychosis is acute psychotic exacerbation. In some embodiments, the condition amenable to treatment is selected from the group consisting of schizophrenia, bipolar disorder, agitation, psychosis, behavioral disturbances in Alzheimer's disease, depression with psychotic features or bipolar manifestations, obsessive compulsive disorder, post traumatic stress syndrome, anxiety, personality disorders (borderline and schizotypal), dementia, dementia with agitation, dementia in the elderly, Tourette's syndrome, restless leg syndrome, insomnia, social anxiety disorder, dysthymia, ADHD, and autism.

Another embodiment described herein includes a method of inducing a rapid onset of an antipsychotic effect, comprising co-administering a 5-HT2A inverse agonist or antagonist and an antipsychotic agent to a subject suffering from psychosis such that there is a rapid onset of antipsychotic effect.

Another embodiment described herein includes a method of inducing a rapid onset of an antidepressant effect, comprising co-administering a 5-HT2A inverse agonist or antagonist and an antipsychotic agent to a subject suffering from depression such that there is a rapid onset of antidepressant effect.

Another embodiment described herein includes a method of increasing the percentage of patients responding to antipsychotic therapy, comprising co-administering a 5-HT2A inverse agonist or antagonist and an antipsychotic agent to a subject suffering from psychosis such that a greater percentage of patients experience an efficacious effect than when the antipsychotic agent is administered alone at an efficacious dose.

Another embodiment described herein includes a method of reducing or preventing weight gain associated with administration of an antipsychotic agent, comprising co-administering a 5-HT2A inverse agonist or antagonist with the antipsychotic agent to a subject at risk of or suffering from weight gain associated with administration of an antipsychotic agent.

Another embodiment described herein includes a method of increasing patient compliance during antipsychotic therapy, comprising co-administering a 5-HT2A inverse agonist or antagonist with an antipsychotic agent, wherein the doses of co-administration are such that patient compliance is increased as compared to compliance when administering an efficacious dose of the antipsychotic agent alone.

Another embodiment described herein includes a method of reducing or preventing increased serum glucose associated with administration of an antipsychotic agent, comprising co-administering a 5-HT2A inverse agonist or antagonist with the antipsychotic agent to a subject at risk of or suffering from increased serum glucose associated with administration of an antipsychotic agent.

Another embodiment described herein includes a method of reducing or preventing increased serum glucose and reducing or preventing weight gain associated with administration of an antipsychotic agent, comprising co-administering a 5-HT2A inverse agonist or antagonist with the antipsychotic agent to a subject at risk of or suffering from increased serum glucose and weight gain associated with administration of an antipsychotic agent.

Another embodiment disclosed herein includes a pharmaceutical composition that includes a first amount of a 5-HT2A inverse agonist or antagonist and a second amount of an antipsychotic agent, wherein the first and second amounts are such that when the composition is administered, an efficacious antipsychotic effect is achieved faster than when the antipsychotic agent is administered alone at an efficacious dose. In some embodiments, the second amount is less than a maximal dose of the antipsychotic agent when it is administered alone. In some embodiments, the second amount is less than an efficacious dose of the antipsychotic agent when it is administered alone.

Another embodiment disclosed herein includes a package that includes a first amount of a 5-HT2A inverse agonist or antagonist and instructions for administering the first amount of the 5-HT2A inverse agonist or antagonist and a second amount of an antipsychotic agent, wherein the first and second amounts are such that an efficacious antipsychotic effect is achieved faster than when the antipsychotic agent is administered alone at an efficacious dose. In some embodiments, the second amount is less than a maximal dose of the antipsychotic agent when it is administered alone. In some embodiments, the second amount is less than an efficacious dose of the antipsychotic agent when it is administered alone.

In some of the above-mentioned embodiments, the antipsychotic agent is a typical antipsychotic. In some embodiments, the antipsychotic agent is an atypical antipsychotic. In some embodiments, the antipsychotic agent is a D2 antagonist. In some embodiments, the antipsychotic agent is risperidone. In some embodiments, the antipsychotic agent is haloperidol. In some embodiments, the antipsychotic agent is selected from the group consisting of a phenothiazine, a phenylbutylpiperidine, a dibenzapine, a benzisoxidil, and a salt of lithium. In some embodiments, the phenothiazine is selected from the group consisting of chlorpromazine (Thorazine®), mesoridazine (Serentil®), prochlorperazine (Compazine®), thioridazine (Mellaril), Fluphenazine (Prolixin®), Perphenazine (Trilafon®), and Trifluoperazine (Stelazine®). In some embodiments, the phenylbutylpiperidine is pimozide (Orap®). In some embodiments, the dibenzapine is selected from the group consisting of clozapine (Clozaril®), loxapine (Loxitane®), olanzapine (Zyprexa®), and quetiapine (Seroquel®). In some embodiments, the benzisoxidil is ziprasidone (Geodon®). In some embodiments, the salt of lithium is lithium carbonate. In some embodiments, the antipsychotic agent is selected from the group consisting of Aripiprazole (Abilify®), Etrafon®, Droperidol (Inapsin®), Thioridazine (Mellaril®), Thiothixene (Navane®), Promethazine (Phenergan®), Metoclopramide (Reglan®), Chlorprothixene (Taractan®), Triavil®, Molindone (Moban®), Sertindole (Serlect®), Droperidol, Amisulpride (Solian®), Melperone, Paliperidone (Invega®), and Tetrabenazine.

Another embodiment described herein includes a method of reducing or preventing hyperprolactinemia caused by administration of risperidone, comprising co-administering a 5-HT2A inverse agonist or antagonist with less than 6 mg per day of risperidone to a subject at risk of or suffering from hyperprolactinemia associated with administration of risperidone.

In some of any of the above-mentioned embodiments, the 5-HT2A inverse agonist or antagonist is the compound of formula (I):

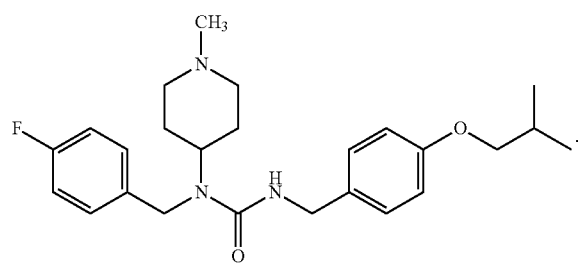

In other embodiments, the 5-HT2A inverse agonist or antagonist is a compound selected from the group consisting of:

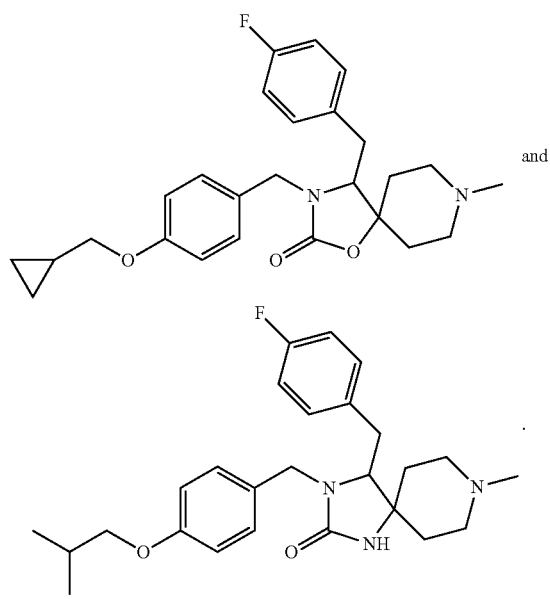

and

In still other embodiments, the 5-HT2A inverse agonist or antagonist is selected from the group consisting of Adatanserin, Altanserin, Benanserin, Blonanserin, Butanserin, Cinanserin, Eplivanserin, Fananserin, Flibanserin, Glemanserin, Iferanserin, Ketanserin, Lidanserin, Mianserin, Pelanserin, Pruvanserin, Ritanserin, Seganserin, and Tropanserin.

In some of any of the above-mentioned methods, the administration is to a human less than eighteen years of age.

Another embodiment described herein includes a method of treatment that includes determining that a first pharmaceutical agent modulates a pharmacological property of a second pharmaceutical agent, determining that the first pharmaceutical agent has a longer half-life than a second pharmaceutical agent, and co-administering the first and second pharmaceutical agent to a patient. In some embodiments, the pharmacological property is receptor occupancy. In some embodiments, the pharmacological property is the minimum efficacious dose of the second pharmaceutical agent. In some embodiments, the half-life of the first agent is at least about 1.5 times higher than the half-life of the second agent. In some embodiments, the co-administration results in the second agent being present at an efficacious level during at least about 50% of the time between successive dosing of the second agent. In some embodiments, the co-administration results in the second agent being present at an efficacious level during substantially all of the time between successive dosing of the second agent and wherein said second agent would not have been present at an efficacious level for substantially all of the period between successive dosing if first agent had been administered alone with the same dosing schedule and dosage. In some embodiments, the first pharmacological agent and said second pharmacological agent are administered at doses and time intervals which result in said second pharmacological agent being present at an efficacious level for a period of time which is longer than the period of time which said second therapeutic agent would be present at an efficacious level if said second therapeutic agent had been administered alone.

Another embodiment described herein includes a method of determining whether a test therapeutic agent is a good candidate for combination therapy with a therapeutic agent having a first half-life comprising obtaining a test therapeutic agent having a second half-life that is longer than said first half-life and evaluating whether administering said test therapeutic agent in combination with said therapeutic agent allows said therapeutic agent to be efficacious at a level at which it is not efficacious when administered alone. Some embodiments include determining whether said test therapeutic agent enhances a level of receptor occupancy, wherein said receptor is targeted by said therapeutic agent.

BRIEF DESCRIPTION OF THE DRAWINGS

FIGS. 31A and 31B are graphs depicting 5-HT2A and D2 receptor occupancy upon administration of 1 mg risperidone twice daily alone (FIG. 31A) and in combination (FIG. 31B) with pimavanserin including the contribution from paliperidone.

DETAILED DESCRIPTION OF CERTAIN EMBODIMENTS

Figure 1A:
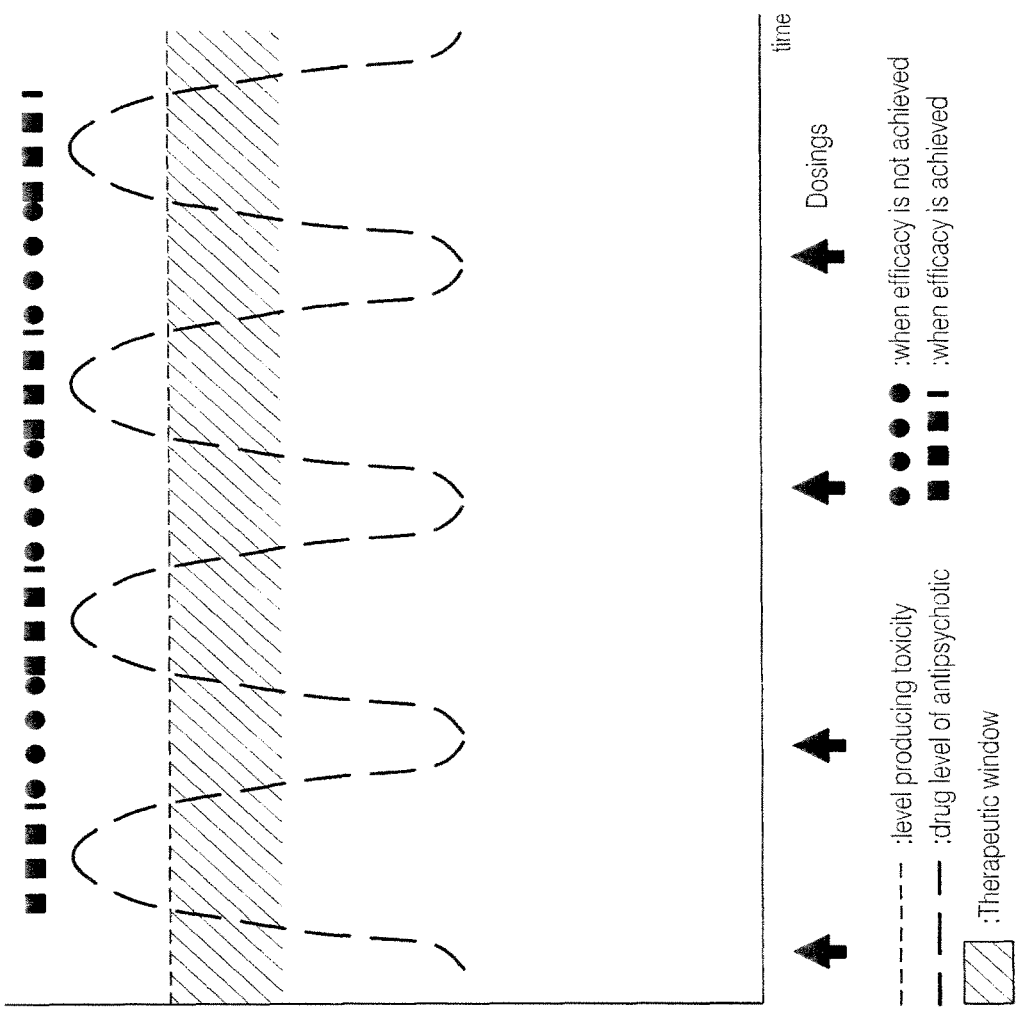
FIG. 1A is a graph depicting the drug level and therapeutic window for single agent administration.

Some embodiments include the co-administration of a 5-HT2A inverse agonist or antagonist along with an antipsychotic agent. In some embodiments, the 5-HT2A inverse agonist or antagonist enhances the efficacy of the antipsychotic agent while decreasing the side effects caused by the antipsychotic agent. While not being bound by any particular theory, it is believed that the 5-HT2A inverse agonist or antagonist can modulate the D2 antagonistic activity of the antipsychotic agent. Specifically, it is believed that the 5-HT2A inverse agonist or antagonist enhances the D2 antagonistic activity in regions of the brain responsible for psychotic effects (e.g., hallucinations) while at the same time diminishing D2 antagonistic activity in regions of the brain which cause adverse side effects (e.g., cognitive impairment, depression, and extrapyrmaidal side effects). These two actions, decreasing undesired effects of D2 receptor blockade in brain regions associated with motoric control or cognitive function, while simultaneously increasing the effectiveness of the desired antipsychotic actions will result in increased antipsychotic efficacy with diminished side effects.

By "co-administration" or administration "in combination," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route. For example, in some embodiments, both agents are administered orally. In another embodiment, the agents are administered through different routes. For example, in one embodiment, one agent is administered orally and the other agent is administered i.v.

In some embodiments, use of the 5-HT2A inverse agonist or antagonist allows the dose of the antipsychotic agent to be reduced. This reduction results in an elimination or reduction in the severity of side effects caused by the antipsychotic agent. In addition, in some embodiments, reduction of the dosage of the antipsychotic agent allows the beneficial regional modulation of D2 antagonism described above to take effect. While not being bound by any particular theory, it is believed that if the dosage of the antipsychotic agent is too high, resulting in high D2 antagonistic activity, then the regional modulation of D2 antagonism described above will not have a significant efficacious effect.

In some embodiments, the co-administration described herein eliminates or reduces the severity of one or more side effects caused by the antipsychotic when it is administered alone at an efficacious dose. In various embodiments, the side effects are selected from the group consisting of stroke, tremors, sedation, gastrointestinal problems, neurological problems, increased risk of death, cerebrovascular events, movement disorder, dystonia, akathisia, parkinsoniam movement disorder, tardive dyskinesia, cognitive disorders, prolactinemia, catalepsy, psychosis, neuroleptic malignant syndrome, heart problems, pulmonary problems, diabetes, liver failure, suicidality, sedation, orthostatic hypotension, choking, dizziness, tachycardia, blood abnormalities (including abnormal triglyceride levels, increased cholesterol levels, dyslipidemia, and hyperglycemia), syncope, seizures, dysphagia, priapism, thrombotic thrombocytopenic purpura, disruption of body temperature regulation, insomnia, agitation, anxiety, somnolence, aggressive reaction, headache, constipation, nausea, dyspepsia, vomiting, abdominal pain, saliva increase, toothache, rhinitis, coughing, sinusitis, pharyngitis, dyspnea, back pain, chest pain, fever, rash, dry skin, seborrhea, increased upper respiratory infection, abnormal vision, arthralgia, hypoaesthesia, manic reaction, concentration impairment, dry mouth, pain, fatigue, acne, pruritus, myalgia, skeletal pain, hypertension, diarrhea, confusion, asthenia, urinary incontinence, sleepiness, increased duration of sleep, accommodation disturbance, palpitations, erectile dysfunction, ejaculatory dysfunction, orgastic dysfunction, lassitude, increased pigmentation, increased appetite, automatism, increased dream activity, diminished sexual desire, nervousness, depression, apathy, catatonic reaction, euphoria, increased libido, amnesia, emotional liability, nightmares, delirium, yawning, dysarthria, vertigo, stupor, paraesthesia, aphasia, hypoesthesia, tongue paralysis, leg cramps, torticollis, hypotonia, coma, migrain, hyperreflexia, choreoathetosis, anorexia, flatulence, stomatitis, melena, hemorrhoids, gastritis, fecal incontinence, erutation, gastroeophageal reflux, gastroenteritis, esophagitis, tongue discoloration, choleithiasis, tongue edema, diverticulitis, gingivitis, discolored feces, gastrointestinal hemorrhage, hematemesis, edema, rigors, malaise, pallor, enlarged abdomen, ascites, sarcoidosis, flushing, hyperventilation, bronchospasm, pneumonia, tridor, asthma, increased sputum, aspiration, photosensitivity, increased sweating, acne, decreased sweating, alopecia, hyperkeratosis, skin exfoliation, bullous eruption, skin ulceration, aggravated psoriasis, furunculosis, verruca, dermatitis lichenoid, hypertrichosis, genital pruritus, urticaria, ventricular tachycardia, angina pectoris, premature atrial contractions, T wave inversion, ventricular extrasystoles, ST depression, AV block, myocarditis, abnormal accommodation, xerophthalmia, diplopia, eye pain, blepharitis, photopsia, photophobia, abnormal lacrimation, hyponatremia, creatine phosphokinase increase, thirst, weight decrease, decreased serum iron, cachexia, dehydration, hypokalemia, hypoproteinemia, hyperphosphatemia, hypertrigylceridemia, hyperuricemia, hypoglycemia, polyuria, polydipsia, hemturia, dysuria, urinary retention, cystitis, renal insufficiency, arthrosis, synostosis, bursitis, arthritis, menorrhagia, dry vagina, nonpeurperal lactation, amenorrhea, female breast pain, leukorrhea, mastitis, dysmenorrhea, female perineal pain, intermenstrual bleeding, vaginal hemorrhage, increased SGOT, increased SGPT, cholestatic hepatitis, cholecystitis, choleithiasis, hepatitis, hepatocellular damage, epistaxis, superficial phlebitis, thromboplebitis, thrombocytopenia, tinnitus, hyperacusis, decreased hearing, anemia, hypochromic anemia, normocytic anemia, granulocytopenia, leukocytosis, lymphadenopathy, leucopenia, Pelger-Huet anomaly, gynecomastia, male breast pain, antiduretic hormone disorder, bitter taste, micturition disturbances, oculogyric crisis, abnormal gait, involuntary muscle contraction, and increased injury. In one embodiment, the side effect is weight gain. In one embodiment, side effect is associated with administration of the antipsychotic to a child under 18. In one embodiment, the side effect in the child is selected from psychosis, schizophrenia, pervasive developmental disorder, autism, Tourette's syndrome, conduct disorder, aggression, attention and hyperactivity difficulties (e.g., ADD, ADHD). In some embodiments, the side effects of weight gain, heart rhythm problems, and diabetes are more severe in children.

In some embodiments, due to decreased side effects, the co-administration described herein can be used to increase patient compliance during antipsychotic therapy.

In some embodiments, the antipsychotic agent is administered at a sub-maximal level. In various such embodiments, the dosage of the antipsychotic agent is less than about 75%, 60%, 50%, 40%, 30%, 20%, or 10% of the maximal dose. By "maximal dose," it is meant the minimum dose where further increases in the dose do not result in any significant increase in therapeutic effect when administering the agent alone. In some embodiments, the antipsychotic agent is administered at a dose that is less than an efficacious dose for the antipsychotic when it is administered alone. In various embodiments, the dosage is less than about 75%, 60%, 50%, 40%, 30%, 20%, or 10% of an efficacious dose. By "efficacious dose," it is meant the minimal dosage that is required to achieve a clinically relevant therapeutic effect when administering the agent alone.

In some embodiments, co-administration of the 5-HT2A inverse agonist or antagonist with the antipsychotic agent results in a rapid onset of an efficacious effect. In other words, in some embodiments, efficacious activity is achieved faster than when the antipsychotic agent is administered alone. In various embodiments, the rapid onset of efficacious activity is demonstrated by a clinically relevant therapeutic effect being achieved greater than about 30%, 40%, 50%, 60%, 70%, 80%, 90%, 100%, 110%, 130%, 150%, 200%, 300%, 400%, or 500% faster than when the antipsychotic agent is administered alone at an efficacious dose. In some embodiments, the rapid onset of efficacious activity is demonstrated by a greater percentage of patients experiencing an efficacious effect after a specified period of time of therapy when compared to administration of the antipsychotic agent alone at an efficacious dose. In various embodiments, the percentage of patients experiencing an efficacious effect is increased by greater than about 20%, 30%, 40%, 50%, 60%, 70%, 80%, 90%, 100%, 110%, 130%, 150%, 200%, 300%, 400%, or 500% when compared to administration of the antipsychotic agent alone at an efficacious dose. In some embodiments, the specified period of time is two weeks.

In various embodiments, the co-administration of the 5-HT2A inverse agonist or antagonist with the antipsychotic agent is used to treat, prevent, or ameliorate the symptoms of a neuropsychiatric disorder, including but not limited to schizophrenia, schizoaffective disorders, mania, depression (including dysthymia, treatment-resistant depression, and depression associated with psychosis), cognitive disorders, aggressiveness (including impulsive aggression), panic attacks, obsessive compulsive disorders, borderline personality disorder, borderline disorder, multiplex developmental disorder (MDD), behavioral disorders (including behavioral disorders associated with age-related dementia), psychosis (including psychosis associated with dementia, psychosis associated with Parkinson's disease, psychosis associated with Alzheimer's disease, induced by treatment, such as treatment of Parkinson's disease, or associated with post traumatic stress disorder), suicidal tendency, bipolar disorder, sleep disorder (including sleep maintenance insomnia, chronic insomnia, transient insomnia, and periodic limb movements during sleep (PLMS)), addiction (including drug or alcohol addiction, opioid addiction, and nicotine addiction), attention deficit hyperactivity disorder (ADHD), post traumatic stress disorder (PTSD), Tourette's syndrome, anxiety (including general anxiety disorder (GAD)), autism, Down's syndrome, learning disorders, psychosomatic disorders, alcohol withdrawal, epilepsy, pain (including chronic pain, neuropathic pain, inflammatory pain, diabetic peripheral neuropathy, fibromyalgia, postherpetic neuralgia, and reflex sympathetic dystrophy), disorders associated with hypoglutamatergia (including schizophrenia, childhood autism, and dementia), and serotonin syndrome.

In some embodiments, the co-administration of the 5-HT2A inverse agonist or antagonist with the antipsychotic agent is used to treat, prevent, or ameliorate the symptoms of a neurodegenerative disorder, including but not limited to Alzheimer's disease, Parkinson's disease, Huntington's chorea, sphinocerebellar atrophy, frontotemporal dementia, supranuclear palsy, or Lewy body dementia.

In some embodiments, the co-administration of the 5-HT2A inverse agonist or antagonist with the antipsychotic agent is used to treat, prevent, or ameliorate the symptoms of an extrapyramidal disorder including, but not limited to, dyskinesias (such as induced by treatment of Parkinson's disease), bradykinesia, rigidity, psychomotor slowing, tics, akathisia (such as induced by a neuroleptic or SSRI agent), Friedrich's ataxia, Machado-Joseph's disease, dystonia, tremor, restless legs syndrome, or myoclonus.

In some embodiments, the co-administration of the 5-HT2A inverse agonist or antagonist with the antipsychotic agent is used to treat, prevent, or ameliorate the symptoms of chemotherapy-induced emesis, frailty, on/off phenomena, non-insulin-dependent diabetes mellitus, metabolic syndrome, autoimmune disorders (including lupus and multiple sclerosis), sepsis, increased intraocular pressure, glaucoma, retinal diseases (including age related macular degeneration), Charles Bonnet syndrome, substance abuse, sleep apnea, pancreatis, anorexia, bulimia, disorders associated with alcoholism, cerebral vascular accidents, amyotrophic lateral sclerosis, AIDS related dementia, traumatic brain or spinal injury, tinnitus, menopausal symptoms (such as hot flashes), sexual dysfunction (including female sexual dysfunction, female sexual arousal dysfunction, hypoactive sexual desire disorder, decreased libido, pain, aversion, female orgasmic disorder, and ejaculatory problems), low male fertility, low sperm motility, hair loss or thinning, incontinence, hemorrhoids, migraine, hypertension, thrombosis (including thrombosis associated with myocardial infarction, stroke, idiopathic thrombocytopenic purpura, thrombotic thrombocytopenic purpura, and peripheral vascular disease), abnormal hormonal activity (such as abnormal levels of ACTH, corticosterone, rennin, or prolactin), hormonal disorders (including Cushing's disease, Addison's disease, and hyperprolactinemia), a pituitary tumor (including a prolactinoma), a side effect associated with a pituitary tumor (including hyperprolactinemia, infertility, changes in menstruation, amenorrhea, galactorrhea, loss of libido, vaginal dryness, osteoporosis, impotence, headache, blindness, and double vision), vasospasm, ischemia, cardiac arrythmias, cardiac insufficiency, asthma, emphysema, or appetite disorders.

In some embodiments, the co-administration is used to treat, prevent, or ameliorate psychosis. Functional causes of the psychosis may include schizophrenia, Parkinson's disease, Alzheimer's disease, bipolar disorder, severe clinical depression, severe psychosocial stress, sleep deprivation, neurological disorders including brain tumor, dementia with Lewy bodies, multiple sclerosis, and sarcoidosis, electrolyte disorders including hypocalcemia, hypernatremia, hyonatremia, hyopkalemia, hypomagnesemia, hypermagnesemia, hypercalcemia, hypophosphatemia, and hypoglycemia, lupus, AIDS, leprosy, malaria, flu, mumps, psychoactive drug intoxication or withdrawal including alcohol, barbiturates, benzodizepeines, anticholinergics, atropine, scopolamine, Jimson weed, antihistamines, cocaine, amphetamines, and hallucinogens including cannabis, LSD, psilocybin, mescaline, MDMA, and PCP. Psychosis may include symptoms such as delusions, hallucinations, disorganized speech, disorganized behavior, gross distortion of reality, impaired mental capacity, impaired affective response, fluctuating level of consciousness, poor motor co-ordination, inability to perform simple mental tasks, disorientation as to person, place or time, confusion, or memory impairment. In one embodiment, the patient is experiencing acute exacerbation of psychosis. The rapid onset characteristics of certain combinations described herein are particularly advantageous in treating acute exacerbation of psychosis. In some embodiments, the combination is used to treat or ameliorate schizophrenia and specifically, psychosis associated with schizophrenia. In one embodiment, the patient has exhibited a prior response to antipsychotic therapy. In one embodiment, the patient exhibits a moderate degree of psychopathology.

In one embodiment, the co-administration is used to treat depression. In one embodiment, the co-administration results in a rapid onset of antidepressant activity as compared to the onset of activity observed with typical antidepressants (e.g., SSRIs). In various embodiments, efficacious antidepressant activity is achieved in less than about 8 weeks, 6 weeks, 4 weeks, or 2 weeks.

Many antipsychotic agents increase serum glucose levels. It has been surprisingly discovered that combination of a 5-HT2A inverse agonist with such an antipsychotic results in a decreased serum glucose elevation while maintaining efficacy. Accordingly, in various embodiments, the co-administration of the 5-HT2A inverse agonist or antagonist with the antipsychotic agent is used to prevent or reduce increased serum glucose associated with administration of the antipsychotic agent.

Many antipsychotic agents also cause weight gain. In some embodiments, the co-administration of the 5-HT2A inverse agonist or antagonist with the antipsychotic agent is used to prevent or reduce increased weight gain associated with administration of the antipsychotic agent.

In some embodiments, the 5-HT2A inverse agonist or antagonist is selective for the 5-HT2A receptor. By "selective," it is meant that an amount of the compound sufficient to effect the desired response from the 5-HT2A receptor has little or no effect upon the activity of other certain receptor types, subtypes, classes, or subclasses. In some embodiments, the 5-HT2A inverse agonist or antagonist does not interact strongly with other serotonin receptors (5-HT 1A, 1B, 1D, 1E, 1F, 2B, 2C, 4A, 6, and 7) at concentrations where the signaling of the 5-HT2A receptor is strongly or completely inhibited. In some embodiments, the 5-HT2A inverse agonist or antagonist is selective with respect to other monoamine-binding receptors, such as the dopaminergic, histaminergic, adrenergic and muscarinic receptors. In some embodiments, the 5-HT2A inverse agonist or antagonist has little or no activity at D2 receptors.

In various embodiments, the 5-HT2A inverse agonist or antagonist is selected from the group consisting of Adatanserin Hydrochloride, Altanserin Tartrate, Benanserin Hydrochloride, Blonanserin, Butanserin, Cinanserin Hydrochloride, Eplivanserin, Fananserin, Flibanserin, Glemanserin, Iferanserin, Ketanserin, Lidanserin, Mianserin Hydrochloride, Pelanserin Hydrochloride, Pruvanserin, Ritanserin, Seganserin, Tropanserin Hydrochloride, Iloperidone, Sertindole, EMR-62218, Org-5222, Zotepine, asenapine, ocaperidone, APD125, and AVE8488.

In some embodiments, the 5-HT2A inverse agonist or antagonist is selected from a compound disclosed in U.S. Pat. Nos. 6,756,393, 6,911,452; or 6,358,698 or U.S. Application Publication No. 2004-0106600, all of which are incorporated herein by reference in their entirety. In some embodiments, the 5-HT2A inverse agonist or antagonist is selected from one of the following structures or prodrugs, metabolites, hydrates, solvates, polymorphs, and pharmaceutically acceptable salts thereof:

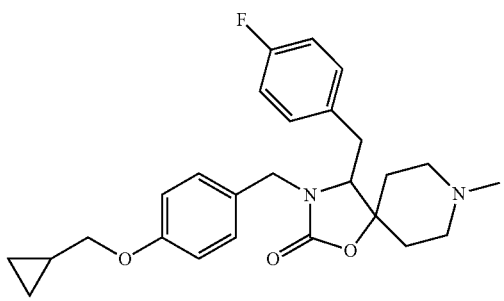

-continued

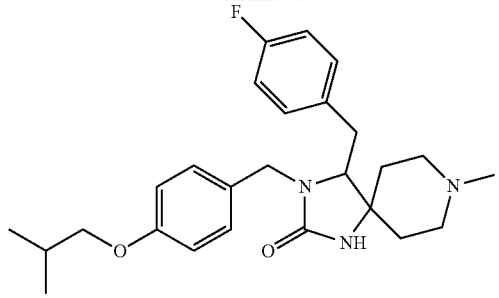

In one embodiment, the 5-HT2A inverse agonist or antagonist is pimavanserin or prodrugs, metabolites, hydrates, solvates, polymorphs, and pharmaceutically acceptable salts thereof. Pimavanserin, which is also known as N-(1-methylpiperidin-4-yl)-N-(4-fluorophenylmethyl)-N'-(4-(2-methylpropyloxy)phenylmethyl)carbamide, N-[(4-fluorophenyl)methyl]-N-(1-methyl-4-piperidinyl)-N'-[[4-(2-methylpropoxy)phenyl]methyl]-urea, 1-(4-fluorobenzyl)-1-(1-methylpiperidin-4-yl)-3-[4-(2-methylpropoxy)benzyl]urea, or ACP-103 has the structure of Formula (I):

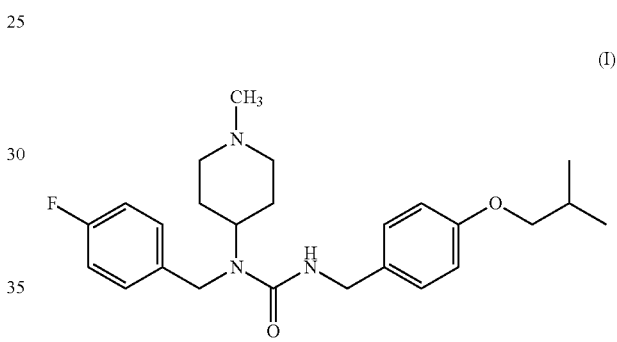

Pimavanserin can be obtained in a number of salts and crystalline forms. Exemplary salts include the tartrate, hemitartrate, citrate, fumarate, maleate, malate, phosphate, succinate, sulphate, and edisylate (ethanedisulfonate) salts. Pimavanserin salts including the aforementioned ions, among others, are described in U.S. Patent Publication No. 2006-0111399, filed Sep. 26, 2005 and entitled "SALTS OF N-(4-FLUOROBENZYL)-N-(1-METHYLPIPERIDIN-4-YL)-N'-(4-(2-METHYLPROPYLOXY)PHENYLMETHYL) CARBAMIDE AND THEIR PREPARATION," which is incorporated herein by reference in its entirety. Several crystalline forms of the tartrate salt are referred to as crystalline Form A, Form B, Form C, Form D, Form E and Form F, and are described in U.S. Patent Publication No. 2006-0106063, filed Sep. 26, 2006 and entitled "SYNTHESIS OF N-(4-FLUOROBENZYL)-N-(1-METHYLPIPERIDIN-4-YL)-N'-(4-(2-METHYLPROPYLOXY)PHENYLMETHYL) CARBAMIDE AND ITS TARTRATE SALT AND CRYSTALLINE FORMS," which is incorporated herein by reference in its entirety. In an embodiment, the crystalline form of the tartrate salt of pimavanserin is Form A. In another embodiment, the crystalline form of the tartrate salt of pimavanserin is Form C. Pimavanserin (including, for example, the tartrate salt) may be formulated into tablets, such as is described in more detail in U.S. Patent Publication Nos. 2007-0260064, filed May 15, 2007 and 2007-0264330, filed May 15, 2007, each entitled "PHARMACEUTICAL FORMULATIONS OF PIMAVANSERIN," which are incorporated herein by reference in their entireties.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

Metabolites include active species that are produced upon introduction of the parent compound into the biological milieu.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

Pimavanserin exhibits activity at monoamine receptors, specifically serotonin receptors and specifically acts as an inverse agonist at the 5-HT2A receptor. The compound shows high potency as an inverse agonist (and competitive antagonist) at the $5HT_{2A}$ receptor using a cell-based in vitro functional assay as well as using radioligand-binding assays. The compound exhibits lesser potency at 5-$HT_{2C}$ receptors as an inverse agonist (and competitive antagonist) using a cell-based functional assay and in radioligand-binding assays. The compound lacks activity at dopamine receptor subtypes. Unlike existing atypical antipsychotics, pimavanserin does not have significant potency for a variety of other targets that have been implicated in a range of dose-limiting side effects of the other antipsychotic drugs. For example, unlike clozapine and olanzapine, pimavanserin does not have significant activity at the muscarinic and histaminergic receptors that mediate sedation and potentially weight gain. The compound also lacks the alpha-adrenergic antagonist activities of clozapine, olanzapine, risperidone, and ziprasidone that may contribute to cardiovascular side effects. Further, the compound lacks potency at the $5HT_{2B}$ receptor that controls gastrointestinal function and myocardial development.

Pimavanserin is active in a number of models thought to be predictive of antipsychotic activity such as DOI ((±)-2,5-dimethoxy-4-iodoamphetamine, a serotonin agonist) induced head twitches in the rat and attenuation of hyperactivity in mice induced by the N-methyl-D-aspartate antagonist MK-801. The compound was effective in these models at oral doses of 3 and 10 mg/kg. In a rat model of deficits in sensory motor gating similar to those exhibited by schizophrenics, pimavanserin at doses of 1 and 3 mg/kg SC potently reversed the gating deficit induced by DOI. Pimavanserin also failed to disrupt learning of a simple auto-shaped response in mice at intraperitoneal doses up to 32 mg/kg. The pharmacological profile of pimavanserin suggests it will be effective as an antipsychotic agent without the side effects common to other compounds in this class. Thus, pimavanserin will have antipsychotic activity when used to treat schizophrenic subjects.

Pimavanserin may be synthesized by methods described below, or by modification of these methods. Ways of modifying the methodology include, among others, modification in temperature, solvent, reagents, etc.

The first step of the synthesis, illustrated below, is conducted in the presence of acetic acid, NaBH$_3$CN, and methanol to produce the compound of formula (II):

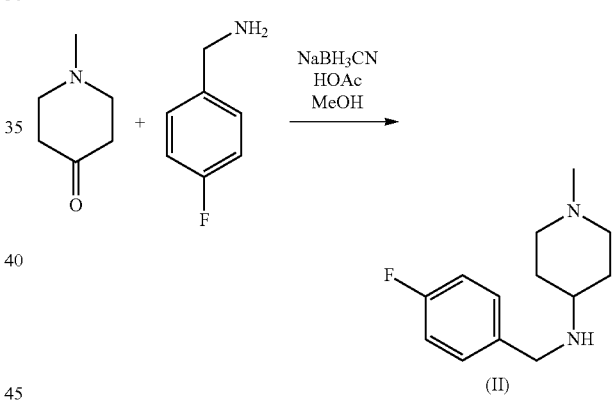

The compound of formula (IV) can be synthesized by treatment of the compound of formula (III) with isobutyl bromide and potassium carbonate in dimethyl formamide (DMF) at about 80° C.:

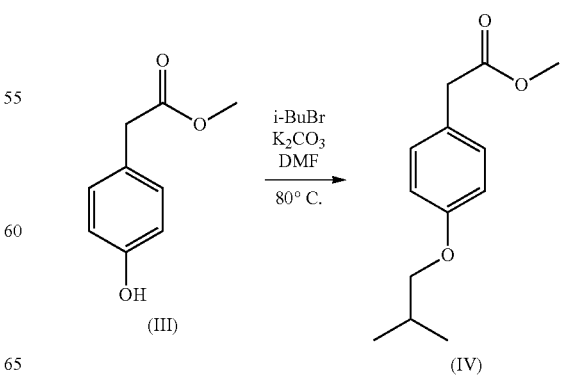

The compound of formula (IV) can be converted to the compound of formula (V) by reaction with potassium hydroide in methanol/water:

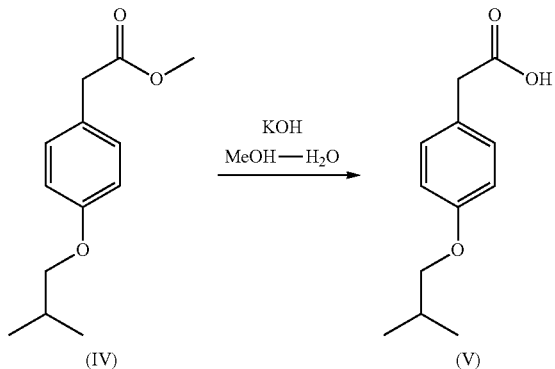

The compound of formula (V) is heated to reflux with diphenylphosphonyl azide (DPPA) and a proton sponge in tetrahydrofuran (THF) to produce the compound of formula (VI):

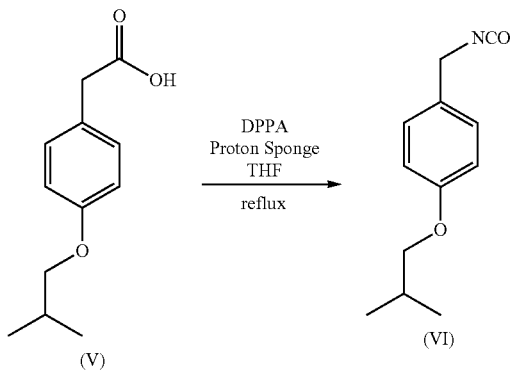

Finally, reaction of the compound of formula (II) with the compound of formula (VI) in methylene chloride produces the compound of formula (I):

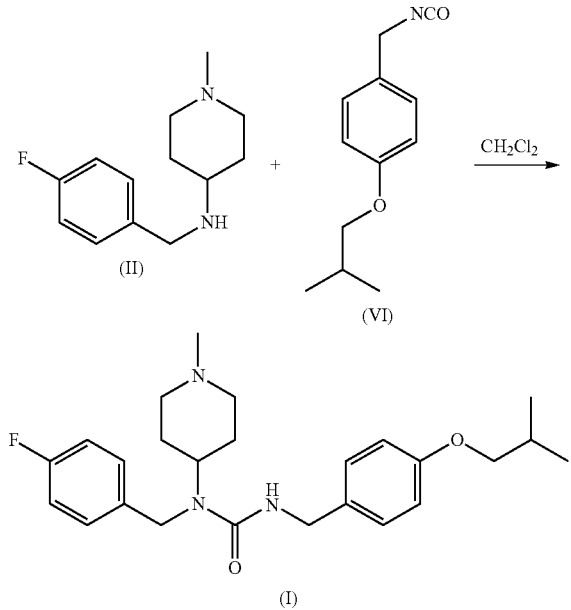

Non-limiting examples of suitable antipsychotic agents that may be co-administered with a 5-HT2A inverse agonist or antagonist include a phenothiazine, a phenylbutylpiperidine, a dibenzapine, a benzisoxidil, and a salt of lithium. In some embodiments, the phenothiazine is selected from the group consisting of chlorpromazine (Thorazine®), mesoridazine (Serentil®), prochlorperazine (Compazine®), thioridazine (Mellaril), Fluphenazine (Prolixin®), Perphenazine (Trilafon®), and Trifluoperazine (Stelazine®). In some embodiments, the phenylbutylpiperidine is selected from the group consisting of haloperidol (Haldol®) and pimozide (Orap®). In some embodiments, the dibenzapine is selected from the group consisting of clozapine (Clozaril®), loxapine (Loxitane®), olanzapine (Zyprexa®), and quetiapine (Seroquel®). In some embodiments, the benzisoxidil is selected from the group consisting of risperidone (Risperdal®) and ziprasidone (Geodon®). In some embodiments, the salt of lithium is lithium carbonate. In some embodiments, the antipsychotic agent is selected from the group consisting of Aripiprazole (Abilify®), Etrafon®, Droperidol (Inapsine®), Thioridazine (Mellaril®), Thiothixene (Navane®), Promethazine (Phenergan®), Metoclopramide (Reglan®), Chlorprothixene (Taractan®), Triavil®, Molindone (Moban®), Sertindole (Serlect®), Droperidol, Amisulpride (Solian®), Melperone, Paliperidone (Invega®), and Tetrabenazine. In some embodiments, the antipsychotic is a D2 antagonist. In some embodiments, the antipsychotic is a typical antipsychotic. In some embodiments, the antipsychotic is an atypical antipsychotic.

In one embodiment, the pimavanserin is co-administered with the antipsychotic haloperidol. In another embodiment, pimavanserin is co-administered with the antipsychotic risperidone. In various embodiments, the dose of haloperidol administered is less than about 0.5 mg, 1 mg, 2 mg, or 3 mg per day. In various embodiments, the dose of risperidone administered is less than about 0.5 mg, 1 mg, 2 mg, 3 mg, 4 mg, 5 mg, or 6 mg per day. In one embodiment, the dose of risperidone administered is about 2 mg per day. In various embodiments, the dose of pimavanserin administered is from about 10 mg to about 15 mg, from about 15 mg to about 20 mg, from about 20 mg to about 25 mg, from about 25 mg to about 30 mg, from about 30 mg to about 40 mg, from about 40 mg to about 50 mg, from about 50 mg to about 60 mg, from about 60 mg to about 70 mg, or from about 70 mg to about 80 mg per day. In one embodiment, the dose of pimavanserin is about 20 mg per day.

Some embodiments include a pharmaceutical composition comprising both a 5-HT2A inverse agonist or antagonist and the antipsychotic agent in a single dosage form. Such pharmaceutical compositions may comprise physiologically acceptable surface active agents, carriers, diluents, excipients, smoothing agents, suspension agents, film forming substances, and coating assistants, or a combinations thereof. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

Techniques for formulation and administration of the compositions described herein may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use as described herein thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose. lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2): 101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation me incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

In some embodiments, the 5-HT2A inverse agonist or antagonist is long acting while the co-administered antipsychotic is short acting. The long acting or short acting properties may be due to long and short half lives, respectively. Many antipsychotics have relatively short occupancy times at D2 receptors. If a similarly short acting 5-HT2A inverse agonist or antagonist were used in combination with such antipsychotics, then the modulating effect of the 5-HT2A inverse agonist or antagonist on D2 activity would be diminished at the same time that D2 receptor occupancy is low, potentially resulting in a loss of efficacy, a problem that is compounded if a low dose of antipsychotic is used. In contrast, while not being bound by any particular theory, if a 5-HT2A inverse agonist or antagonist that has relatively long receptor occupancy compared to the antipsychotic is used, then high 5-HT2A receptor occupancy and resulting D2 modulating effect is maintained during the periods when the D2 receptor occupancy is at its lowest.

The benefits of combining a longer acting drug that improves the therapeutic window of a shorter acting therapeutic agent is also applicable to combinations other than 5-HT2A inverse agonists or antagonists with D2 antagonists. For example, while not being bound by any particular theory, it is believed that the efficacy of many drugs is limited to a range of drug levels (therapeutic window). FIG. 1A is an illustrative graph of the drug level upon sequential administration of a single drug. The therapeutic window (shown as the shaded region on the graph) is bounded on the lower side by the minimum level of the drug that must be present to achieve a therapeutic benefit and on the higher side by the level of the drug such that the toxicity would outweigh any therapeutic benefit above this plasma concentration of the drug. As illustrated for some drugs with a narrow therapeutic window, even the optimal dose results in plasma levels outside both the upper and lower bounds of the therapeutic window (the drug has toxicity limited efficacy). That is, while not being bound to any particular theory, it is believed that because the drug causes toxicity when the drug level reaches a particular concentration, the maximum dosage that can be administered is limited. Thus, during a period of successive dosings of a drug administered alone with a given half-life, the level of the drug can cycle in and out of the therapeutic window such that between doses, the drug levels can fall below those levels required for efficacy of the drug.

Figure 1B:
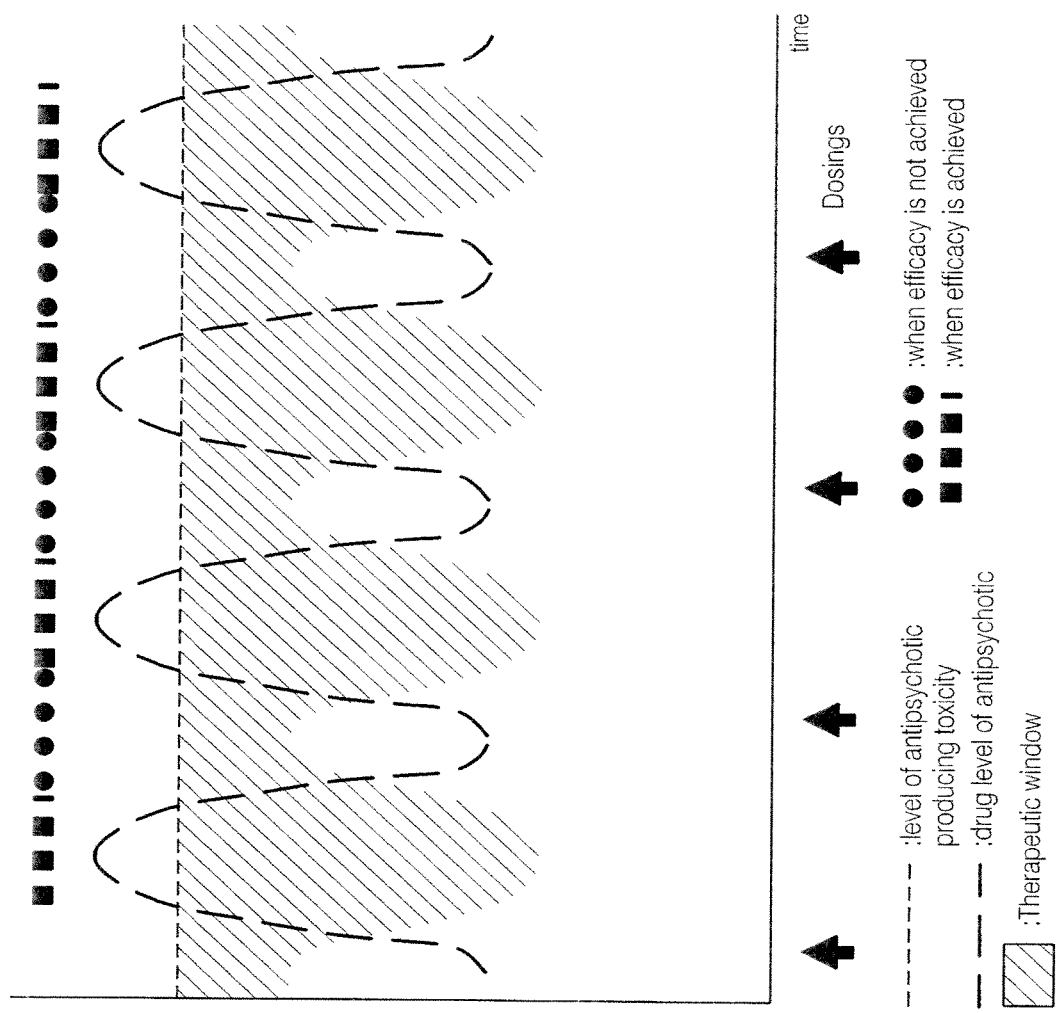
FIG. 1B is a graph depicting the drug level and therapeutic window for co-administration of two drugs having similar half lives.

While not being bound to any particular theory, it is believed that a secondary drug that, by lowering the plasma level associated with efficacy, can increase the therapeutic window for the primary drug. However, if the half life of the secondary drug is short, then the beneficial effects on the therapeutic window will be transient and will be absent at the time when the drug levels of the primary agent are lowest. Thus the beneficial effects of the modulatory agent may not be apparent. FIG. 1B illustrates the widening of the therapeutic window in the case where the primary and secondary drugs have similar half-lives. Only the drug level of the primary drug is depicted. FIG. 1B illustrates that, although the size of the therapeutic window is increased, the time that the primary drug is within the therapeutic window is not significantly increased compared to the primary drug administered alone (see FIG. 1A). For example, if the primary drug is a D2 receptor antagonist and the secondary drug is a 5-HT2A inverse agonist or antagonist, it is believed that the 5-HT2A antagonist or inverse agonist would increase the therapeutic window for the D2 antagonist when the level of the secondary drug exceeds its own required level of efficacy. While the secondary drug lowers the required level of the primary drug, it does so when the levels of the primary drug are already high. Consequently, it is believed that the fraction of time in which there is efficacious therapy may not be increased through this approach.

Figure 1C:
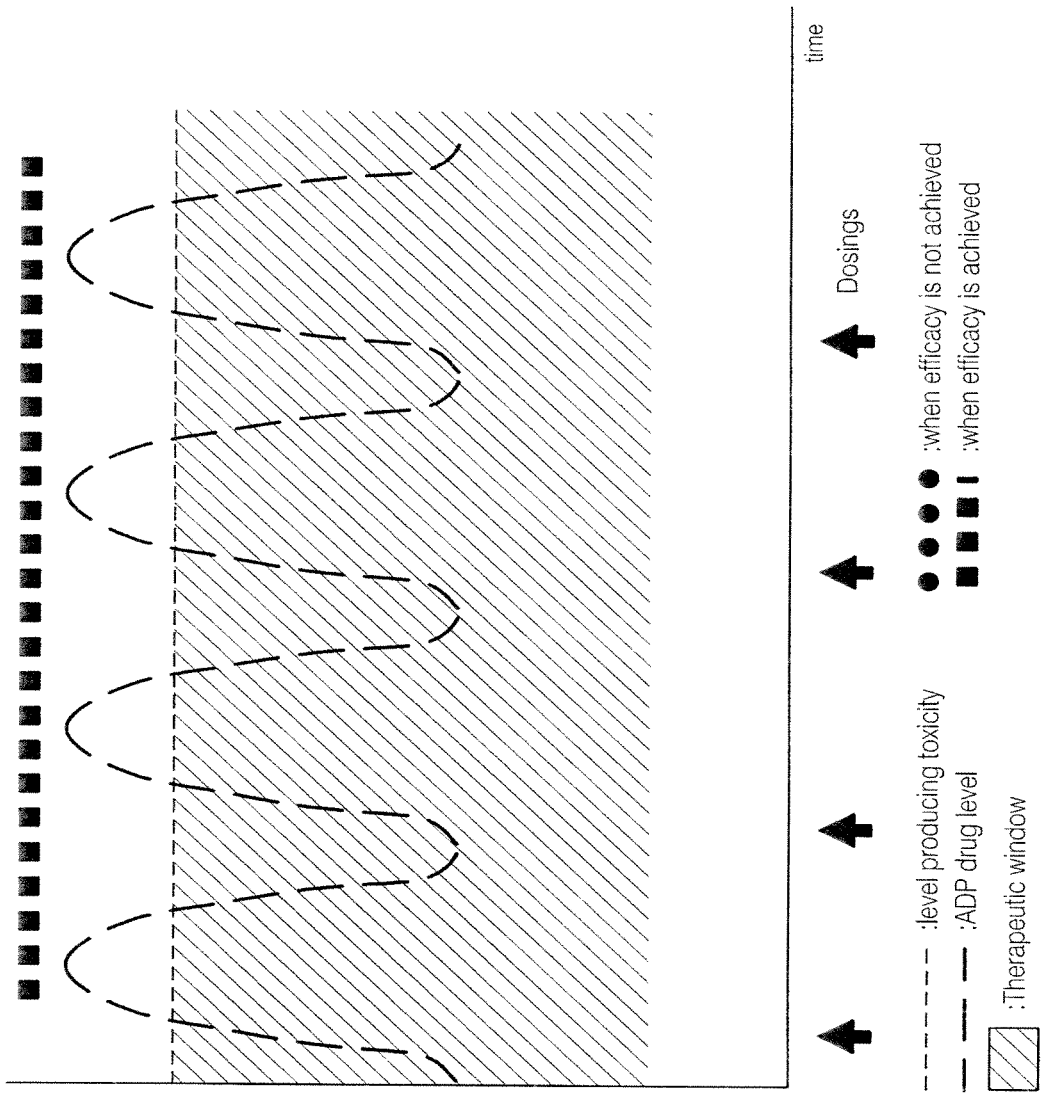
FIG. 1C is a graph depicting the drug level and therapeutic window for co-administration of two drugs have different half lives.

While not being bound to any particular theory, it is believed that when a secondary drug has a longer half-life than the primary drug, the enhanced therapeutic window can be maintained into the next dose. FIG. 1C depicts the resulting sustained increase in the therapeutic window. Because the secondary drug is present at high levels throughout each dosing period of the primary drug, the lower limit of the therapeutic window stays consistently low. Thus, the primary drug is always within the therapeutic window, thereby dramatically increasing the fraction of time in which there is efficacious therapy. Implicit in this is the opportunity to lower the dose of the primary drug to a level that diminishes its toxic effects while maintaining its efficacy.

Accordingly, some embodiments include administering a first agent in combination with a second agent wherein the first agent has a higher half-life than the second agent. In some embodiments, the half-life of the first agent is at least about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, or more than 4.0 times higher than the half-life of the second agent. In some embodiments, the first agent modulates the activity of the second agent. In some embodiments, the first and second agents are selected such that their relative half-lives and the modulating effect of the first agent on the second agent results in the second agent being present at an efficacious dose during at least about 50%, 60%, 70%, 80%, 90%, or 100% of the time between successive dosing of the second agent.

Some embodiments include selecting appropriate pharmaceutical agents to achieve the results indicated above. Some such embodiments include determining whether a first pharmaceutical agent modulates a pharmacological property of a second pharmaceutical agent, such as by in vitro assays or in vivo measurements. In one embodiment, the pharmacological property that is modulated is a receptor occupancy. For example, the first pharmaceutical agent may decrease or increase the occupancy of a particular receptor. In one embodiment, the pharmacological property is the minimum dose at which the second pharmaceutical agent has an efficacious effect. For example, the first pharmaceutical agent may decrease the minimum efficacious dose of the second pharmaceutical agent. Some embodiments further include determining whether the first pharmaceutical agent has a longer half-life than a second pharmaceutical agent.

In some embodiments, the first agent has D2 antagonist activity (e.g., haloperidol or risperidone). In some embodiments, the second agent is a 5-HT2A inverse agonist or antagonist. For example, in some embodiments, the second agent is pimavanserin or any of the 5-HT2A inverse agonists or antagonists described herein.

EXAMPLES

Example 1

Haloperidol and Risperidone Combinations Administered to Schizophrenic Patients

A randomized, double blind, multi-center study of schizophrenic subjects with an acute exacerbation of psychosis was conducted. Subjects with a DSM-IV diagnosis of schizophrenia and a baseline score on the Positive and Negative Syndrome Scale (PANSS) of at least 65 (high level of psychopathology), and a score of 4 or higher on two items of the psychosis subscale were enrolled. Subjects were randomly assigned to be administered haloperidol 2 mg per day co-administered with placebo, haloperidol 2 mg per day co-administered with pimavanserin at 20 mg per day, 2 mg risperidone per day co-administered with a placebo, 2 mg risperidone per day co-administered with 20 mg of pimavanserin, or 6 mg risperidone per day co-administered with placebo. Subjects administered 2 mg of risperidone per day received two doses of 1 mg each. Subjects administered 6 mg of risperidone per day received two doses of 3 mg each. This study lasted approximately nine weeks and included a screening period to allow for wash out of prior antipsychotics (2 to 14 days) followed by six weeks of active fixed dosing. Subjects were returned to the clinic two weeks later for a follow up visit. Subjects were treated as in-patients during screening and for the first 14 days of the trial, and thereafter, at the discretion of each principal investigator (PI), completed the trial as outpatients. Subjects were evaluated at screening, after a drug-free lead-in period (Baseline Day −1), and periodically thereafter by the PANSS, the Clinical Global Impression Scale-Severity (CGI-S), the Calgary Depression Scale for Schizophrenia (CDSS), the Simpson and Angus Scale (SAS), and the Barnes Akathisia Scale (BAS).

Male and female subjects, age inclusive from 18-65, with a clinical diagnosis of schizophrenia (DSM-IV 295.XX), are enrolled. Subjects are experiencing an acute psychotic exacerbation, and have at least a moderate degree of psychopathology (total score on the PANSS of 65 or greater), and a score greater than or equal to 4 on two of the four following PANSS items: delusions, hallucinatory behavior, conceptual disorganization or suspiciousness, where at least one of the two items must be delusions or hallucinatory behavior. Subjects have a history of a previous psychotic exacerbation with a positive response to antipsychotic therapy, and a history of at least 3 months of prior antipsychotic therapy. In other words, subjects who have a history of being refractory to antipsychotic therapies, or are experiencing their first episode of psychosis, are excluded.

All subjects received twice daily (BID) oral doses of study medication. Subjects receiving haloperidol received a total of 2 mg per day in a single am dose followed by a placebo pm dose. Subjects administered 2 mg of risperidone per day received two doses of 1 mg each. Subjects administered 6 mg of risperidone per day received two doses of 3 mg each. Subjects administered pimavanserin received a total of 20 mg per day in a single am dose followed by a placebo pm dose. Thus each subject received BID dosing of study medications in a blinded manner.

Subjects were evaluated at baseline/enrollment (Study Day −1), and periodically thereafter throughout the active dosing portion of the trial (Study Days 1, 8, 15, 22, 29, 36, and 43). These clinical evaluations included vital signs, medical history and exam (including psychiatric and brief neurological evaluation), ECG measurements, the administration of clinical rating scales, safety evaluations including reported or observed adverse events, clinical chemistries (except Days 1, 22 and 36), and plasma sampling for the pimavanserin, haloperidol, and risperidone concentrations. A final follow-up visit on Day 57, two weeks after the termination of the active dosing portion of the trial, included a medical evaluation, safety clinical labs, and plasma sampling for pimavanserin, haloperidol, and risperidone concentrations. Prolactin levels, weight gain, and glucose levels were also monitored.

The clinical rating scale for psychosis and negative symptoms is the Positive and Negative Symptom Scale (PANSS). The Clinical Global Impression Scale (CGI-S) is a global assessment of clinical severity. Scales for extrapyramidal symptoms (EPS) include the Simpson and Angus Scale (SAS) and the Barnes Akathisia Scale (BAS). Finally, the Calgary Depression Scale for Schizophrenia (CDSS) was included.

The PANSS is a 30-item, 7-point rating system that was adapted from the Brief Psychiatric Rating Scale. It has sections that specifically measure positive symptoms, negative symptoms, and general psychopathology in schizophrenic subjects. The PANSS is widely used in trials of antipsychotic drug treatment, and has been formally validated for such use. The entire scale was administered at screening, at baseline (Study Day −1), and during each clinical evaluation except for Study Day 1 and Day 57.

The CGI-S consists of three subscales. The CGI-S (severity of illness) has been designed to evaluate global severity of illness. The CGI-S was administered at baseline (Study Day −1), and at each clinical evaluation, except for Study Days 1 and 57.

The SAS is an extrapyramidal motor effect measure. This 10-item, 5-point scale is designed to assess a range of extrapyramidal symptoms including disturbances in gait, muscle tone, and tremor. This scale was administered at baseline (Study Day −1), and at all clinical evaluations, except for Study Day 57.

The BAS is another extrapyramidal motor effect measure. The BAS was designed to measure drug-induced akathisia that occurs specifically with use of antipsychotic agents. The BAS is a four-item fully anchored scale. Three items (i.e., objective akathisia, subjective awareness of restlessness, and subjective distress related to restlessness) are rated on a 4-point scale, and the global clinical assessment of akathisia uses a 6-point scale. This scale was administered at baseline (Study Day −1), and at all clinical evaluations, except for Study Day 57.

The effect of adjunctive pimavanserin treatment on affective symptoms was also assessed. The CDSS is a 9-item, 4-point scale that was specifically designed to measure depressive symptoms in psychotic subjects, separate from the positive, negative, and extrapyramidal symptoms observed in this population. It has been widely used in treatment trials in schizophrenia and has been validated for such use. This scale was administered at screening and at all clinical evaluations, except for Study Days 1 and 57.

During the screening period (from screening to Study Day −1), all subjects receive only permitted concomitant medication as deemed necessary. All prior antipsychotic, mood stabilization and antidepressant therapy are completely washed out at least two days prior to randomization (Day −1). Thereafter, all investigational study drugs are administered twice a day for the duration of the trial.

Figure 2:
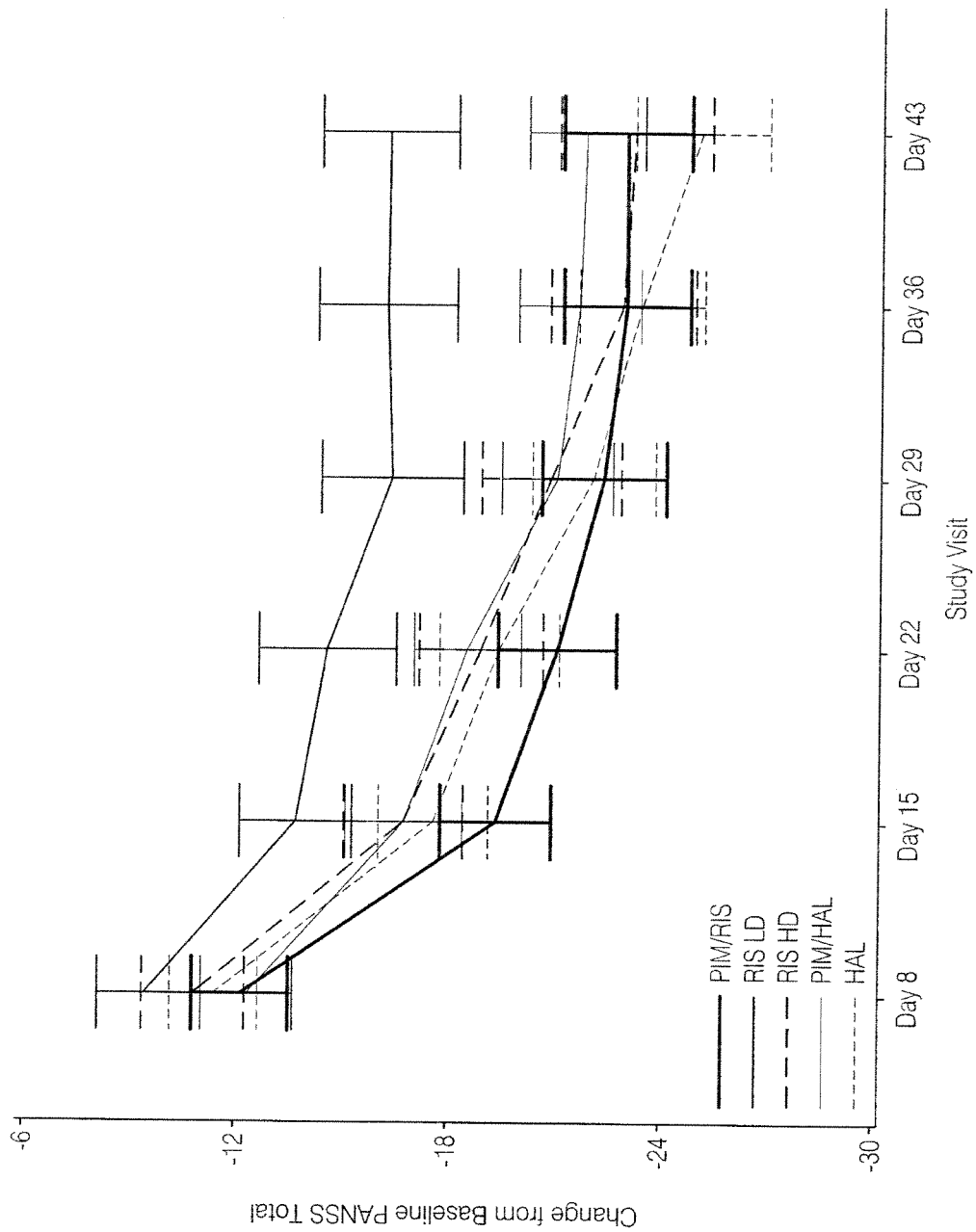
FIG. 2 is a graph depicting change in PANSS score upon administration of risperidone and haloperidol alone and in combination with pimavanserin.
Figure 3A:
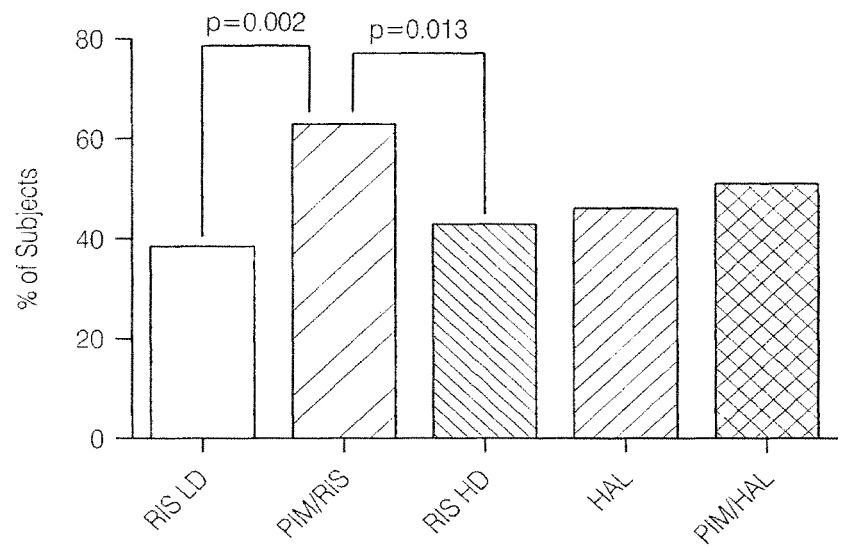
FIGS. 3A and 3B are bar graphs depicting the percent of responders to therapy with risperidone and haloperidol alone and in combination with pimavanserin at Day 15 and Day 43, respectively.
Figure 3B:
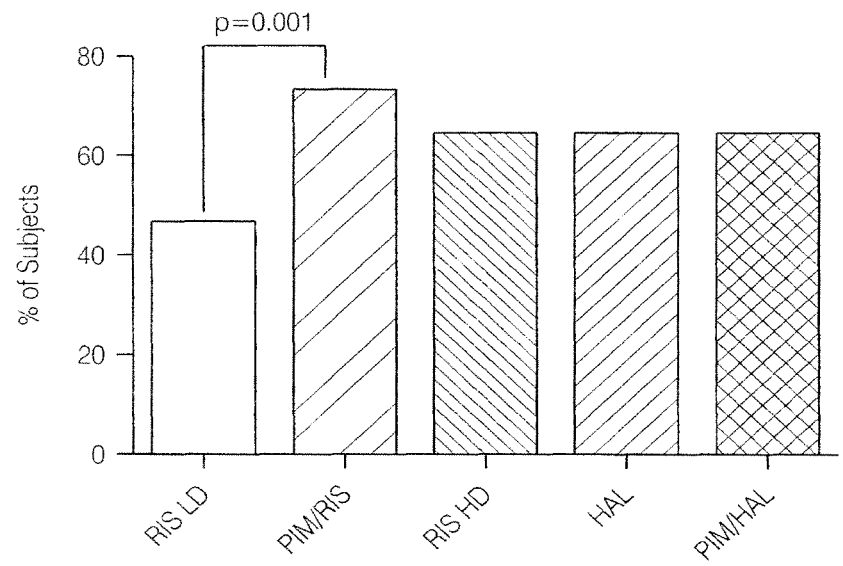

FIG. 2 is a graph depicting the total change (mean±SE) from baseline in the PANSS score for each treatment group. The pimavanserin/risperidone combination produced a significantly greater decrease in PANSS score starting at Day 15 as compared to low dose risperidone (2 mg). FIG. 3A is a bar graph depicting the percent of subjects with greater than or equal to 20% improvement in PANSS total at Day 15. FIG. 3B shows the same data at Day 43. The response to the pimavanserin/risperidone was significantly greater than low dose (2 mg) and high dose (6 mg) risperidone at Day 15 (p=0.002 and 0.013, respectively), and significantly greater than low dose risperidone at Day 43 (p=0.001).

Figure 4A:
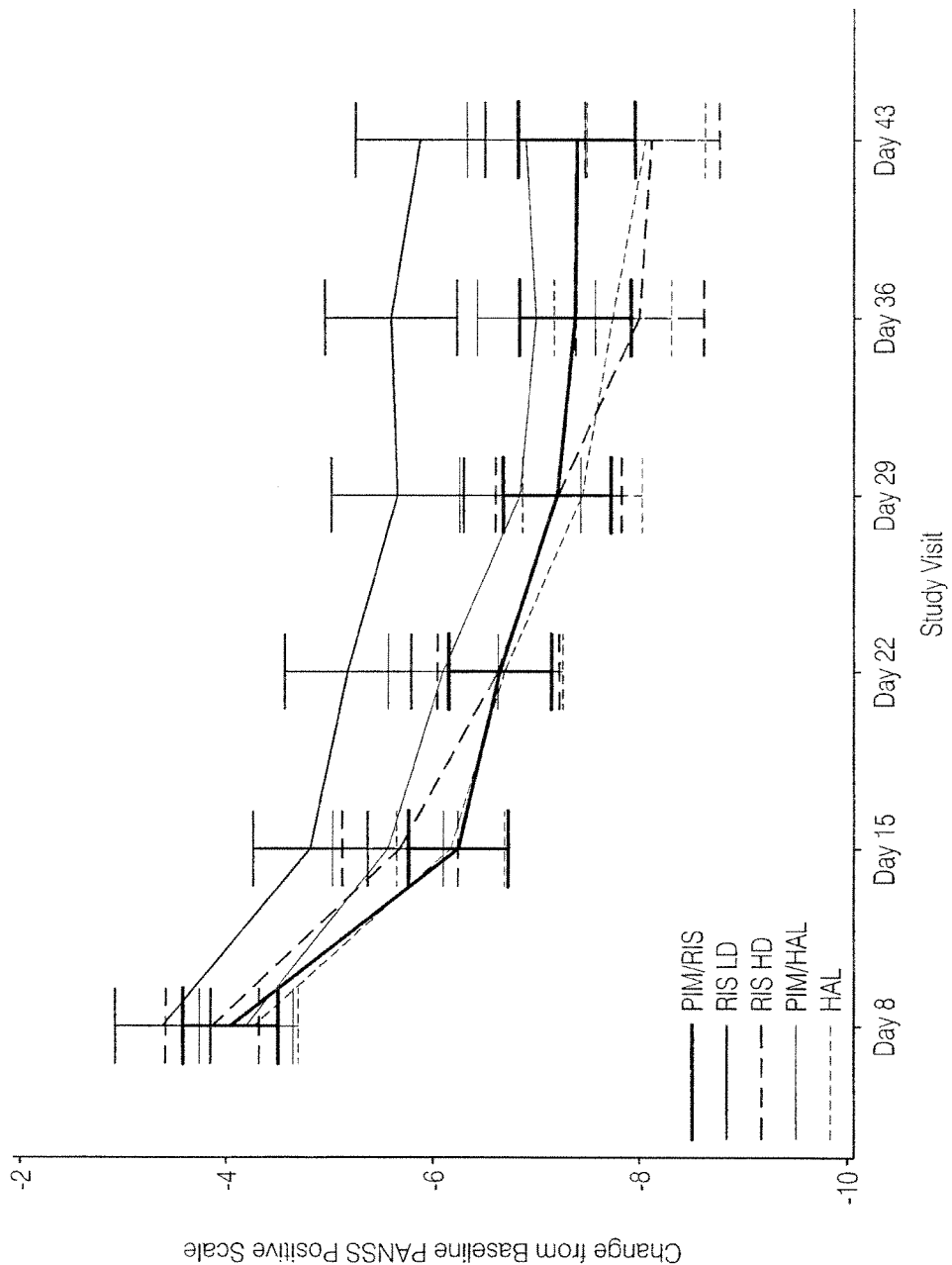
FIGS. 4A and 4B are graphs depicting change in PANSS positive and negative scales, respectively, upon administration of risperidone and haloperidol alone and in combination with pimavanserin.
Figure 4B:
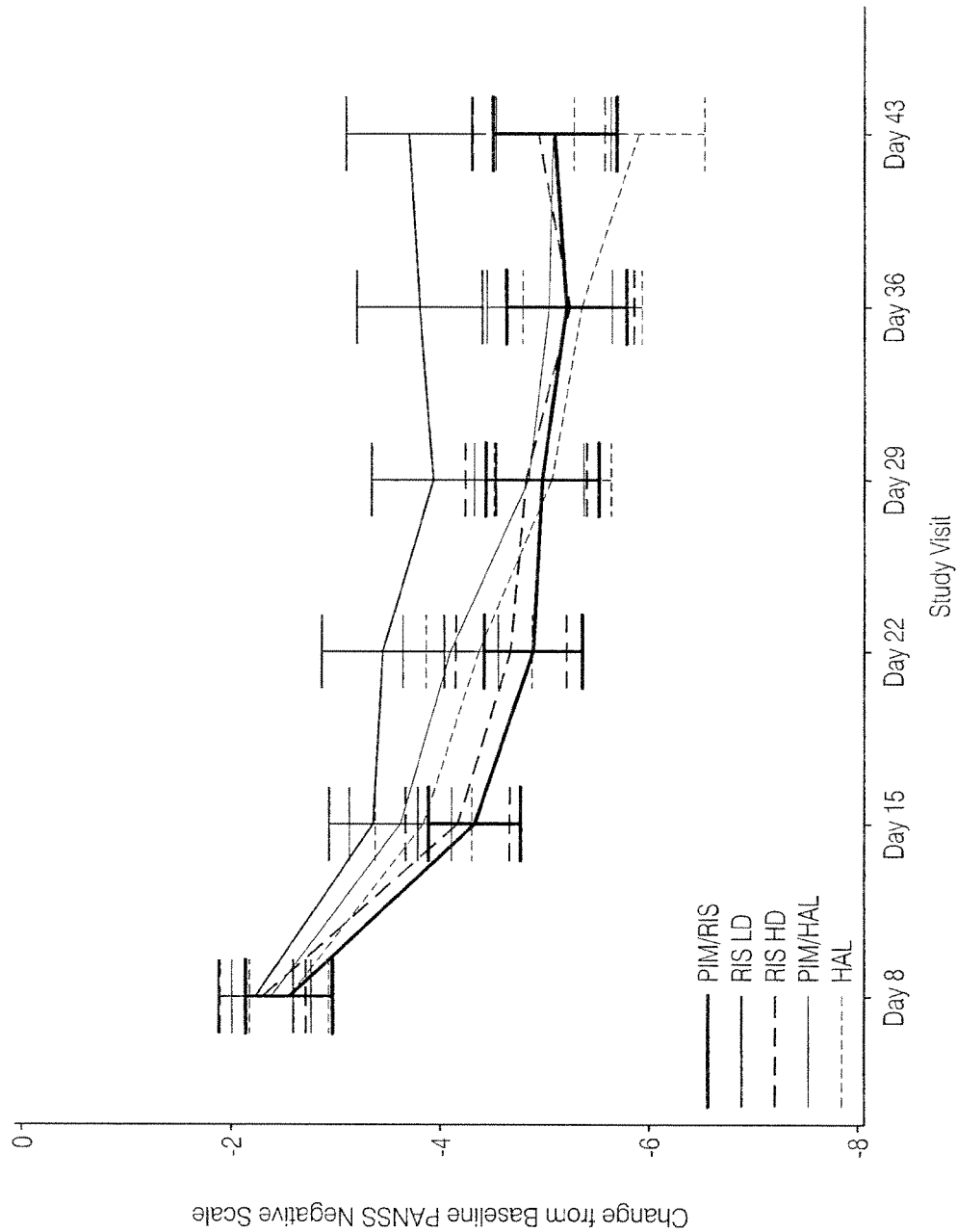

FIG. 4A is a graph depicting the change from baseline (mean±SE) in the PANSS positive symptom scale. The response to the pimavanserin/risperidone combination was significantly greater than low dose risperidone at Days 15-36 (p<0.05). The combination was not significantly different from high dose risperidone. FIG. 4B shows the change in the PANSS negative symptom scale. The response to the pimavanserin/risperidone combination was significantly greater than low dose risperidone at Day 15 and later (p<0.05). The combination was not significantly different from high dose risperidone.

Figure 5A:
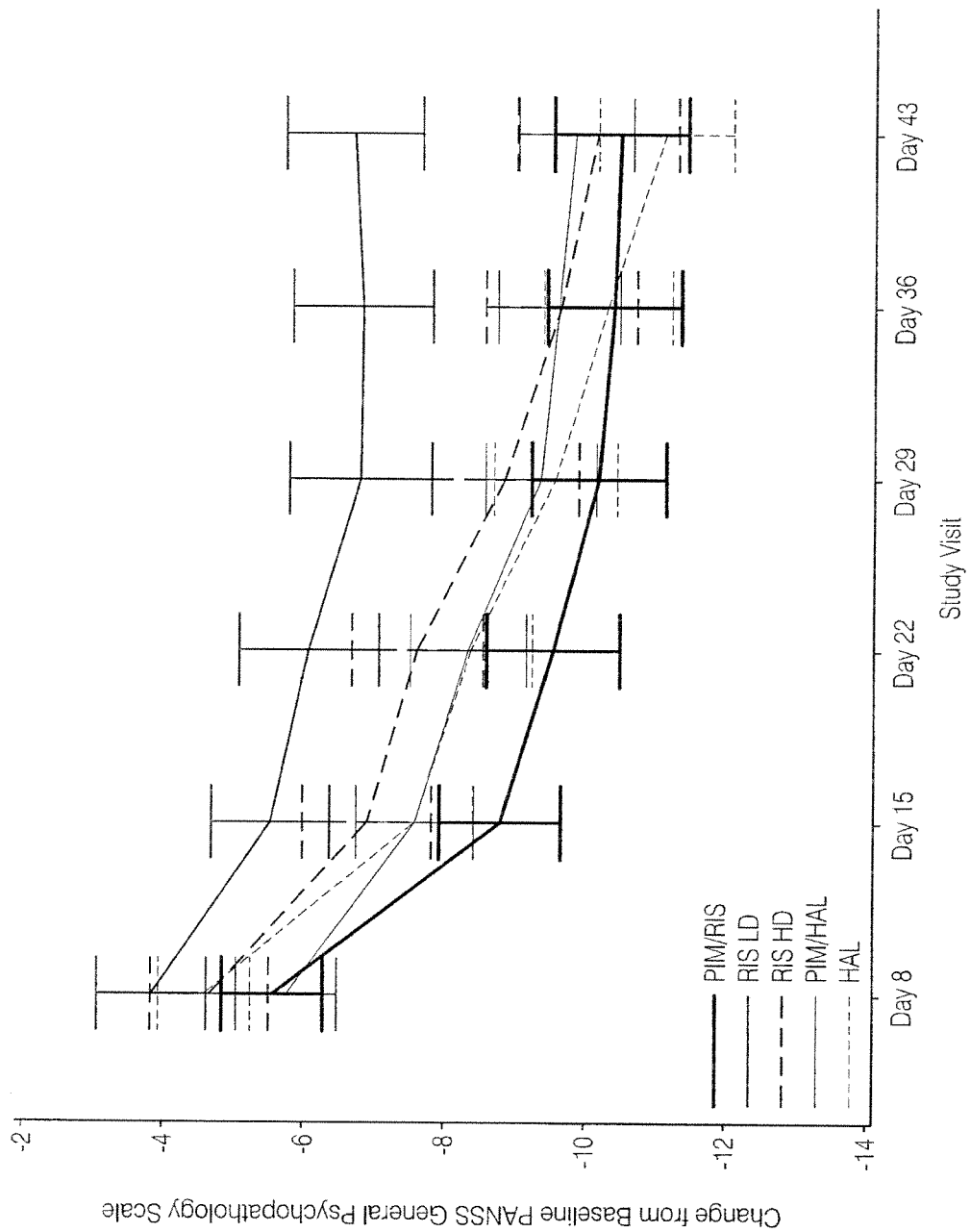
FIGS. 5A and 5B are graphs depicting change in PANSS psychopathology and cognition scales, respectively, upon administration of risperidone and haloperidol alone and in combination with pimavanserin.
Figure 5B:
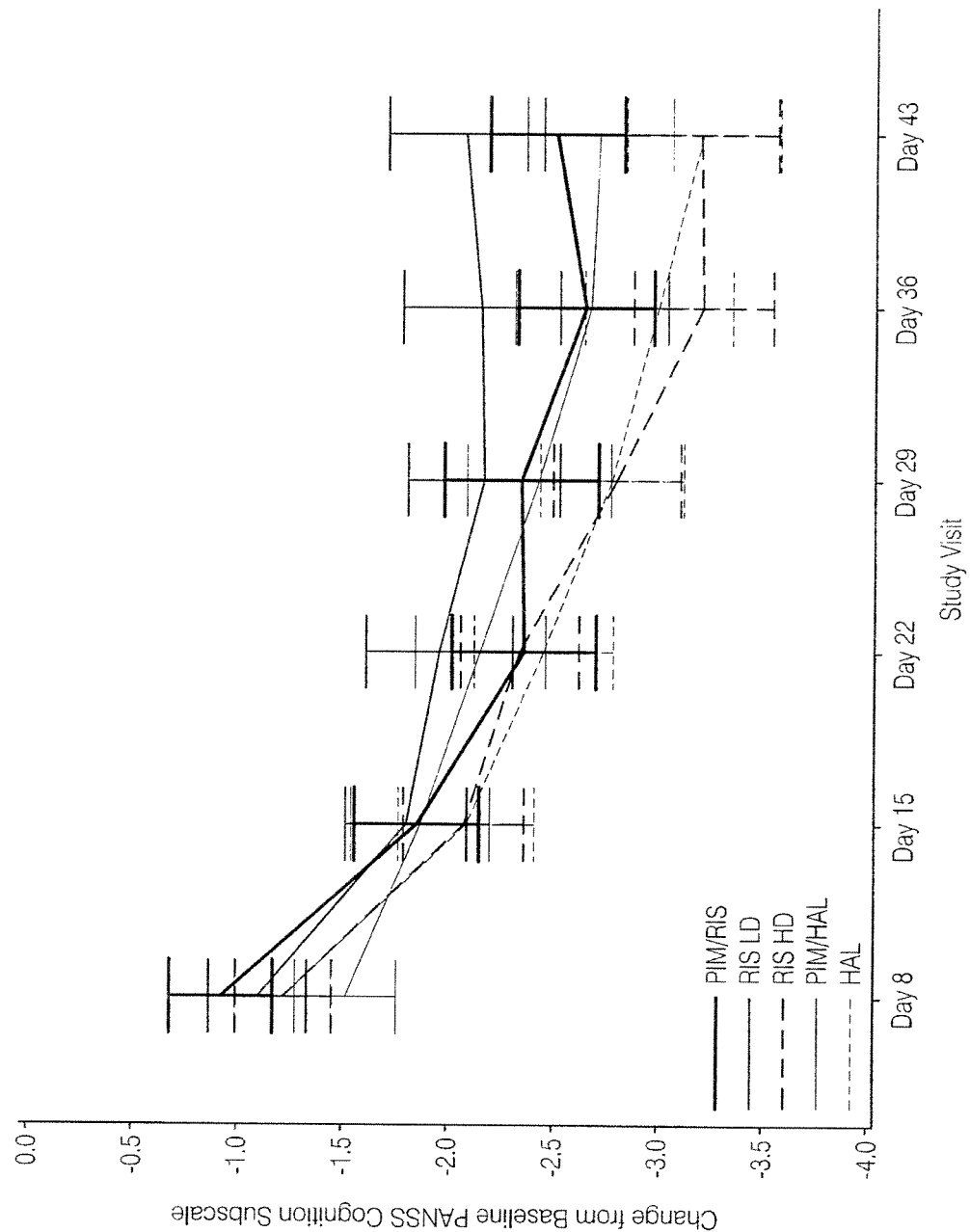

FIG. 5A is a graph depicting the change from baseline (mean±SE) in the PANSS general psychopathology scale. The response to the pimavanserin/risperidone combination was significantly greater than low dose risperidone for all time points from Day 15 on (p<0.005). The combination also showed trends for greater change compared to high dose risperidone at Days 15 and 20. FIG. 5B shows the change in the PANSS cognition scale. The response for the pimavanserin/risperidone combination was significantly better than low dose risperidone at Day 36 (p<0.05) and trends for superiority at Days 22 (p<0.05) and 43 (p<0.07).

Figure 6:
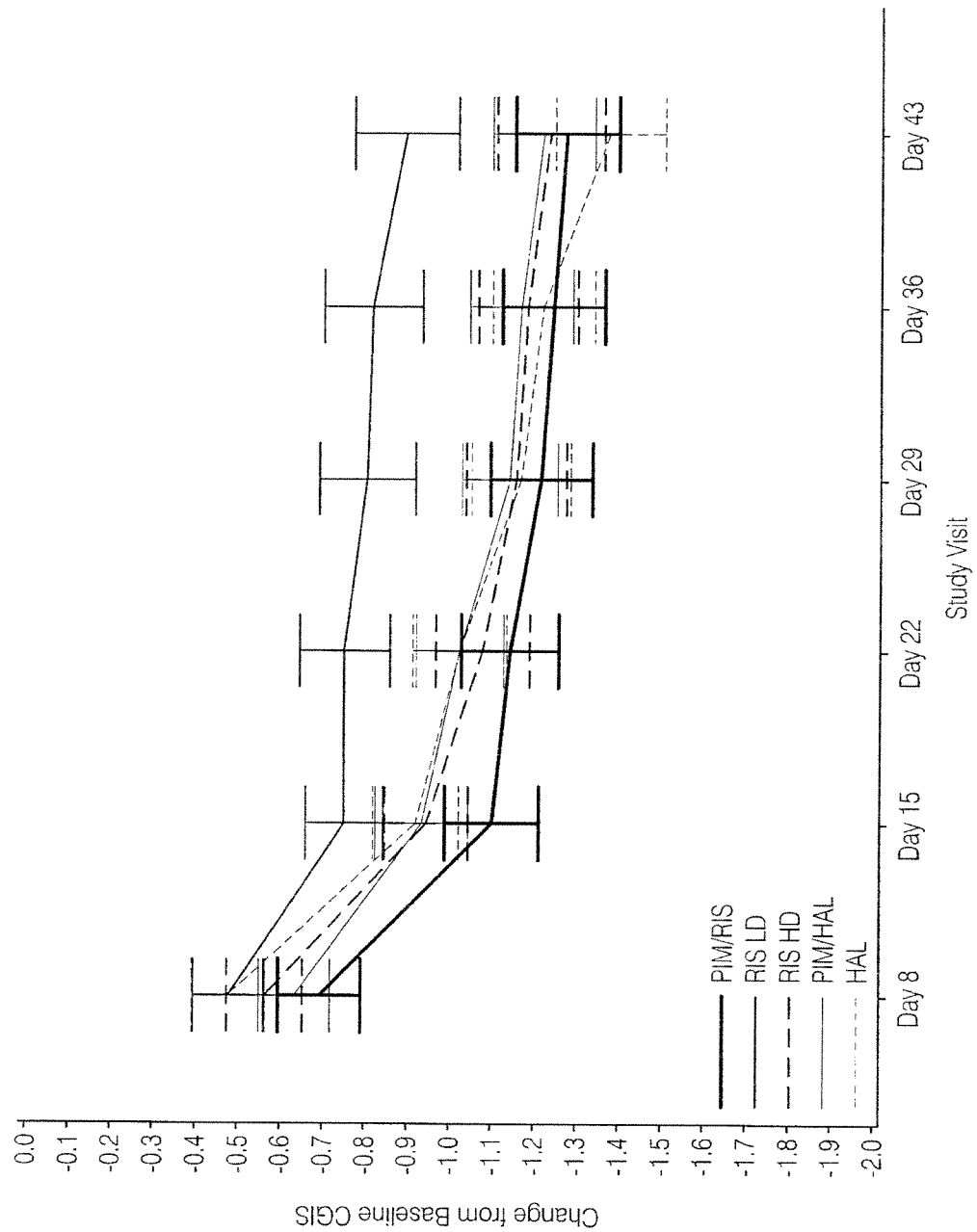
FIG. 6 is a graph depicting change in the CGI-severity scale upon administration of risperidone and haloperidol alone and in combination with pimavanserin.

FIG. 6 is a graph depicting the change from baseline (mean±SE) for the CGI-severity scale. The change for the pimavanserin/risperidone combination was significantly different from low dose risperidone from Day 15-43. No significant difference was observed between the combination and high dose risperidone.

Figure 7A:
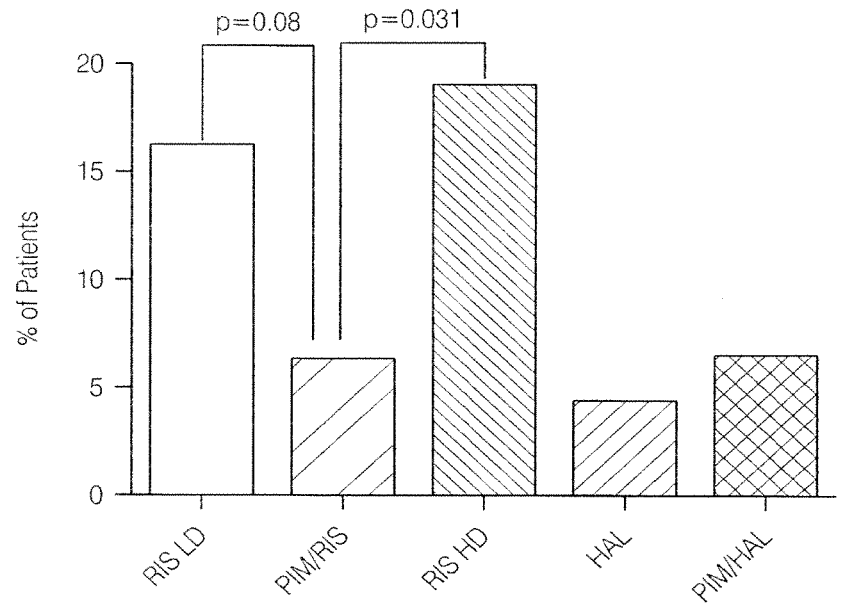
FIG. 7A is a bar graph depicting the percent of subjects experiencing weight gain upon administration of risperidone and haloperidol alone and in combination with pimavanserin.
Figure 7B:
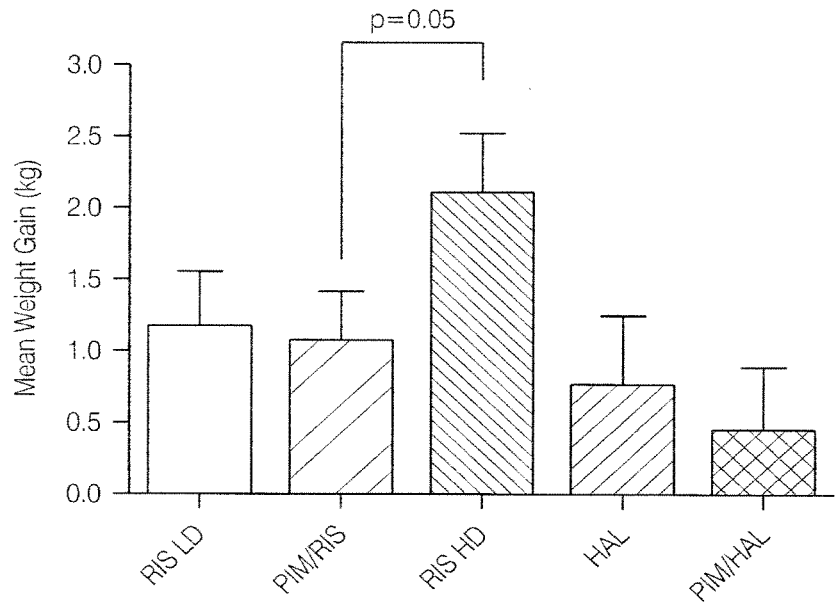
FIG. 7B is a bar graph depicting the mean weight gain in subjects upon administration of risperidone and haloperidol alone and in combination with pimavanserin.

FIG. 7A is a bar graph depicting the percent of subjects with a weight gain of at least 7% at the end of the study. The results indicate that fewer patients experienced clinically significant weight gain when receiving the pimavanserin/risperidone combination as compared to patients receiving either low dose (p=0.08) or high dose (p=0.031) of risperidone alone. FIG. 7B is a bar graph depicting mean weight gain at the end of the study compared to baseline. Patients receiving a pimavanserin/risperidone combination had less weight gain than high dose risperidone (p=0.05).

Figure 8A:
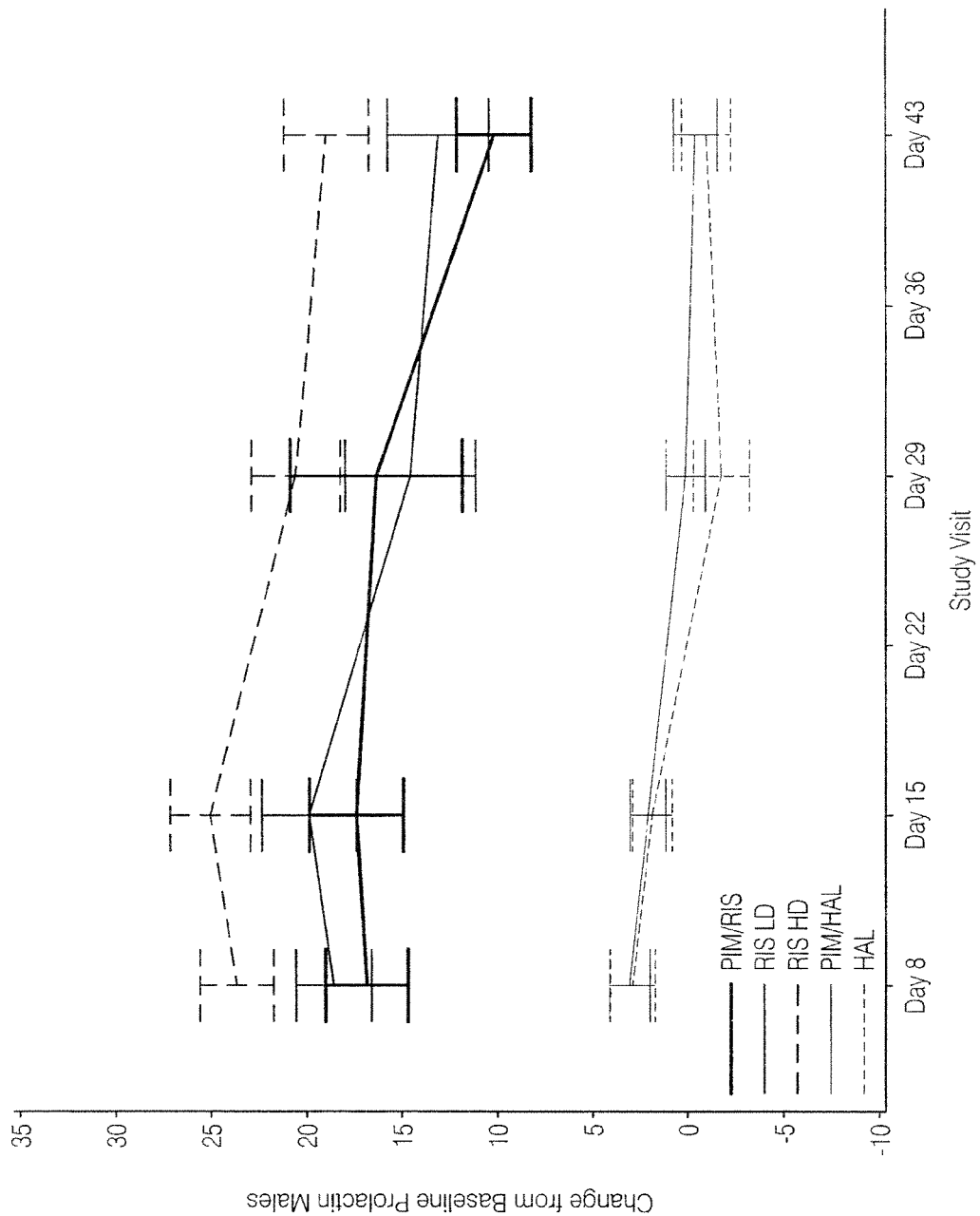
FIGS. 8A and 8B are graphs depicting change in prolactin levels in males and females, respectively, upon administration of risperidone and haloperidol alone and in combination with pimavanserin.
Figure 8B:
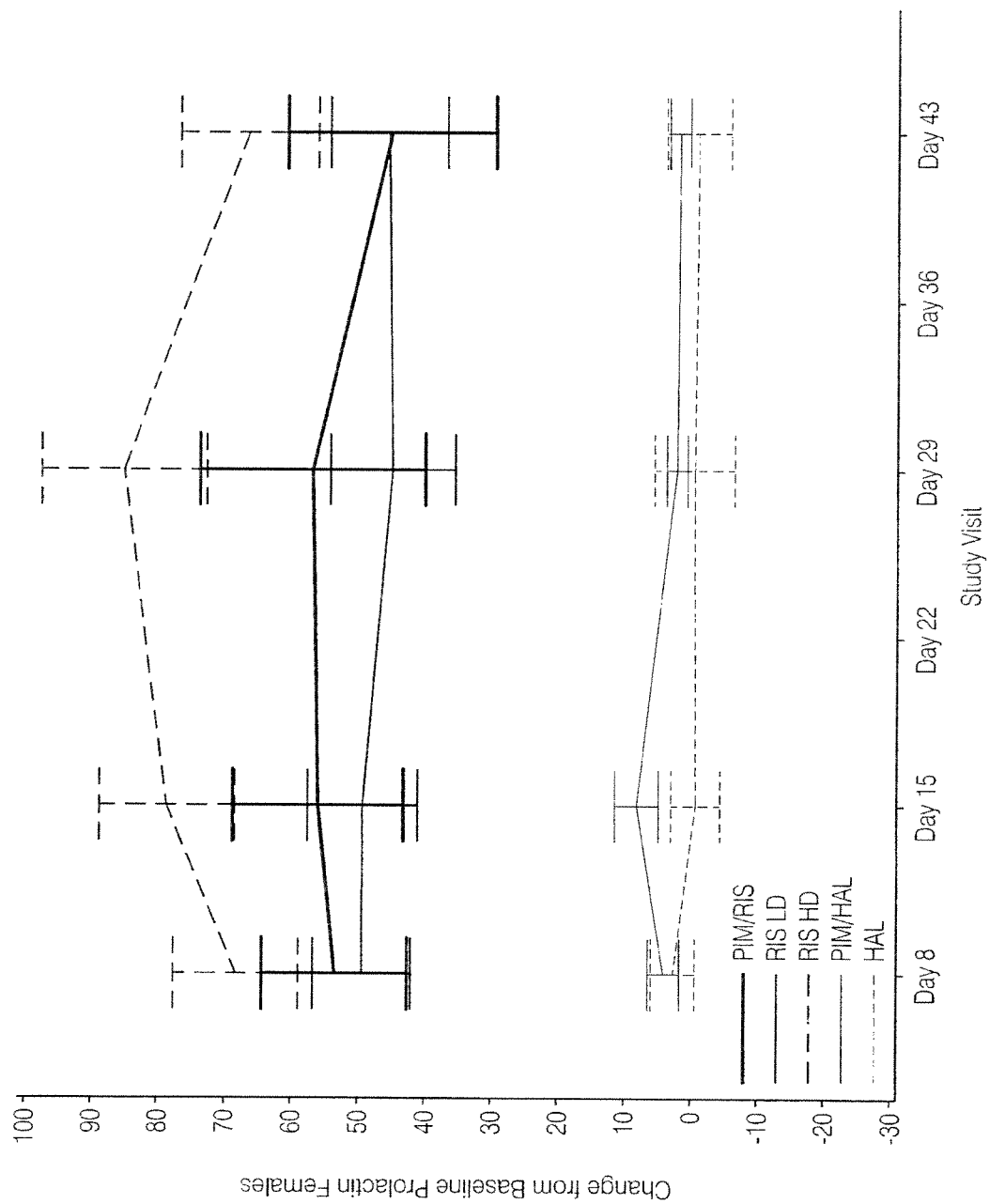

FIGS. 8A and 8B are graphs depicting the change from baseline (mean±SE; ng/mL) of prolactin levels at the end of treatment for males and females, respectively. The prolactin levels in both males and females were significantly less for the pimavanserin/risperidone combination patients than for those receiving high dose risperidone (p=0.015 for males, p=0.004 for females).

Figure 9:
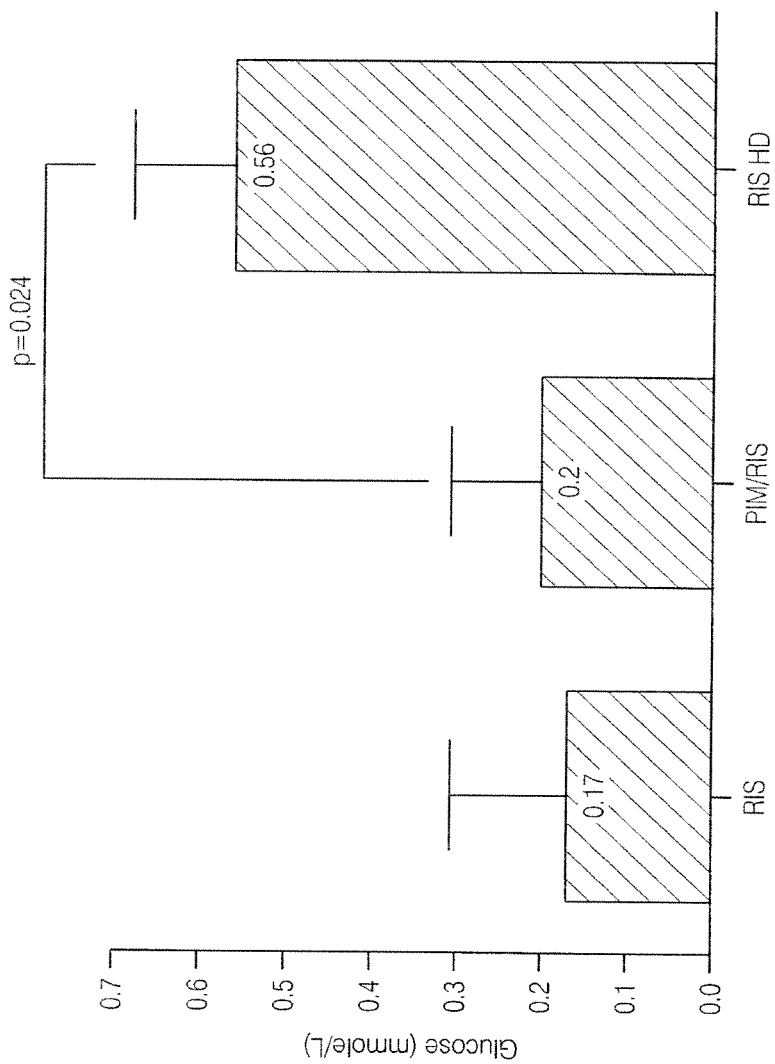
FIG. 9 is a bar graph depicting glucose levels upon administration of risperidone alone and in combination with pimavanserin.

FIG. 9 is a bar graph indicating the changes in glucose levels from baseline. The results indicated that patients receiving the pimavanserin/risperidone combination had less of an increase in glucose than those receiving high dose risperidone (p=0.024).

Figure 10:
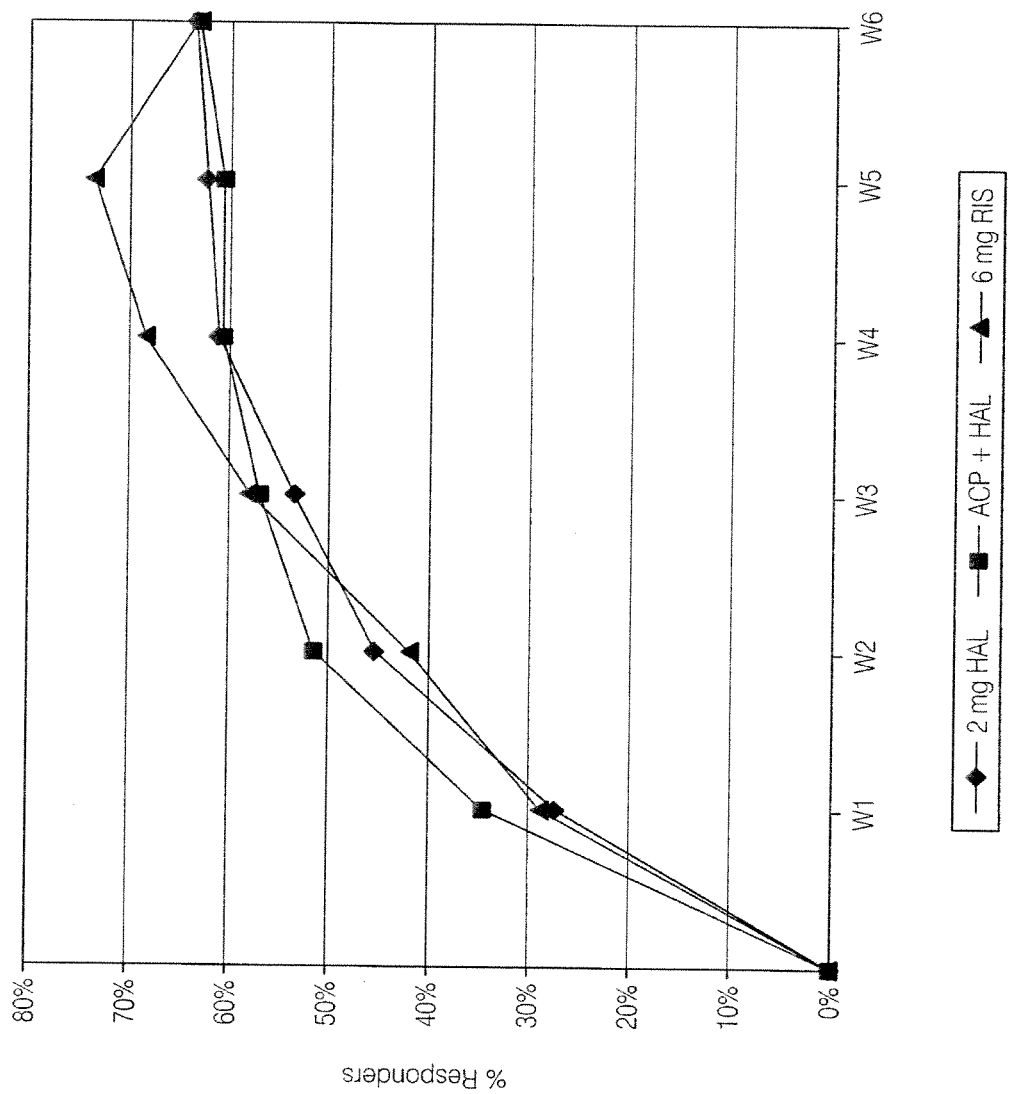
FIG. 10 is a graph depicting the percent of responders to therapy with risperidone or haloperidol, alone or in combination with pimavanserin.

The results of the study demonstrate that co-administering pimavanserin with haloperidol provided highly significant antipsychotic efficacy (p<0.0001) with similar efficacy to haloperidol administered alone. FIG. 10 is a graph depicting the percent of responders, defined as those subjects experiencing at least a 20% reduction in PANSS score. The results indicate that the combination treatment trended toward a faster onset of efficacy. Specifically, at two weeks after the start of treatment, the percent responders for the haloperidol/pimavanserin combination were higher than for haloperidol alone.

As Table 1 demonstrates, the haloperidol/pimavanserin combination also resulted in less weight gain than observed when administering haloperidol alone.

TABLE 1

|  | Haloperidol | Haloperidol + Pimavanserin |
|---|---|---|
| Initial mean weight (kg) | 82.993 | 82.943 |
| Final mean weight (kg) | 83.759 | 83.385 |
| Mean weight gain (kg) | 0.7657 | 0.4426 |

Co-administering pimavanserin with risperidone also provided highly significant antipsychotic efficacy (p<0.0001). Efficacy enhancement was observed when compared to 2 mg of risperidone administered alone (mean change in PANNS score of 23.0 vs. 16.6 points) and similar efficacy was observed when compared to 6 mg of risperidone administered alone. Efficacy of the combination was observed for both positive and negative symptoms of psychosis. The co-administration resulted in improved treatment of emotional withdrawal, lack of spontaneity and flow of conversation, abnormal mannerisms and posturing, motor retardation, uncooperativeness, lack of judgment and insight, poor impulse control, and preoccupation as compared to 6 mg per day of risperidone administered alone.

Figure 11:
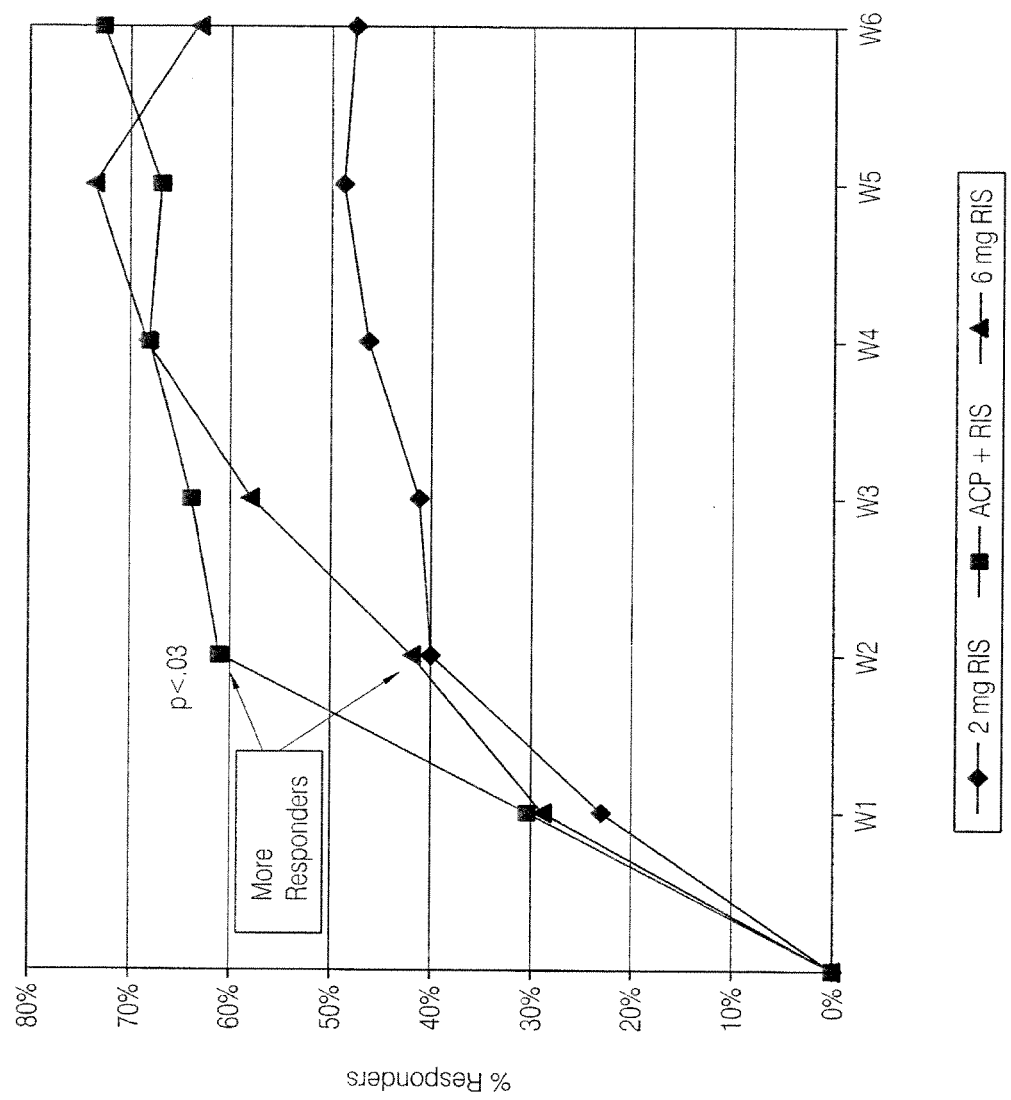
FIG. 11 is a graph depicting the percent of responders to therapy with risperidone alone or in combination with pimavanserin.

FIG. 11 is a graph depicting the percent of responders for those subjects receiving risperidone, defined as those subjects experiencing at least a 20% reduction in PANSS score. The results indicate that the combination treatment resulted in a faster onset of efficacy. Specifically, at two weeks after the start of treatment, the percent responders for the risperidone/pimavanserin combination were higher than for risperidone alone (both the 2 mg and 6 mg doses).

As Table 2 demonstrates, the risperidone/pimavanserin combination resulted in less weight gain than observed when administering 6 mg of risperidone alone. The difference was approaching statistical significance (p=0.0784).

TABLE 2

|  | 2 mg Risperidone | 6 mg Risperidone | Risperidone + pimavanserin |
|---|---|---|---|
| Initial mean weight (kg) | 80.702 | 79.216 | 79.533 |
| Final mean weight (kg) | 81.856 | 81.332 | 80.600 |
| Mean weight gain (kg) | 1.1540 | 2.1162 | 1.0667 |

Conclusion:

The combination of low dose risperidone with pimavanserin was superior to that of either low dose or high dose risperidone alone in terms of time of onset of response and percent of patients with good clinical response. The efficacy of haloperidol was not potentiated by pimavanserin, perhaps because with haloperidol alone, the occupancy of D2 receptors is sufficient to achieve optimal outcome, whereas that of low dose risperidone alone is not. The advantage of using low doses of atypicals+pimavanserin extends to reduced side effect burden on metabolic measures and EPS and, potentially, to a broadened efficacy.

The conclusions are summarized as follows:

Pimavanserin potentiated efficacy of low dose risperidone on psychopathology while reducing side effects.

Pimavanserin did not potentiate the efficacy of haloperidol.

Low dose risperidone was significantly less effective than the other treatments.

Pimavanserin enhanced the efficacy of low dose risperidone at all time points from week 2 on with regard to PANSS Total, POS, NEG, General, and CGI.

Pimavanserin/risperidone was more effective than high dose risperidone and low dose risperidone at day 15 with regard to % patients with ≥20% decrease in PANSS Total.

Pimavanserin/risperidone was as effective as high dose risperidone, haloperidol and pimavanserin/haloperidol at all time points, with all measures.

Pimavanserin/risperidone had less % of patients with ≥7% weight gain than high dose risperidone or low dose risperidone.

Serum glucose and prolactin levels (PRL) were lower in pimavanserin/risperidone than high dose risperidone; PRL levels were lower in haloperidol-treated patients compared to risperidone patients.

There was a trend to less akathesia in the pimavanserin co-therapy groups compared to the respective risperidone and haloperidol arms.

Example 2

Combinations of Haloperidol and Risperidone with Pimavanserin for Suppressing Drug-induced Hyperactivity in Mice Male non-Swiss albino (NSA) mice and Sprague-Dawley (SD) rats (Harlan, San Diego, Calif.) served as subjects for the present investigation. Animals were housed in climate-controlled rooms on a 12/12 light dark cycle with on lights at 0600 hr. Rats were housed in groups of two and mice were housed in groups of eight. Food and water was available ad libitum except during experimental procedures. At the time of testing, mice weighed 20-30 g and the rats weighed between 275-325 g.

Amphetamine, dizocilpine (i.e., MK-801), and haloperidol were obtained from Sigma (St. Louis, Mo.). Risperidone was obtained from Toronto Research Chemicals (North York, ON, Canada). Pimavanserin were synthesized by ACADIA Pharmaceuticals, Inc. Drugs were administered either in a volume of 0.1 mL per 10 g body weight or of 1.0 mL per kg body weight to mice and rats, respectively. The vehicle used for amphetamine, dizocilpine, and ACP-103 was saline. Amphetamine and dizocilpine were administered intraperitoneally (ip). The vehicle used for haloperidol and risperidone was 10% Tween 80 in saline unless otherwise specified. Haloperidol and risperidone were administered subcutaneously (sc), unless otherwise noted. The doses of pimavanserin are expressed as free-base and were administered by the sc route.

Amphetamine-induced Hyperlocomotor Activity Assay:

Hyperlocomotion was produced in mice by administration of amphetamine (3 mg/kg) 15 min prior to entering motor activity chambers (AccuScan Instruments, Columbus, Ohio). Dose response curves were constructed for haloperidol in the presence of vehicle or a fixed dose of pimavanserin (0.03 mg/kg). Vehicle or haloperidol was injected 30 min prior to entering activity chambers. Vehicle or pimavanserin was given 30 min prior to haloperidol (i.e., 60 min prior to entering activity chambers). Immediately prior to placing the mice into the activity chambers, the presence of ataxia and muscle incoordination was determined using the horizontal wire test (Vanover et al., 2004). Once inside the chambers, total distance traveled (DT) in cm was determined across a 15 min session. In order to generate dose-response curves, raw DT data were converted to % MPI: % MPI=((DT drug or drug combination−DT amphetamine control)/(DT vehicle control−DT amphetamine control))*100. The $ID_{50}$ values and the corresponding 95% CI were determined as previously mentioned. Mice had no prior exposure to the chambers and each dose combination was tested in separate groups of mice.

Dizocilpine-induced Hyperlocomotor Activity Assay:

Hyperlocomotion was produced in mice by administration of dizocilpine (0.3 mg/kg) 15 min prior to entering motor activity chambers. Dose response curves were constructed for haloperidol, risperidone and pimavanserin. Haloperidol or risperidone was injected 30 min prior to, and pimavanserin was administered 60 min prior to entering the activity chambers. Immediately prior to placing the mice into the activity chambers the presence of ataxia and muscle incoordination was determined as previously described and DT was determined across a 15 min session. Raw data were transformed to % MPI and $ID_{50}$ values and corresponding 95% CI were determined as previously described. Mice had no prior exposure to the chambers and each dose combination was tested in separate groups of mice.

Drug-interaction Studies:

Isobolographic analysis was used to determine the nature of the drug interaction between either haloperidol or risperidone and pimavanserin on suppression of dizocilpine-induced hyperlocomotor activity. This method is based on the comparison of dose combinations in which the doses of each individual agent are determined to be equi-efficacious. In this case, dose-response curves were generated following co-administration of either haloperidol or risperidone with pimavanserin in a fixed dose ratio based on the individual calculated $ID_{50}$ values. Therefore, separate groups received: pimavanserin $ID_{50}$+haloperidol or risperidone $ID_{50}$; (pimavanserin $ID_{50}$+haloperidol or risperidone $ID_{50}$)/2, (pimavanserin $ID_{50}$+haloperidol or risperidone $ID_{50}$)/4; and (pimavanserin $ID_{50}$+haloperidol or risperidone $ID_{50}$)/8. Based on the dose-response curves obtained for the combined agents (i.e., pimavanserin+haloperidol or pimavanserin+risperidone), $ID_{50}$ value and 95% CI for each drug combination was obtained.

Figure 12A:
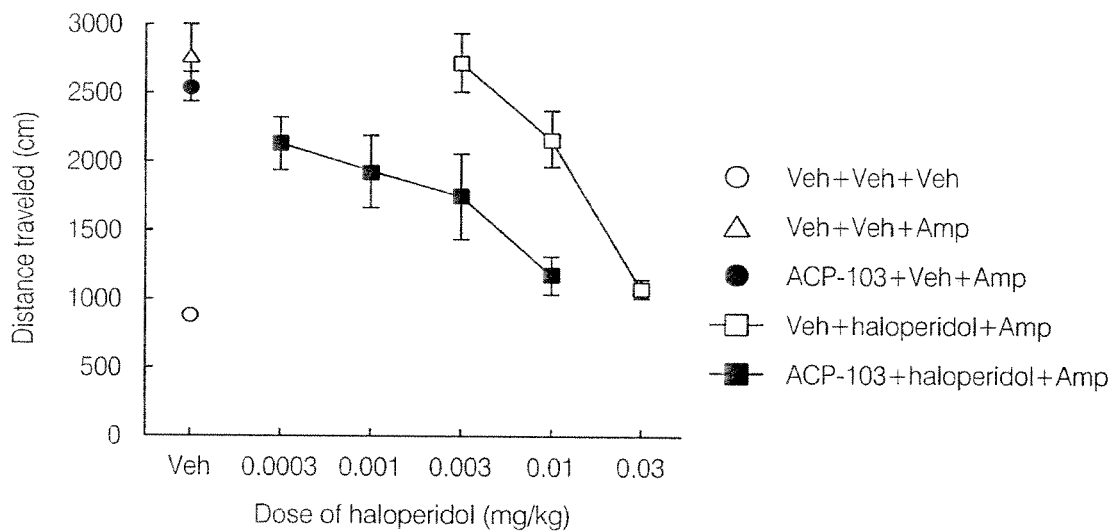
FIG. 12A is graph depicting the distance traveled by mice in an amphetamine-induced hyperlocomotor assay upon administration of pimavanserin, haloperidol, or pimavanserin in combination with haloperidol.

Effects of Haloperidol Alone, and in Combination with Pimavanserin, on Suppression of Amphetamine-induced Hyperlocomotion in Mice:

FIG. 12A is graph illustrating the distance traveled as a function of haloperidol dose for the various administered agents. Relative to vehicle controls (open circle), amphetamine (open triangle) significantly increases hyperlocomotor activity in mice (increased DT to 2764±230 cm from 876±42 cm obtained in the vehicle controls). Pimavanserin at a dose of 0.03 mg/kg (filled circle) failed to suppress hyperlocomotion produced by amphetamine. In contrast, haloperidol (open squares) dose dependently attenuated hyperactivity produced by amphetamine. However, haloperidol, when combined with a fixed dose of pimavanserin (0.03 mg/kg, filled squares), demonstrated an enhanced suppression of amphetamine-induced hyperlocomotor activity.

Figure 12B:
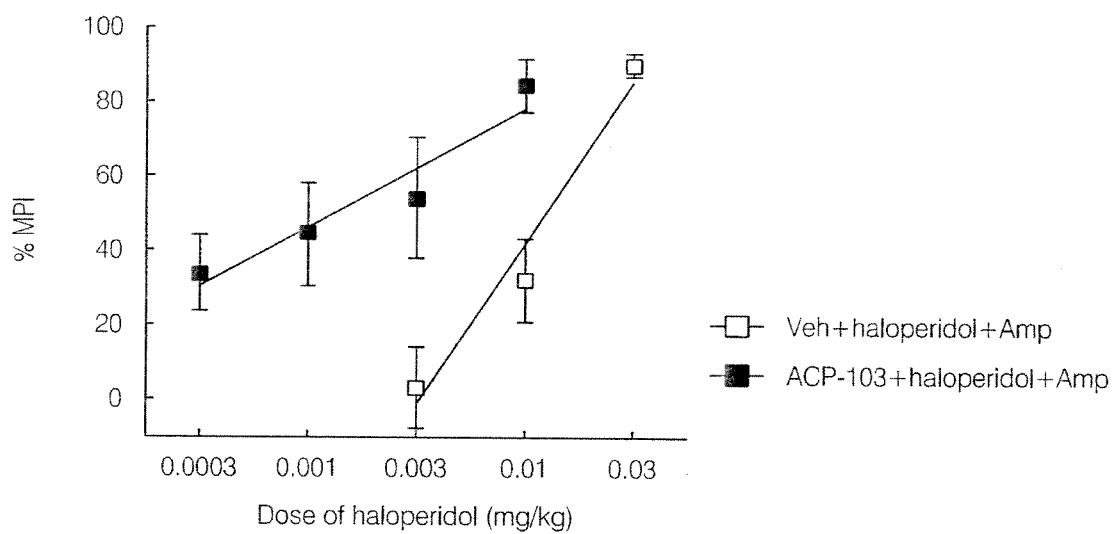
FIG. 12B is a graph depicting dose response curves for administration to mice of pimavanserin, haloperidol, or pimavanserin in combination with haloperidol in an amphetamine-induced hyperlocomotor assay.

The raw data contained in FIG. 12A were converted to % MPI to generate dose-response curves depicted in FIG. 12B. Haloperidol (open squares) produced a dose-dependent attenuation of hyperactivity elicited by amphetamine with a calculated $ID_{50}$ value of 0.012 mg/kg (0.009-0.016; 95% CI). However, when combine with a fixed dose of pimavanserin (0.03 mg/kg, filled squares), the dose-response curve for haloperidol was significantly shifted to the left by a factor of approximately 10 with a calculated $ID_{50}$ value of 0.0013 mg/kg (0.0005-0.0031; 95% CI). The combination of pimavanserin and haloperidol resulted in a 9.5-fold (3.8-23.8; 95% CI) shift in potency. Each data point represents a minimum n of 8.

Figure 13A:
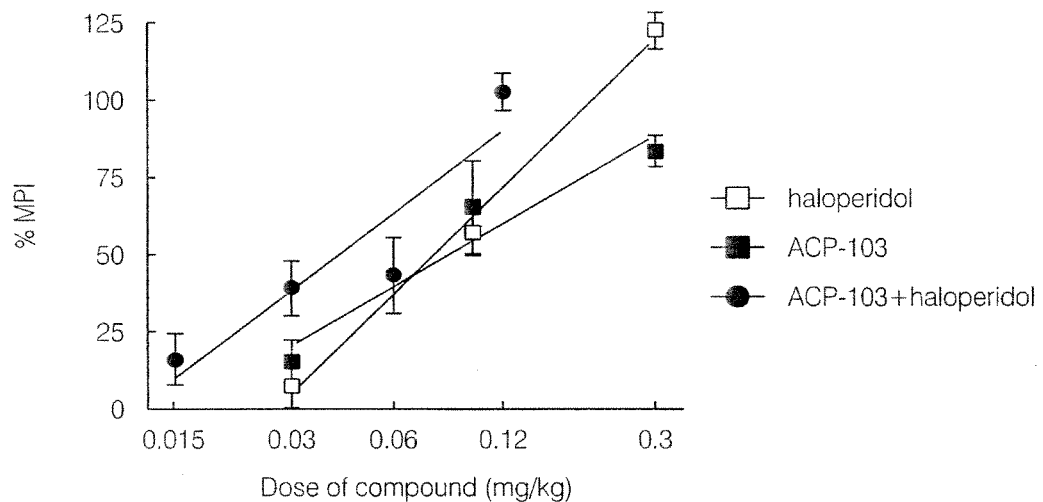
FIG. 13A is a graph depicting dose response curves for administration to mice of pimavanserin, haloperidol, or pimavanserin in combination with haloperidol in a dizocilpine-induced hyperlocomotor assay.

Effects of Haloperidol and Pimavanserin, Alone and in Combination, on Suppression of Dizocilpine-induced Hyperlocomotion in Mice:

FIG. 13A is a graph depicting dose response curves for haloperidol (open squares), pimavanserin (filled squares), and the combination of haloperidol with pimavanserin in a 1:1 fixed dose ratio (filled circles) on the suppression of dizocilpine-induced hyperactivity. Each data point represents a minimum n of 16. As expected, dizocilpine treatment significantly increased DT to 2227±116 cm from 792±40 cm obtained in the vehicle controls. Administration of either haloperidol or pimavanserin elicited a dose-dependent attenuation of dizocilpine-induced hyperlocomotion achieving $ID_{50}$ values of 0.07 mg/kg (0.063-0.087; 95% CI) and 0.09 mg/kg (0.067-0.12; 95% CI), respectively. Given that haloperidol and pimavanserin were equipotent in this assay, a 1:1 fixed-dose ratio (haloperidol:ACP-103) was administered in fractions of the approximated $ID_{50}$ dose combinations of 0.06+0.06 mg/kg ($ID_{50}/2$=0.03+0.03 mg/kg; $ID_{50}/4$=0.015+0.015 mg/kg; $ID_{50}/8$=0.0075+0.0075 mg/kg). Co-administration of haloperidol and pimavanserin produced a dose-dependent attenuation of hyperlocomotor activity induced by dizocilpine achieving a % MPI of 103±6%.

Figure 13B:
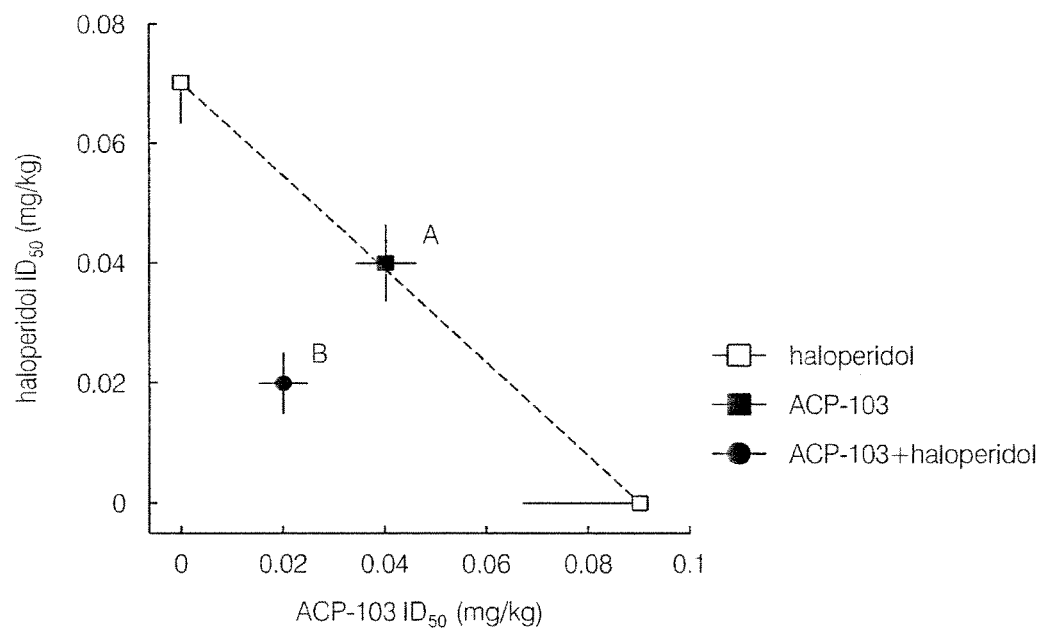
FIG. 13B is a graph depicting an isobologram that demonstrates synergism upon administration of haloperidol in combination with pimavanserin.

Isobolographic analysis conducted using the equipment ratio and the resulting isobologram is presented in FIG. 13B. The calculated $ID_{50}$ (and 95% CI) values for pimavanserin and haloperidol when administered alone (open squares) are plotted on the x- and y-axes, respectively. The dashed line connecting these two points represents the line of theoretical additivity. The experimental ID$_{50}$ (filled circle, B) for the dose combination was significantly less than the theoretical ID$_{50}$ (filled square, A), indicating a synergistic interaction. The experimental ID$_{50}$ for the dose mixture was significantly less than the theoretical ID$_{50}$, values of 0.04 mg/kg (0.03-0.05; 95% CI) and 0.08 mg/kg (0.68-0.93; 95% CI), respectively. These results indicate that efficacy is maintained at 50% of haloperidol dose.

Figure 14A:
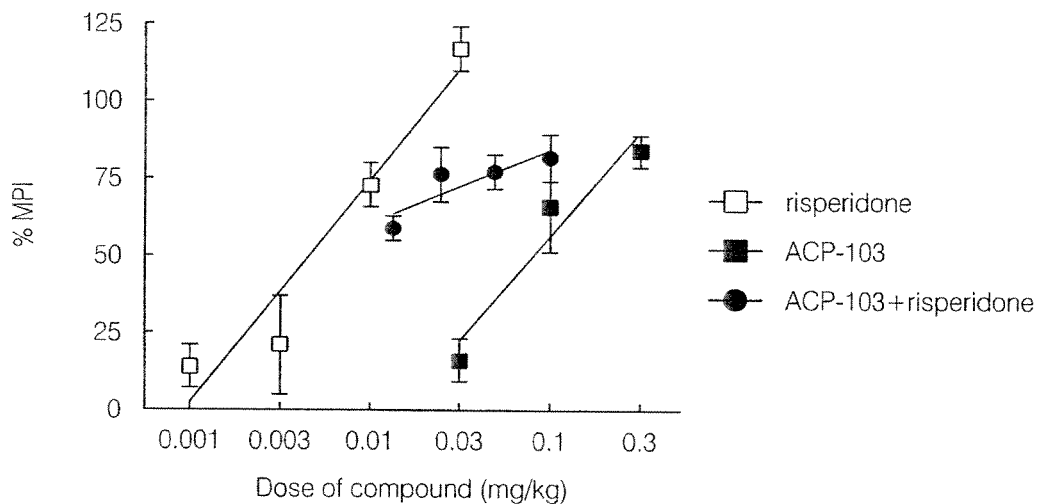
FIG. 14A is a graph depicting dose response curves for administration to mice of pimavanserin, risperidone, or pimavanserin in combination with risperidone in a dizocilpine-induced hyperlocomotor assay.

Effects of Risperidone and Pimavanserin, Alone and in Combination, on Suppression of Dizocilpine-induced Hyperlocomotion in Mice:

FIG. 14A is a graph depicting dose response curves for risperidone (open squares), pimavanserin (filled squares), and the combination of risperidone with pimavanserin in a 1:18 fixed dose ratio (filled circles) on the suppression of dizocilpine-induced hyperactivity. Each data point represents a minimum n of 16. As in the previous experiment, dizocilpine treatment significantly increased total DT to 2020±223 cm from 649±67 cm obtained in the vehicle controls. Administration of either risperidone or pimavanserin elicited a dose-dependent attenuation of dizocilpine-induced hyperlocomotion achieving ID$_{50}$ values of 0.0045 mg/kg (0.003-0.006; 95% CI) and 0.09 mg/kg (0.067-0.12; 95% CI), respectively. Given that risperidone was more potent than pimavanserin in this assay, a 1:18 fixed-dose ratio (risperidone:pimavanserin) was administered in fractions of the approximated ID$_{50}$ dose combinations of 0.005+0.09 mg/kg (ID$_{50}$/2=0.0025+0.045 mg/kg; ID$_{50}$/4=0.00125+0.0225 mg/kg; ID$_{50}$/8=0.000625+0.01125 mg/kg). Co-administration of risperidone and pimavanserin produced a dose-dependent attenuation of hyperlocomotor activity induced by dizocilpine achieving a % MPI of 82±8%.

Figure 14B:
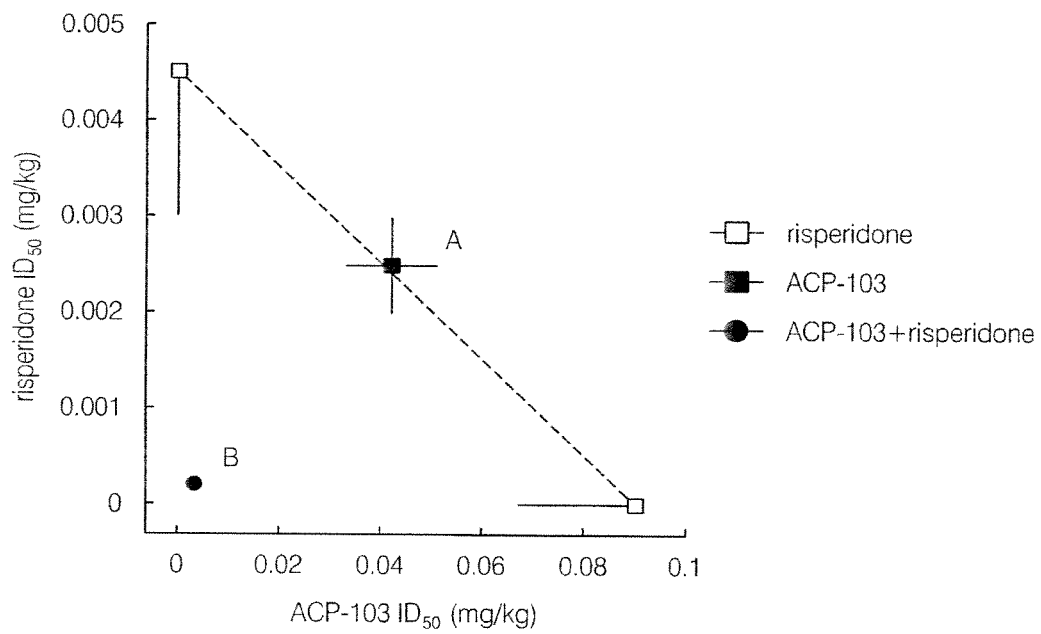
FIG. 14B is a graph depicting an isobologram that demonstrates synergism upon administration of risperidone in combination with pimavanserin.

Isobolographic analysis was conducted using the fixed dosing ratio and the resulting isobologram is presented in FIG. 14B. The calculated ID$_{50}$ (and 95% CI) values for pimavanserin and risperidone when administered alone (open squares) are plotted on the x- and y-axes, respectively. The dashed line connecting these two points represents the line of theoretical additivity. The experimental ID$_{50}$ (filled circle, B) for the dose combination was significantly less than the theoretical ID$_{50}$ (filled square, A), indicating a synergistic interaction. The experimental ID$_{50}$ for the dose mixture was significantly less than the theoretical ED$_{50}$, values of 0.0032 mg/kg (0.0007-0.0058 95% CI) and of 0.045 mg/kg (0.035-0.054; 95% CI), respectively. These results indicate that efficacy is maintained at ⅓ of risperidone dose.

Conclusion:

Pimavanserin, at a dose that does not suppress amphetamine-induced hyperactivity, when combined with haloperidol, produced an approximate 10-fold shift in the potency of haloperidol against amphetamine-induced hyperactivity. Further, pimavanserin interacted synergistically with haloperidol, and with risperidone, to reduce dizocilpine-induced hyperactivity. The supra-additive actions of pimavanserin were not achieved by simply altering the pharmacokinetics of either haloperidol or risperidone, as brain exposures for these agents were not significantly altered in the presence of pimavanserin. For example, Table 3 indicates brain levels of pimavanserin and haloperidol for various dosages. The results indicate that full efficacy can be achieved using the combination with one half haloperidol brain concentration. The doses used in these studies are consistent with a 5-HT$_{2A}$ receptor mechanism of action. These data indicate that even for compounds that possess high affinity for 5-T$_{2A}$ receptors, complete 5-HT$_{2A}$ receptor occupancy is not likely achieved at doses that elicit antipsychotic-like activity.

TABLE 3

| Treatment conditions | Pimavanserin brain levels (nmol/kg) | Haloperidol brain levels (nmol/kg) |
|---|---|---|
| Pim + Veh | 23 (±6) | |
| Veh + Hal (0.003) | | <10 |
| Veh + Hal (0.01) | | 43 (±5) |
| Veh + Hal (0.03) | | 113 (±25) |
| Pim + Hal (0.0003) | 17 (±6) | <10 |
| Pim + Hal (0.001) | 14 (±4) | 11 (±3) |
| Pim + Hal (0.003) | 25 (±5) | 12 (±4) |
| Pim + Hal (0.01) | 14 (±6) | 45 (±7) |

The mechanism by which 5-HT$_{2A}$ receptor blockade enhances the action of antipsychotics (APDs) in these models is unknown, however, microdialysis and other studies suggest several possibilities. While not being bound by any particular theory, one possibility is that 5-HT$_{2A}$ inverse agonists may have regionally specific effects on dopamine (DA) transmission. Previous studies have shown that DOI increases DA release and potentiates amphetamine-induced DA release in the nuclear accumbens (NAC), suggesting that 5-HT$_{2A}$ receptor inverse agonists are more apt to modulate evoked, rather than basal, DA release. Haloperidol, which potently inhibits amphetamine hyperactivity, has been shown to paradoxically increase DA release in the NAC, an effect blocked by pimavanserin. These data suggest that pimavanserin may potentiate the actions of haloperidol via direct or indirect modulation of evoked DA release in the NAC. Another possibility is that 5-HT$_{2A}$ inverse agonists may block a "pro-psychotic" drive associated with APD-induced enhanced serotonergic transmission in limbic or cortical structures. Following systemic administration of NMDA antagonists, extracellular DA and 5-HT concentrations rise in the NAC, and medial prefrontal cortex (mPFC). High doses of atypical APDs, such as clozapine and olanzapine, but not typical APDs, such as haloperidol, produce preferential increases in DA release in the mPFC compared to the NAC, a property that may explain how atypical APDs improve cognition in schizophrenia. Regardless of the mechanism, these findings indicate that pimavanserin has dose-sparing actions for APDs in models predictive of antipsychotic action.

In conclusion, the above data suggests that pimavanserin, via 5-HT$_{2A}$ receptor antagonism or inverse agonism, results in a significant dose-sparing effect such that antipsychotic efficacy can be maintained, or improved, while concomitantly reducing the severity of unwanted side effects mediated via D$_2$ receptor antagonism. The findings with risperidone suggest that the dose-sparing benefits of pimavanserin will be manifested even with those atypical APDs having an inherently high affinity for 5-HT$_{2A}$ receptors. This is consistent with clinical findings indicating that even for those APDs which have relatively high affinity for 5-HT$_{2A}$ receptors, 5-HT$_{2A}$ receptor blockade is not fully achieved at clinically tolerated doses.

Example 3

Figure 15A:
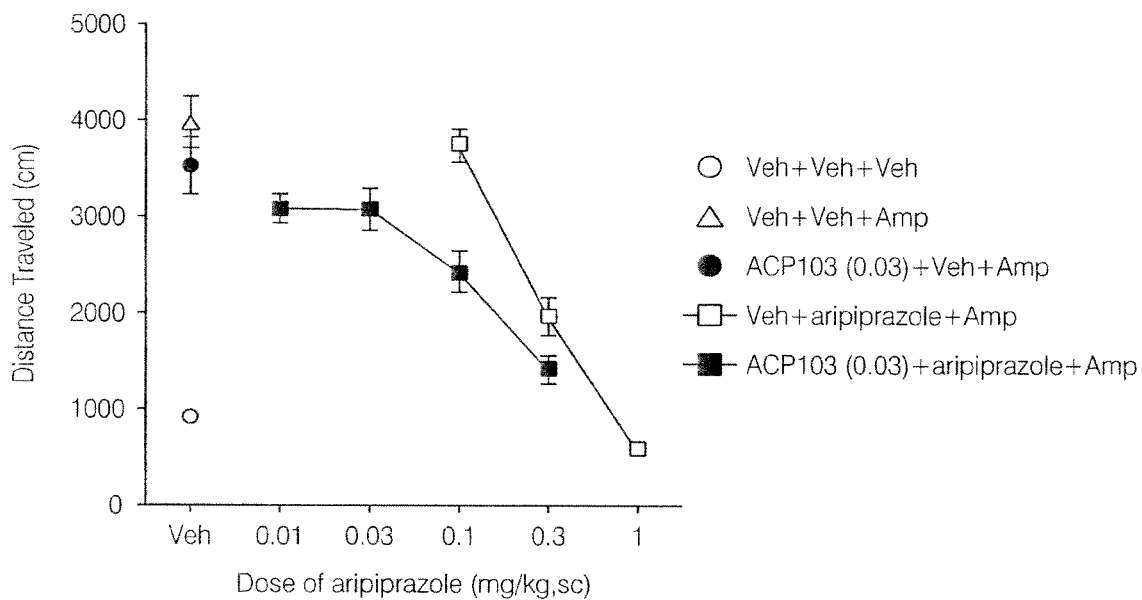
FIG. 15A is graph illustrating the distance traveled by mice in an amphetamine-induced hyperlocomotor assay upon administration of pimavanserin, aripiprazole, or pimavanserin in combination with aripiprazole.

Combinations of Aripiprazole and Quetiapine with Pimavanserin for Suppressing Drug-induced Hyperactivity in Mice The protocol described above in Example 2 was repeated using aripiprazole and quetiapine antipsychotics. FIG. 15A is graph illustrating the distance traveled as a function of aripiprazole dose for the various administered agents. Relative to vehicle controls (open circle), amphetamine (open triangle) significantly increases hyperlocomotor activity in mice.

Pimavanserin at a dose of 0.03 mg/kg (filled circle) failed to suppress hyperlocomotion produced by amphetamine. In contrast, aripiprazole (open squares) dose dependently attenuated hyperactivity produced by amphetamine. However, aripiprazole, when combined with a fixed dose of pimavanserin (0.03 mg/kg, filled squares), demonstrated an enhanced suppression of amphetamine-induced hyperlocomotor activity.

Figure 15B:
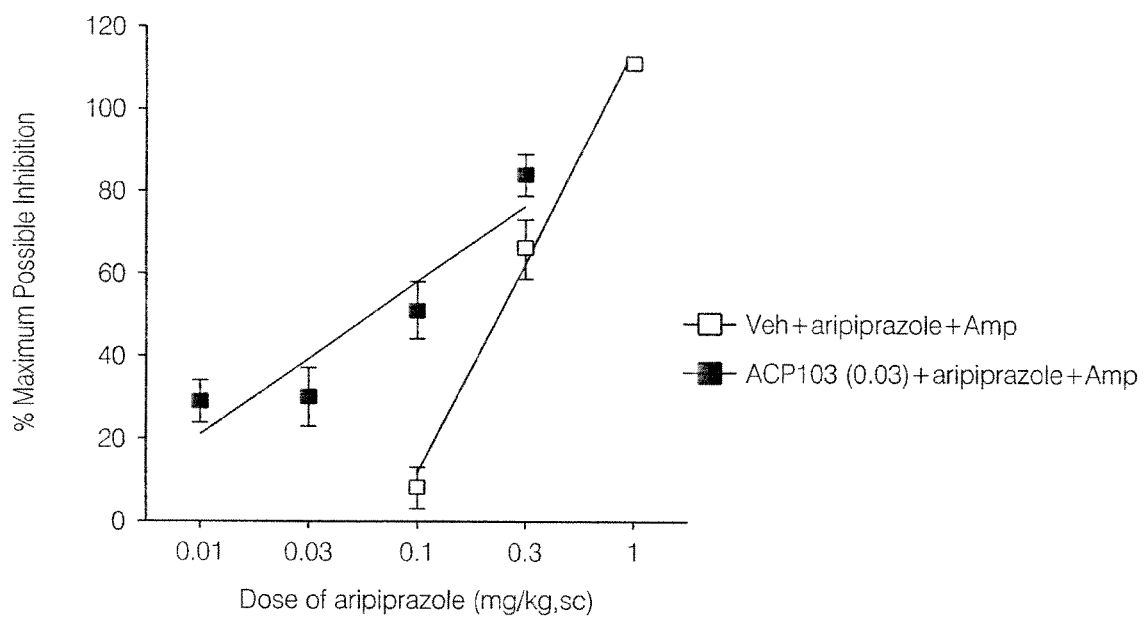
FIG. 15B is a graph illustrating dose response curves for administration to mice of pimavanserin, aripiprazole, or pimavanserin in combination with aripiprazole in an amphetamine-induced hyperlocomotor assay.

The raw data contained in FIG. 15A were converted to % MPI to generate dose-response curves depicted in FIG. 15B. Aripiprazole (open squares) produced a dose-dependent attenuation of hyperactivity elicited by amphetamine. However, when combined with a fixed dose of pimavanserin (0.03 mg/kg, filled squares), the dose-response curve for aripiprazole was significantly shifted to the left.

Figure 16A:
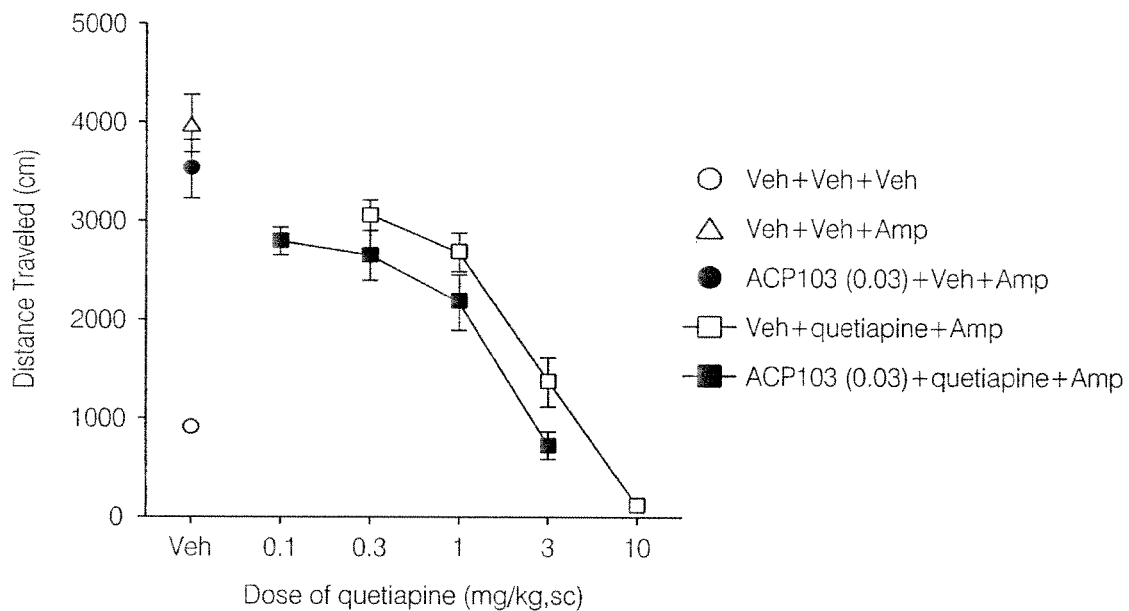
FIG. 16A is graph illustrating the distance traveled by mice in an amphetamine-induced hyperlocomotor assay upon administration of pimavanserin, quetiapine, or pimavanserin in combination with quetiapine.

FIG. 16A is graph illustrating the distance traveled as a function of quetiapine dose for the various administered agents. Relative to vehicle controls (open circle), amphetamine (open triangle) significantly increases hyperlocomotor activity in mice. Pimavanserin at a dose of 0.03 mg/kg (filled circle) failed to suppress hyperlocomotion produced by amphetamine. In contrast, quetiapine (open squares) dose dependently attenuated hyperactivity produced by amphetamine. However, quetiapine, when combined with a fixed dose of pimavanserin (0.03 mg/kg, filled squares), demonstrated an enhanced suppression of amphetamine-induced hyperlocomotor activity.

Figure 16B:
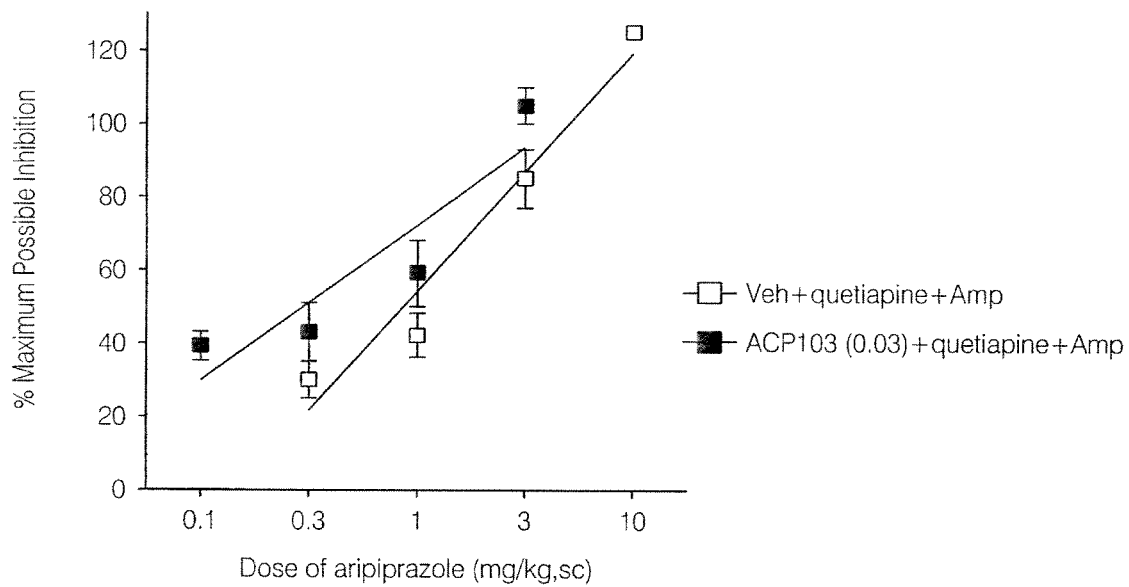
FIG. 16B is a graph illustrating dose response curves for administration to mice of pimavanserin, quetiapine, or pimavanserin in combination with quetiapine in an amphetamine-induced hyperlocomotor assay.

The raw data contained in FIG. 16A were converted to % MPI to generate dose-response curves depicted in FIG. 16B. Quetiapine (open squares) produced a dose-dependent attenuation of hyperactivity elicited by amphetamine. However, when combined with a fixed dose of pimavanserin (0.03 mg/kg, filled squares), the dose-response curve for quetiapine was shifted to the left.

Figure 17:
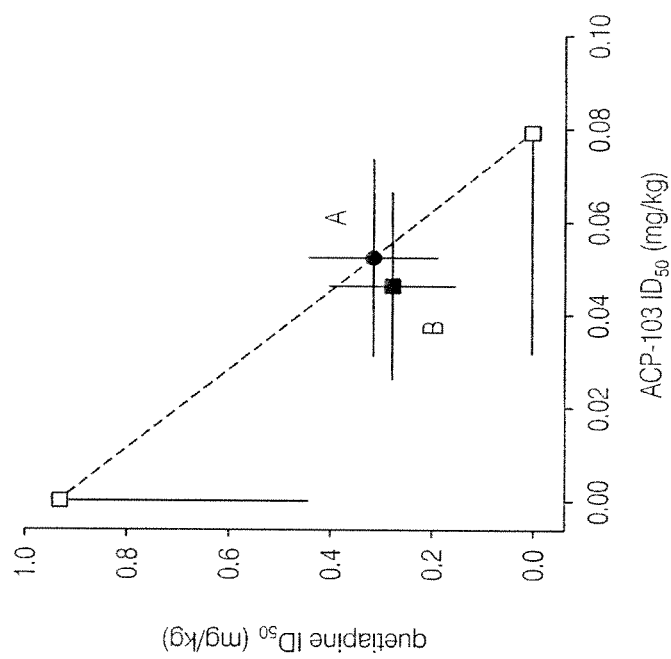
FIG. 17 is a graph depicting an isobologram that demonstrates additivity upon administration of quetiapine in combination with pimavanserin.

The effects of quetiapine and pimavanserin, alone and in combination, on suppression of dizocilpine-induced hyperlocomotion in mice was also evaluated. Isobolographic analysis was conducted and the resulting isobologram is presented in FIG. 17. The calculated $ID_{50}$ (and 95% CI) values for pimavanserin and quetiapine when administered alone (open squares) are plotted on the x- and y-axes, respectively. The dashed line connecting these two points represents the line of theoretical additivity. The experimental $ID_{50}$ (filled square, B) for the dose combination was not significantly different than the theoretical $ID_{50}$ (filled circle, A), indicating an additive interaction.

Example 4

Use of Pimavanserin for Reversing Cognitive Impairment in Mice Administered Anti-psychotics Various antipsychotics were administered alone or in combination with pimavanserin to mice in an in vivo mouse model of cognition. Compounds were administered to mice at one hour post-training (a time-point at which animals normally behaviorally discriminate between novel and familiar objects) and two hours post-training (a time-point at which these animals normally no longer discriminate between objects).

Figure 18:
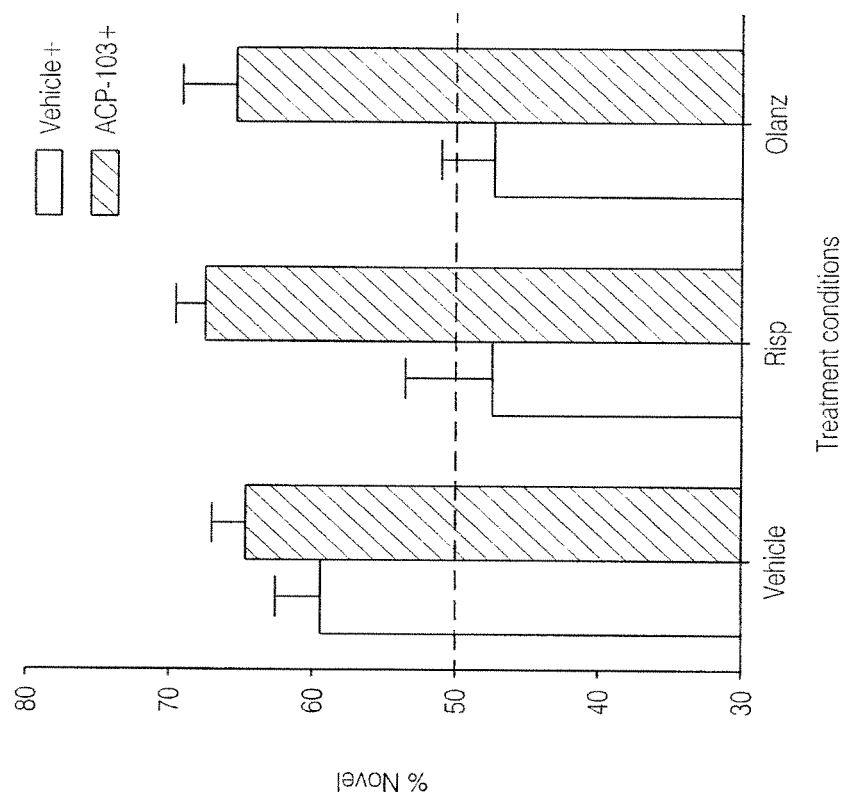
FIG. 18 is a bar graph depicting percent novel object recognition upon administration of vehicle, pimavanserin, risperidone, olanzapine, and combinations of pimavanserin with risperidone or olanzapine in a novel object recognition assay.

FIG. 18 is a bar graph of percent novel object recognition upon administration of vehicle, pimavanserin (0.3 mg/kg), risperidone, olanzapine, and combinations of pimavanserin with risperidone or olanzapine. The results indicate that pimavanserin reverses novel object recognition impairment caused by risperidone and olanzapine.

Figure 19:
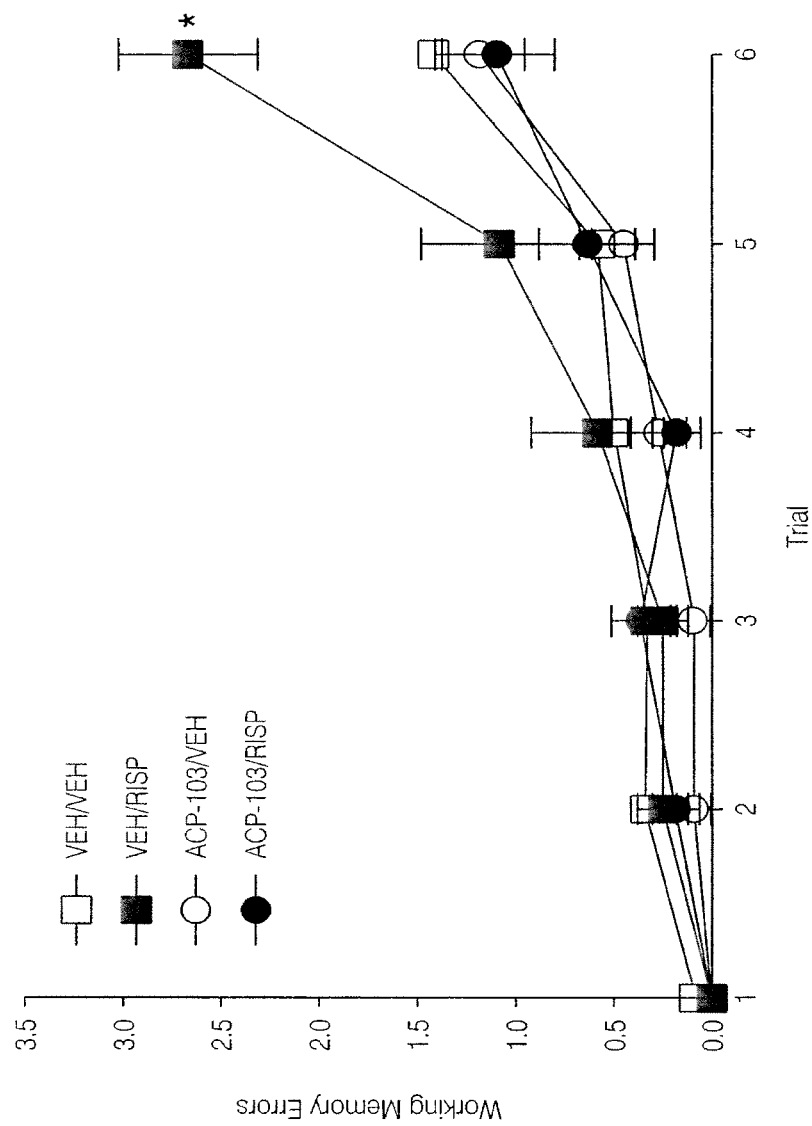
FIG. 19 is a graph depicting working memory errors after repeated trials upon administration of vehicle, risperidone, pimavanserin, and combinations of risperidone with pimavanserin in a radial arm maze in vivo mouse model of cognition.

Combinations of pimavanserin and risperidone were also evaluated in a radial arm maze in vivo mouse model of cognition. FIG. 19 is a graph indicating working memory errors after repeated trials upon administration of vehicle, risperidone, pimavanserin (1 mg/kg), and combination of risperidone with pimavanserin. The results indicated that pimavanserin improved the cognitive deficit induced by risperidone.

Example 5

Attenuation of Other Side Effects when Pimavanserin is Co-administered with Antipsychotics Prolactin Assay:
Dose response curves were generated for haloperidol, risperidone and pimavanserin on serum prolactin levels. Rats were dosed ip with vehicle (100% dimethyl sulfoxide), haloperidol or risperidone, while pimavanserin or vehicle (saline) was given sc. Blood samples were collected 30 min following vehicle, haloperidol or risperidone administration or 60 min after pimavanserin administration. Rats were deeply anesthetized with isoflurane and blood samples were obtained by cardiac puncture, allowed to clot and then centrifuged at 12,000 rpm for 10 min to yield serum for analysis. Serum prolactin levels were quantified using a commercially available enzyme immunoassay kit (ALPCO Diagnostics, Windham, N.H.).

In order to explore the potential interaction between haloperidol or risperidone and pimavanserin on serum prolactin levels, rats were dosed sc with either vehicle or various doses of pimavanserin, then 30 min later, dosed ip with either vehicle or a fixed dose of haloperidol or risperidone. Blood samples were collected 30 min following vehicle, haloperidol or risperidone administration (i.e., 60 min following vehicle or pimavanserin administration). The time point for sample collection was chosen based on our work and that of others (Liegeois et al., 2002b), which show that 30 min appears to be the time at which peak prolactin levels can be detected following risperidone or haloperidol treatment, respectively. The fixed doses of haloperidol (0.1 mg/kg) and risperidone (0.01 mg/kg) were chosen since they elicited statistically significant and reproducible, but sub-maximal, increases in prolactin, thus allowing for the detection of potential increases as well as decreases.

Figure 20A:
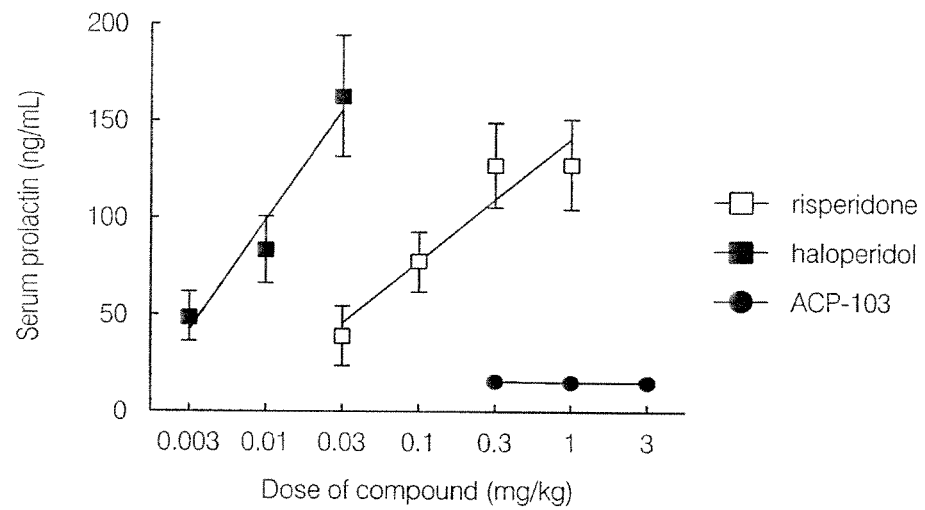
FIG. 20A is a graph depicting serum prolactin levels upon administration of risperidone, haloperidol, or pimavanserin.

Effects of Haloperidol and Risperidone Alone, and in Combination with Pimavanserin, on Serum Prolactin Levels in Rats:

FIG. 20A is a graph depicting the dose response of prolactin levels obtained in rats following various doses of risperidone (filled squares), haloperidol (open squares) and pimavanserin (filled circles). Serum prolactin levels obtained in vehicle-treated controls were 24±3 ng/mL and 31±3 ng/mL after 30 min and 60 min, respectively. As expected, 60 min following haloperidol treatment rats demonstrated a dose-related increase in serum prolactin levels as compared to vehicle controls. Similarly, 30 min following risperidone treatment, a dose-dependent increase in serum prolactin levels was observed. In contrast, pimavanserin treatment, up to 3 mg/kg, did not significantly elevate serum prolactin levels as compared to vehicle-treated controls. Rather, rats treated with pimavanserin demonstrated a significant reduction in serum prolactin concentrations, as the values obtained were 31±3 ng/mL and 15±0 ng/mL after vehicle and 3 mg/kg pimavanserin, respectively. All rats treated with 3 mg/kg pimavanserin had serum prolactin concentrations below the limit of detection; hence a value of 15 ng/mL was assigned.

Figure 20B:
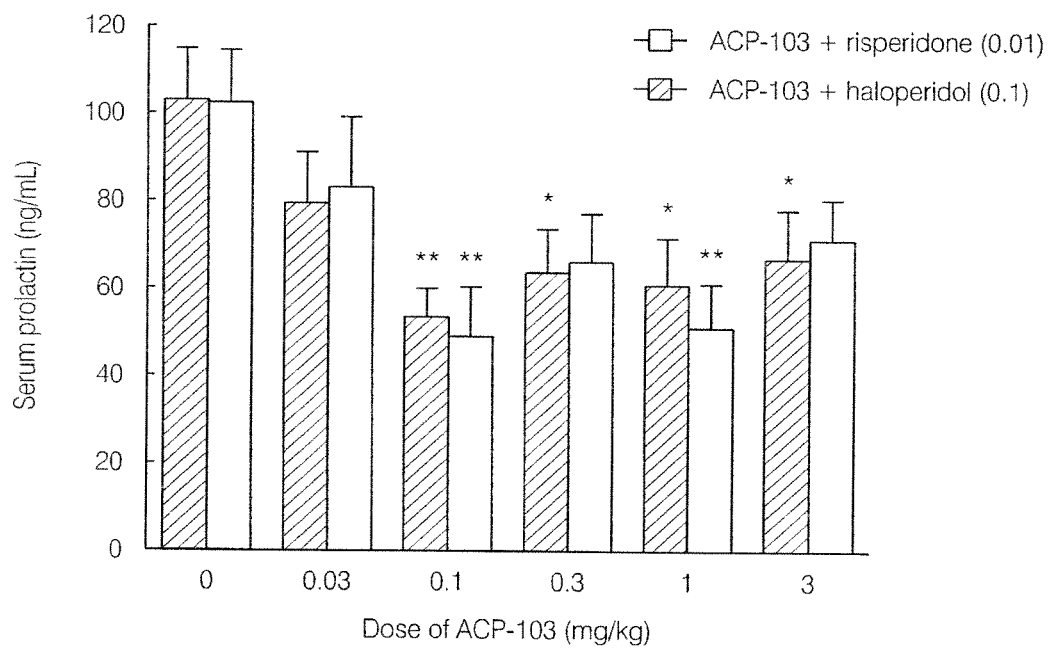
FIG. 20B is a bar graph depicting serum prolactin levels upon administration of pimavanserin in combination with risperidone or haloperidol.

FIG. 20B depicts the serum prolactin levels obtained in rats following fixed doses of risperidone (0.01 mg/kg; filled bars) or haloperidol (0.1 mg/kg; open bars) in the presence of vehicle or various doses of pimavanserin. Each data point represents a minimum n of 12. ** denotes p<0.01; * denotes p<0.05. The dose of haloperidol significantly increased serum prolactin levels from 31±3 ng/mL to 102±12 ng/mL. Similarly, risperidone significantly increased serum prolactin levels from 24±3 ng/mL to 102±12 ng/mL. However, in the presence of pimavanserin, at doses consistent with $5\text{-}HT_{2A}$ receptor blockade, the magnitude of prolactinemia induced by either haloperidol or risperidone was significantly attenuated.

Catalepsy Assessment:

Rats were positioned with their forepaws on a horizontal bar (diameter 10 mm); elevated 10 cm above the bench top, and the duration of the cataleptic bout was recorded up to a maximum catalepsy value of 120 sec. Catalepsy values (CVs) were obtained at 30 and 60 min following ip administration risperidone or haloperidol, respectively. Doses of pimavanserin were administered sc 60 min prior to either haloperidol or risperidone. In order to generate dose-response curves raw CVs were converted to percentage maximum possible catalepsy (% MPC): % MPC=((CV drug or drug combination−CV vehicle control)/(120−CV vehicle control))*100. The dose that elicits 50% of maximum catalepsy ($CD_{50}$) and the corresponding 95% CI was determined for each compound as previously mentioned. Each dose or dose combination was assessed in separate groups of rats.

Figure 21A:
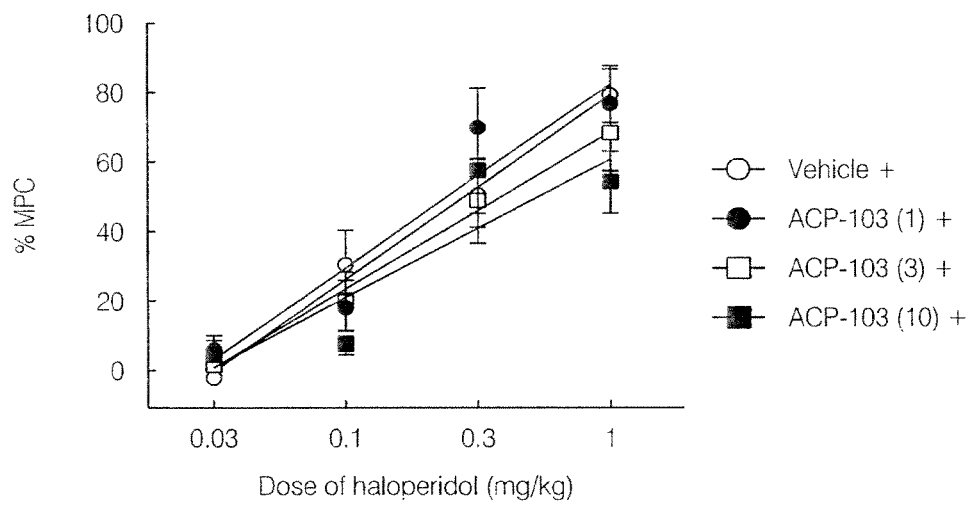
FIGS. 21A and 21B depict dose response curves for haloperidol- and risperidone-induced catalepsy in rats, respectively, upon administration of pimavanserin.

Effects of Pimavanserin on Haloperidol- and Risperidone-induced Catalepsy in Rats:

FIG. 21A depicts dose response curves as a function of haloperidol dose. As expected, haloperidol (open circles) produced a dose-dependent increase in catalepsy time in rats. Pimavanserin failed to potentiate haloperidol-induced catalepsy at any of the doses tested. The combination of 1 (filled circles) or 3 mg/kg (open squares) of pimavanserin with haloperidol did not significantly alter haloperidol-induced catalepsy, $CD_{50}$ values of 0.24 mg/kg (0.16-0.36; 95% CI) and 0.38 mg/kg (0.24-0.61; 95% CI), respectively. However, the addition of 10 mg/kg pimavanserin (filed squares) to haloperidol significantly increased the observed $CD_{50}$ value from 0.27 mg/kg (0.19-0.39; 95% CI) to 0.53 mg/kg (0.31-0.91; 95% CI) indicating a reduction of catalepsy.

Figure 21B:
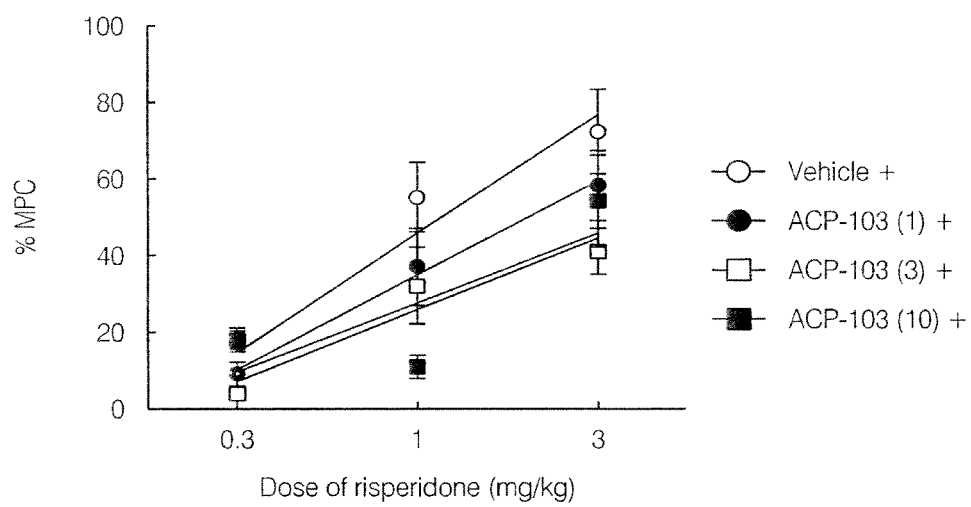

FIG. 21B depicts dose response curves as a function of risperidone dose. As expected, risperidone (open circles) produced a dose-dependent increase in catalepsy time in rats. Each data point represents a minimum n of 12. Vehicle treatment elicited a maximum CV of 6.8±0.9 sec. Pimavanserin did not elicit catalepsy at doses up to 10 mg/kg achieving a maximum CV of 10.5±2.4 sec, a value that was not significantly different from that obtained in vehicle treated controls. In contrast, both haloperidol and risperidone produced dose-dependent and marked increases in CVs yielding $CD_{50}$ values of 0.27 mg/kg (0.19-0.39; 95% CI) and 1.1 mg/kg (0.79-1.62; 95% CI), respectively. Pimavanserin, at all doses tested, resulted in a dose-dependent and significant rightward displacement of the risperidone dose response curve for catalepsy. The calculated $CD_{50}$ values for risperidone in the presence of 1 (filled circles), 3 (open squares) or 10 mg/kg (filed squares) pimavanserin were 2.0 mg/kg (1.3-3.0; 95% CI), 4.4 mg/kg (2.6-7.5; 95% CI) and 5.1 mg/kg (3.2-8.3; 95% CI), respectively, indicating a reduction of catalepsy.

Discussion:

Antagonism of $D_2$ receptors produces robust prolactinemia both experimentally and clinically. Similarly, risperidone, an atypical APD, has also been shown to elicit prolactinemia as severe as haloperidol in humans. In the present investigation, it was demonstrated that while both haloperidol and risperidone produced robust increases in serum prolactin, pimavanserin alone did not elevate, and indeed slightly reduced, serum prolactin levels. Importantly, pimavanserin did not potentiate, but rather attenuated the hyperprolactinemia produced by these APDs. Despite the anatomical evidence supporting expression of $5\text{-}HT_2$ receptors in the pituitary gland, the preponderance of data suggests that the regulation of prolactin secretion mediated by $5\text{-}HT_{2A}$ receptors occurs at the level of the hypothalamus. Pituitary $D_2$ receptors, which lie outside of the blood brain barrier (BBB), exert tonic inhibition of prolactin secretion, while activation of $5\text{-}HT_{2A}$ receptors in the hypothalamus inhibits DA release resulting in prolactin elevation. Thus, pure $D_2$ antagonists elicit prolactinemia by direct actions in the pituitary, whereas, highly brain penetrating APDs, especially those which possess high $5\text{-}HT_{2A}/D_2$ affinity ratios (i.e., olanzapine and clozapine), do not elicit marked hyperprolactinemia because these drugs achieve sufficient $5\text{-}HT_{2A}$ receptor blockade in the hypothalamus to counteract the effects of $D_2$ receptor blockade in the pituitary. This is critical with respect to risperidone which has been shown to preferentially occupy $D_2$ receptors in the pituitary gland, as compared to the striatum, at doses up to 2.5 mg/kg in rats. If risperidone does indeed poorly cross the BBB then the profile of this drug is more consistent with a typical, rather than an atypical APD, as the direct effects at $D_2$ in the pituitary are not likely to be counteracted by $5\text{-}HT_{2A}$ receptor blockade inside the BBB. Consistent with this idea are the observations in the present study in which it was shown that risperidone elevates prolactin at doses equal to or below those required to attenuate head twitches produced by DOI. Furthermore, by combining pimavanserin with risperidone a sufficient level of $5\text{-}HT_{2A}$ receptor occupancy was reached inside the BBB to counteract risperidone-induced hyperprolactinemia. Taken together, these data indicate that risperidone is not likely to achieve maximum occupancy of $5\text{-}HT_{2A}$ receptors inside the BBB, in the absence of significant $D_2$ receptor antagonism, in rats or in humans. These finding have significant clinical relevance, as hyperprolactinemia is correlated with numerous complications such as sexual dysfunction, which is a prominent cause of noncompliance, particularly in men, with these medications.

Finally, this investigation demonstrated that while both haloperidol and risperidone produced dose-dependent catalepsy, pimavanserin alone did not elicit detectable catalepsy at doses as high as 10 mg/kg, or 50-fold higher than the $ID_{50}$ in a DOI head twitch assay, consistent with its lack of affinity for $D_2$ receptors. It was demonstrated that although pimavanserin potentiated the efficacy of haloperidol and risperidone, pimavanserin clearly did not potentiate the catalepsy produced by either drug. Instead, a small but significant reduction of haloperidol-induced catalepsy at a dose of pimavanserin was observed that would be expected for supramaximal $5\text{-}HT_{2A}$ receptor occupancy (i.e., 10 mg/kg). Pimavanserin demonstrates approximately 50-fold selectivity for $5\text{-}HT_{2A}$ over $5\text{-}HT_{2C}$. This result suggests that the attenuation of catalepsy by pimavanserin may be driven by its weaker $5\text{-}HT_{2C}$ receptor interactions. Based on the in vivo data, the selectivity of pimavanserin for $5\text{-}HT_{2A}$ over $5\text{-}HT_{2C}$ receptors would be approximately 50-fold, which is in agreement with previously published in vitro data. Pimavanserin also produced a significant attenuation of risperidone-induced catalepsy, however, at doses as low as 1 mg/kg. The apparent shift in potency shown by pimavanserin against risperidone-induced catalepsy is likely a function of the excess of $5\text{-}HT_{2A}$ antagonist expected to be present at doses of risperidone that would presumably occupy >70% of striatal $D_2$ receptors. Therefore, in a system that is in far excess of maximal 5-$HT_{2A}$ receptor occupancy, as would be expected with these dose combinations, weaker 5-$HT_{2C}$ antagonist properties of pimavanserin, and perhaps risperidone, are more likely to manifest.

Example 6

Prolactin Levels during Co-administration of Pimavanserin with Risperidone

Figure 22:
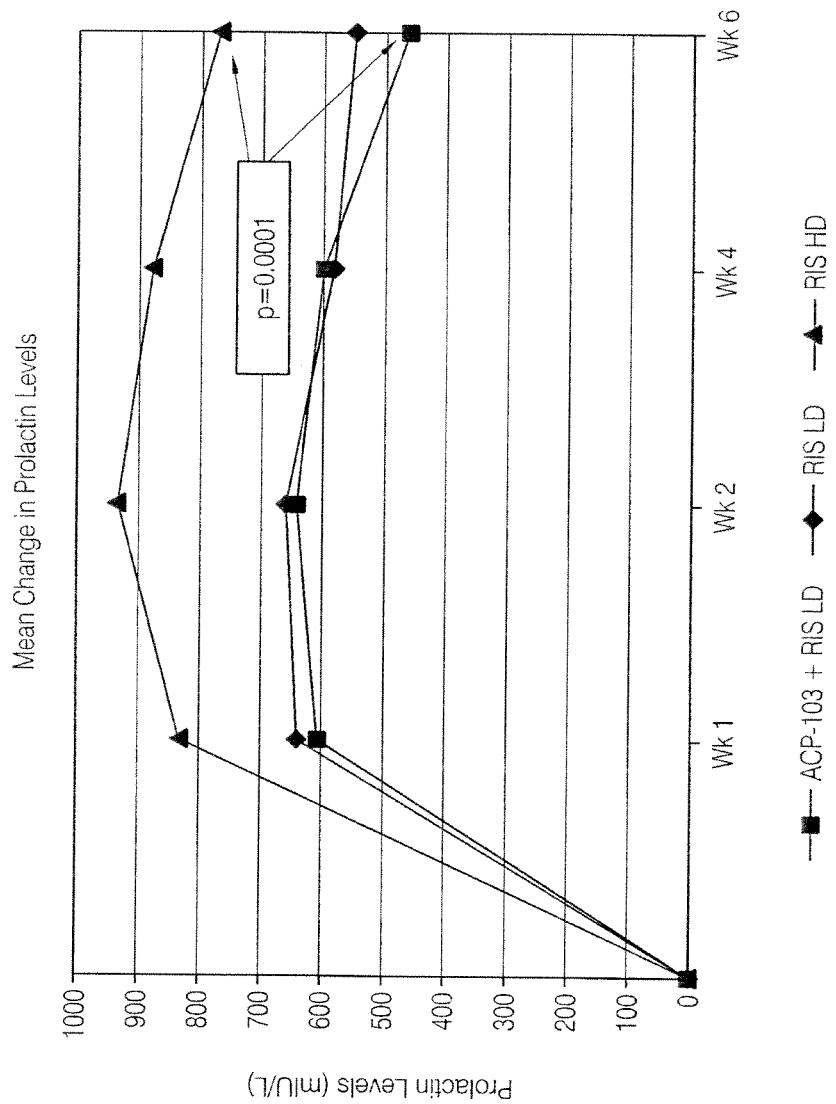
FIG. 22 is a graph depicting mean changes in prolactin levels upon administration of risperidone alone and in combination with pimavanserin.

Prolactin levels were measured during a Phase II schizophrenia co-therapy trial using pimavanserin in combination with risperidone and compared to administration of risperidone alone. As depicted in the FIG. 22 graph, patients in the co-therapy arm with pimavanserin plus risperidone (2 mg) had significantly lower prolactin levels after 42-days of treatment as compared to patients in the risperidone (6 mg) plus placebo arm (p=0.0001).

Example 7

Simulation of Pimavanserin and Risperidone Steady State Plasma Concentrations and 5-HT2A and D2 Receptor Occupancy following Co-administration Plasma Concentration-time Profile Following Oral Administration of 20 mg of Pimavanserin Once Daily Initial parameters for the simulation were obtained by fitting mean plasma concentration-time data to a 1-compartment model (first order input, no lag time and first order elimination). Mean multiple-dose plasma concentration-time data following the 14$^{th}$ oral dose of 50 mg of pimavanserin were applied. Based on the model, the pharmacokinetic parameters shown in Table 4 were estimated.

TABLE 4

Pharmacokinetic parameters obtained by fitting pimavanserin mean plasma concentration-time data (50 mg) to 1-compartment model.

| Pharmacokinetic parameter | Estimate |
| --- | --- |
| Absorption rate constant (k01) (1/hr) | 0.9197 |
| Elimination rate constant (k10) (1/hr) | 0.0121 |
| CL/F (L/hr) | 6.4 |
| Tmax (hr) | 4.77 |
| Cmax (ng/mL) | 89.27 |
| AUC (0-24)$_{ss}$ (hr*ng/mL) | 1893.2 |

The pharmacokinetic parameters provided in Table 4 agreed well with previous reported pharmacokinetic parameters obtained following multiple oral doses of pimavanserin. One exception is the oral clearance for which the estimated parameter is somewhat lower compared to the previous reported value (25.2 L/hr).

Figure 23:
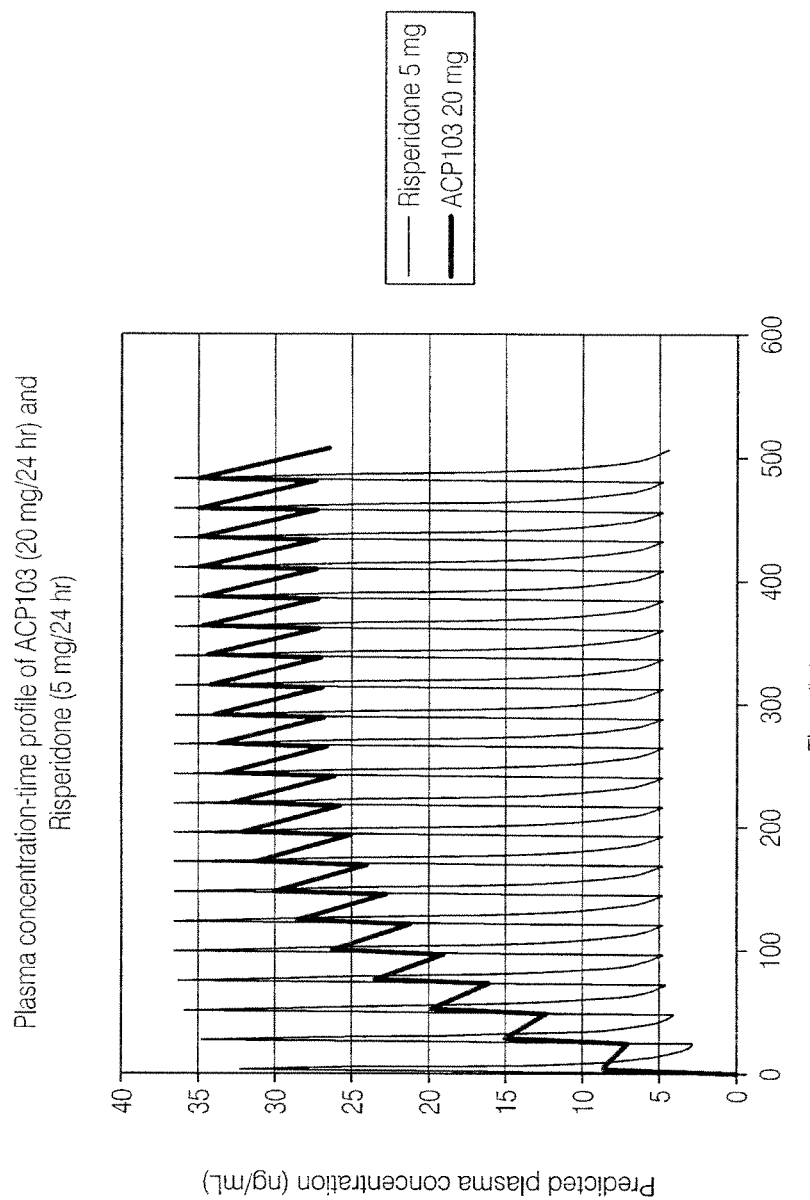
FIG. 23 is a graph depicting plasma concentration of risperidone and pimavanserin upon daily individual administration.

The plasma concentration-time profile of pimavanserin following oral administration of 20 mg of pimavanserin once daily was simulated using the initial parameters provided in Table 5. The simulated profile for pimavanserin administered alone are shown in FIG. 23.

TABLE 5

Initial parameters used in simulation of plasma concentration-time profile of pimavanserin following oral administration of 20 mg of pimavanserin once daily.

| Parameter | Value |
| --- | --- |
| V/F (mL) | 2182727 |
| K01 (1/hr) | 0.9197 |
| CL/F (mL/hr) | 26411* |

*Calculated using D/AUC$_{(0-24)ss}$

Plasma Concentration-time Profile Following Oral Administration of 5 of Risperidone Once Daily Initial parameters for the simulation were obtained by fitting mean plasma concentration-time data to a 2-compartment model (first order input, micro-constants, no lag time and first order elimination). Mean plasma concentration-time data obtained following administration of a single oral dose of 4 mg of risperidone were applied. Based on the model, the pharmacokinetic parameters shown in Table 6 were estimated.

TABLE 6

Pharmacokinetic parameters obtained by fitting risperidone mean plasma concentration-time data to a 2-compartment model

| Pharmacokinetic parameter | Estimate |
| --- | --- |
| Absorption rate constant (k01) (1/hr) | 0.4403 |
| Elimination rate constant (k10) (1/hr) | 0.2393 |
| Alpha (1/hr) | 0.4314 |
| Beta (1/hr) | 0.0349 |
| CL/F (L/hr) | 14408.8 |
| V2/F (mL) | 157245.7 |
| CLD2/F (mL/hr) | 9885.5 |
| Tmax (hr) | 2.4 |
| Cmax (ng/mL) | 25.8 |
| AUC (hr*ng/mL) | 277.6 |

The pharmacokinetic parameters provided in Table 6 agreed reasonably well with previous reported pharmacokinetic parameters for risperidone. However, the secondary parameters were poorly estimated by the model as indicated by the coefficient of variation of the parameters.

The plasma concentration-time profile of risperidone following oral administration of 5 mg of risperidone once daily was simulated using the initial parameters provided in Table 7. The simulated profile for risperidone administered alone are shown in FIG. 23.

TABLE 7

Initial parameters used in simulation of plasma concentration-time profile of risperidone following oral administration of 5 mg of risperidone once daily.

| Parameter | Value |
| --- | --- |
| V1/F (mL) | 60222 |
| K01 (1/hr) | 0.4403 |
| CL/F (mL/hr) | 14409 |
| V2/F (mL) | 157246 |
| CLD2/F (mL/hr) | 9886 |

Due to the shorter half-life of risperidone, 19.9 hr compared to 57.3 for pimavanserin, fluctuations between peak and trough plasma concentrations are seen to be higher for risperidone. Steady state concentrations of pimavanserin are reached following approximately 200 hr corresponding to 8 days. $C_{min,SS}$ and $C_{max,SS}$ for pimavanserin are approximately 27.2 and 34.5 ng/mL, respectively. The steady state maximum concentrations are reached approximately 4 hours post dosing.

Simulation of the Time Course of Serotonin 5-HT2A and Dopamine D2 Receptor Occupancy from Plasma Pharmacokinetics of Pimavanserin and Risperidone The receptor occupancy ($\Phi$, %) was calculated using equation 1, $\Phi=(C_R/C_R+Kd)*100$, where $C_R$ is the concentration of unbound drug around the receptor (nM) and Kd is the dissociation constant (nM).

$C_R$ is assumed to equal the unbound drug concentration in plasma implying that equilibrium between plasma and brain is fast and no active transport of the drug takes place during distribution to the brain. $C_R$ may then be calculated using equation 2. $C_R=f_u*C_{pl}(t)$, where $f_u$ is the free fraction of drug in plasma and $C_{pl}(t)$ is the plasma concentration at time t.

The 5HT2A and D2 receptor occupancies of pimavanserin and risperidone were estimated using the parameters in Table 7 and the $C_{pl}(t)$ obtained above.

TABLE 7

Unbound fraction in plasma and Kd of pimavanserin and risperidone

|  | $f_u$ | Kd (nM) 5HT2A | D2 |
| --- | --- | --- | --- |
| Pimavanserin | 0.05 | 0.4 |  |
| Risperidone | 0.1 | 0.2 | 0.3 |

Figure 24:
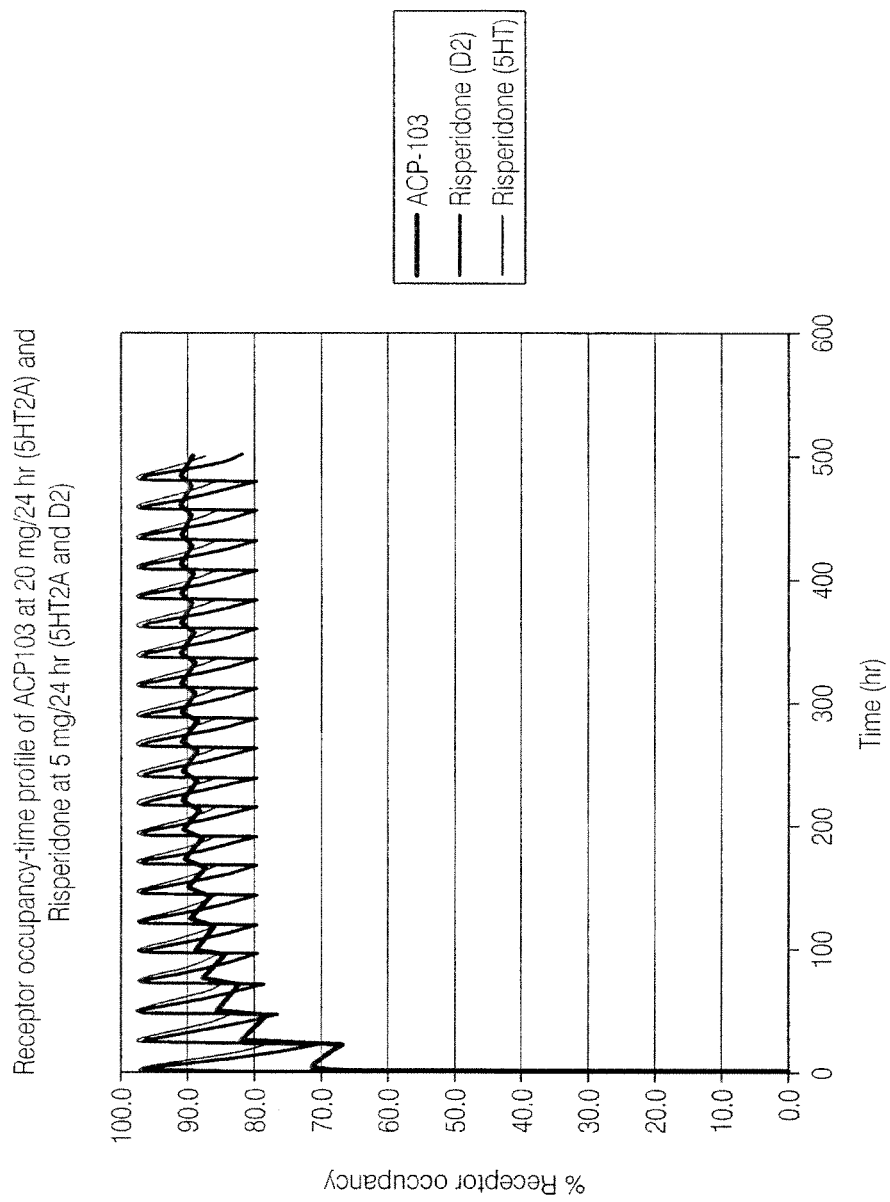
FIG. 24 is a graph depicting 5-HT2A and D2 receptor occupancy upon daily individual administration of risperidone and pimavanserin.

The receptor occupancy-time profile of pimavanserin (20 mg/24 hr) and risperidone (5 mg/24 hr) when administered separately is shown in FIG. 24. Risperidone, which acts at both D2 and 5HT receptors, achieved high occupancy at both receptors. Pimavanserin, which has a longer half life than risperidone, showed less variability in 5HT receptor occupancy.

Following the first oral dose of 20 mg of pimavanserin 71% 5HT2A receptor occupancy is achieved 5 hr post dosing (tmax). The corresponding plasma concentration of pimavanserin (Cmax) is 8.6 ng/mL. Steady state 5HT2A receptor occupancies for pimavanserin vary between 88 and 91%.

The calculated occupancy of 5HT2A and D2 receptors 2.4 hours after the first oral dose of 5 mg of risperidone is 98% and 96%, respectively. The corresponding plasma concentration of risperidone is 32.3 ng/mL. The steady state D2 receptor occupancy of risperidone ranges between 80% and 97%. Occupancy of the 5HT receptor in steady state is between 86% and 98%. The corresponding minimum and maximum steady state plasma concentrations of risperidone are 4.9 ng/mL and 36.6 ng/mL.

Figure 25:
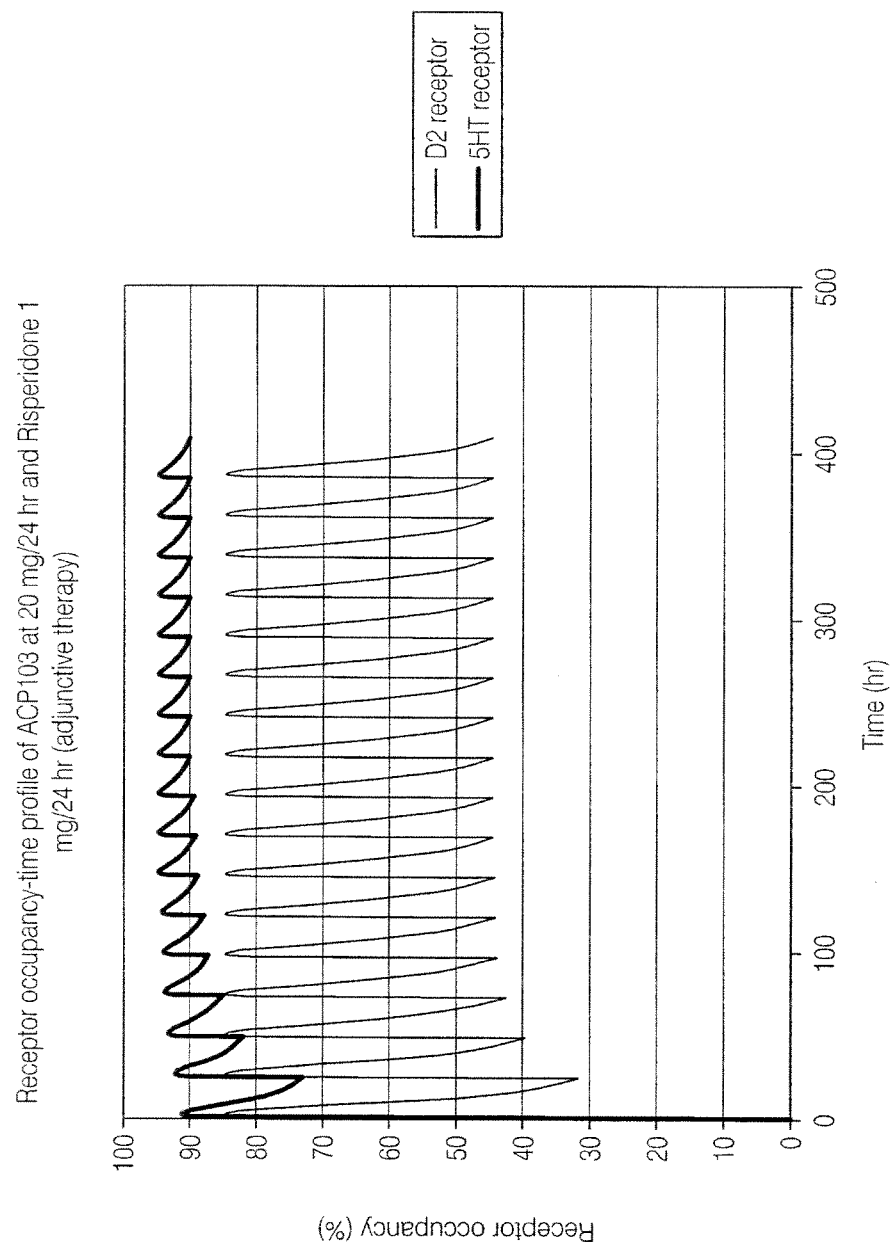
FIG. 25 is a graph depicting 5-HT2A and D2 receptor occupancy upon daily administration of pimavanserin in combination with 1 mg of risperidone.

The receptor occupancy-time profile of D2 and 5HT receptors following combined therapy with pimavanserin and risperidone is shown in FIG. 25. The pimavanserin dose was maintained at 20 mg once daily as in FIG. 24, whereas the daily dose of risperidone has been reduced to 1 mg once daily. The results indicate that D2 receptor occupancy significantly decreases as compared to the higher dose of risperidone administered alone (see FIG. 24) while the 5HT receptor occupancy is maintained at high level. These results support that the combination can lead to a lower incidence of D2 related side effects without affecting 5HT associated efficacy.

The D2 receptor occupancy was calculated using equation 1. The 5HT receptor occupancy was calculated using equation 3: $\Phi=(C_{R1}/(C_{R1}+Kd_{5HT,1}(1+C_{R2}/Kd_{5HT,2}))+(C_{R2}/(C_{R2}+Kd_{5HT,2}(1+C_{R1}/Kd_{5HT,1})))*100$, where $C_{R1}$, $C_{R2}$, $Kd_{5HT,1}$, $Kd_{5HT,2}$ is the unbound concentration of pimavanserin, unbound concentration of risperidone, dissociation constant of pimavanserin for 5HT2A receptor and dissociation constant of risperidone for 5HT2A, respectively.

Figure 26A:
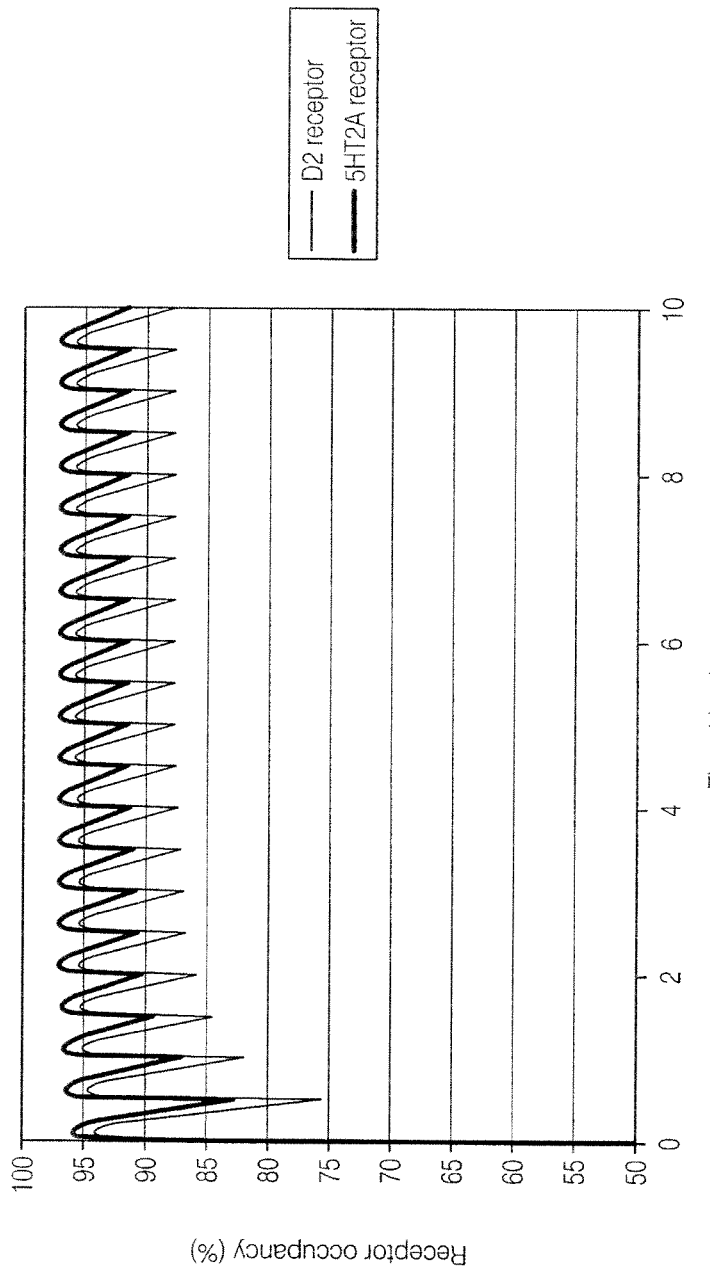
FIGS. 26A and 26B are graphs depicting 5-HT2A and D2 receptor occupancy upon administration of 3 mg risperidone twice daily alone (FIG. 26A) and in combination (FIG. 26B) with pimavanserin excluding the contribution from paliperidone.
Figure 26B:
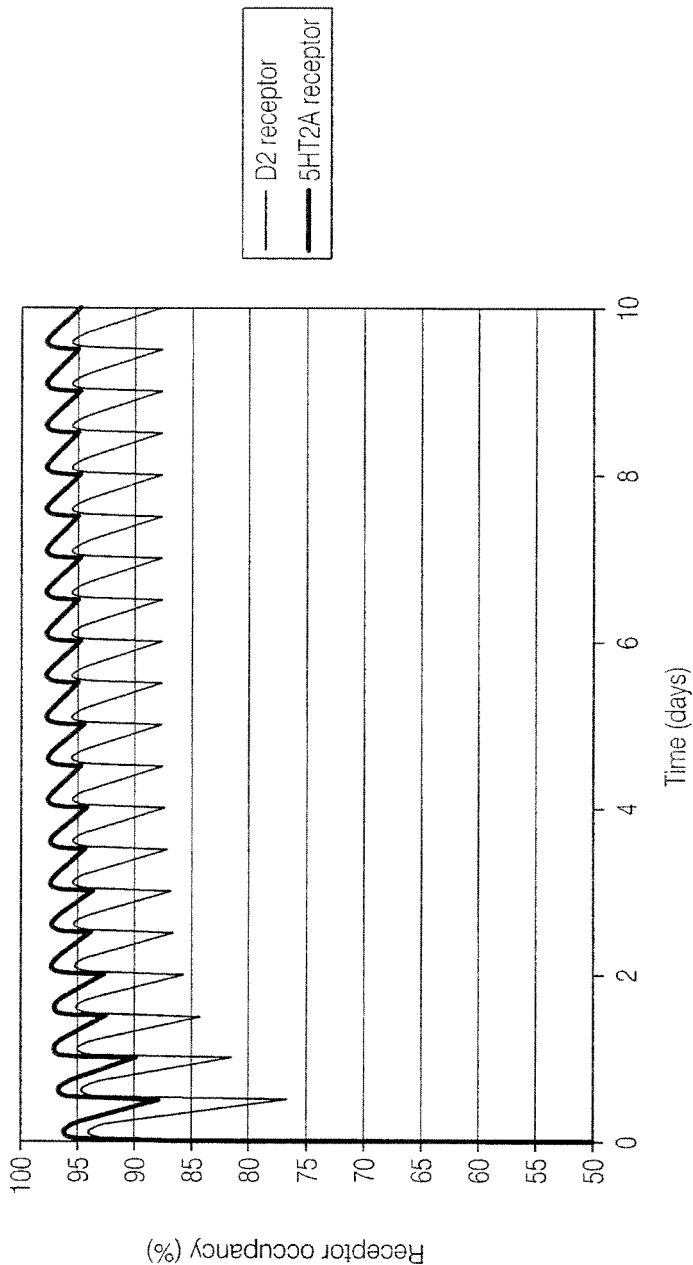

Several other doses of risperidone were also evaluated. The D2 and 5HT receptor occupancy-time profiles following therapy with 3 mg twice daily of risperidone alone is shown in FIG. 26A. The D2 and 5HT receptor occupancy-time profiles following combined therapy with pimavanserin and risperidone is shown in FIG. 26B. The pimavanserin dose was maintained at 20 mg daily, and the risperidone dose was maintained at 3 mg twice daily. The contribution from paliperidone to the receptor profiles was not taken into account. FIGS. 26A and 26B illustrate that receptor occupancy of 5HT was enhanced with combined pimavanserin and risperidone therapy versus risperidone therapy alone when dosing at 3 mg twice daily. Notably, due to the long action of the low half-life pimavanserin, the variation in 5HT receptor occupancy decreased in the combination. The receptor occupancy of D2 remained substantially unchanged.

Figure 27A:
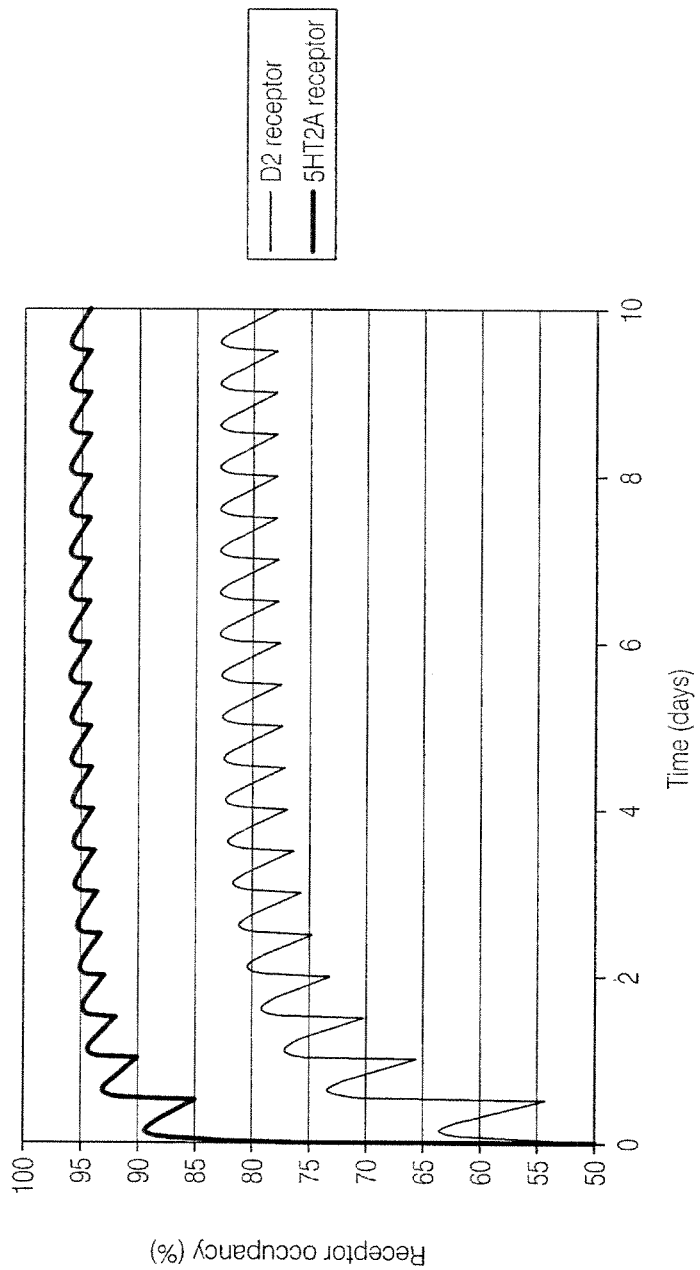
FIGS. 27A and 27B are graphs depicting 5-HT2A and D2 receptor occupancy for paliperidone upon administration of 3 mg risperidone twice daily alone (FIG. 27A) and in combination (FIG. 27B) with pimavanserin.
Figure 27B:
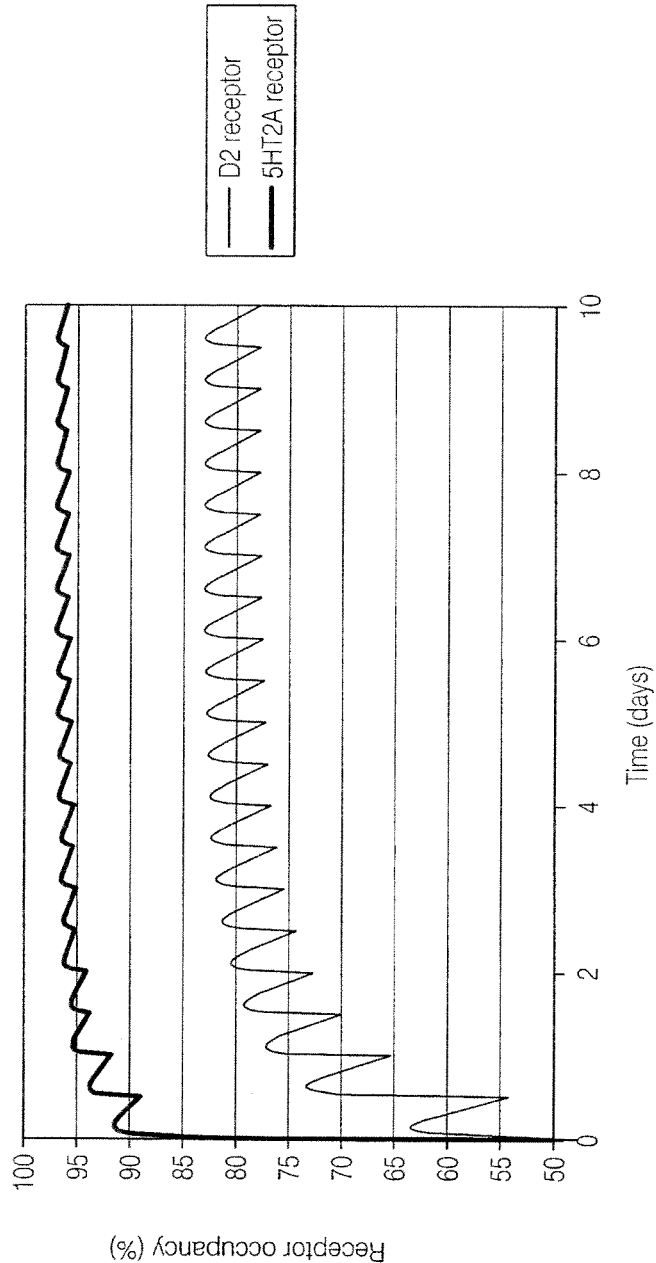

The D2 and 5HT receptor occupancy-time profiles for paliperidone (a metabolite of risperidone) following therapy with risperidone alone at 3 mg twice daily is shown in FIG. 27A. The risperidone dose was maintained at 3 mg twice daily. The D2 and 5HT receptor occupancy-time profiles for paliperidone following combined therapy with pimavanserin and risperidone is shown in FIG. 27B. The pimavanserin dose was maintained at 20 mg daily and the risperidone dose was maintained at 3 mg twice daily. The contribution from risperidone to the receptor profiles was not taken into account. FIGS. 27A and 27B further illustrate that receptor occupancy of 5HT was slightly enhanced with combined pimavanserin and risperidone therapy versus risperidone therapy alone when dosing at 3 mg twice daily. The receptor occupancy of D2 remained substantially unchanged.

Figure 28A:
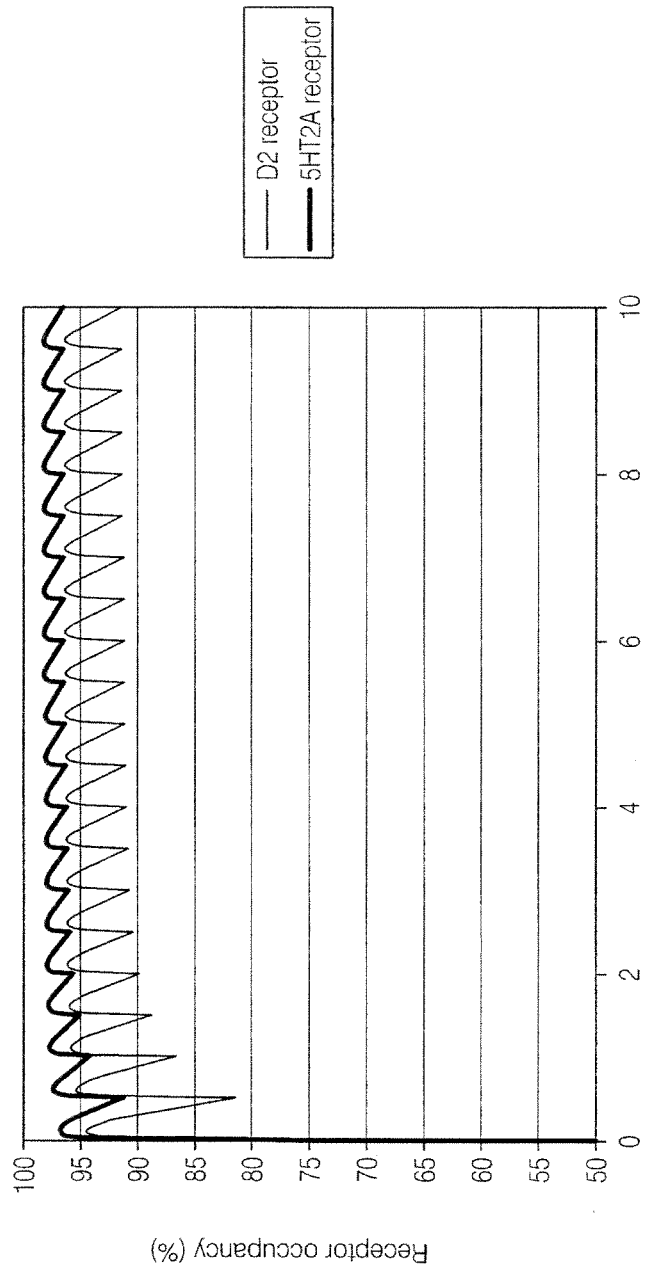
FIGS. 28A and 28B are graphs depicting 5-HT2A and D2 receptor occupancy upon administration of 3 mg risperidone twice daily alone (FIG. 28A) and in combination (FIG. 28B) with pimavanserin including the contribution from paliperidone.
Figure 28B:
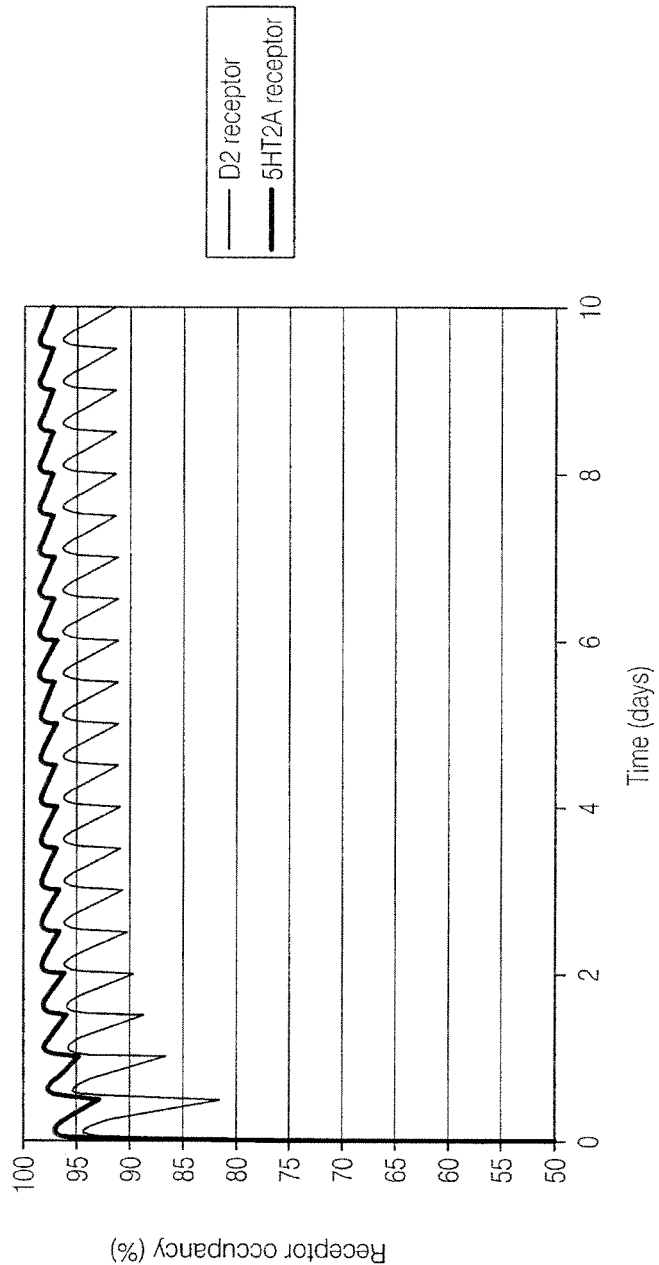

The D2 and 5HT receptor occupancy-time profiles following therapy with risperidone with 3 mg twice daily taking into consideration both risperidone and paliperidone is shown in FIG. 28A. The D2 and 5HT receptor occupancy-time profiles following combined therapy with pimavanserin and risperidone is shown in FIG. 28B. The pimavanserin dose was maintained at 20 mg daily and the risperidone dose was maintained at 3 mg twice daily. FIGS. 28A and 28B further illustrate that receptor occupancy of 5HT was slightly enhanced with combined pimavanserin and risperidone therapy versus risperidone therapy alone when dosing at 3 mg twice daily. The receptor occupancy of D2 remained substantially unchanged.

Figure 29A:
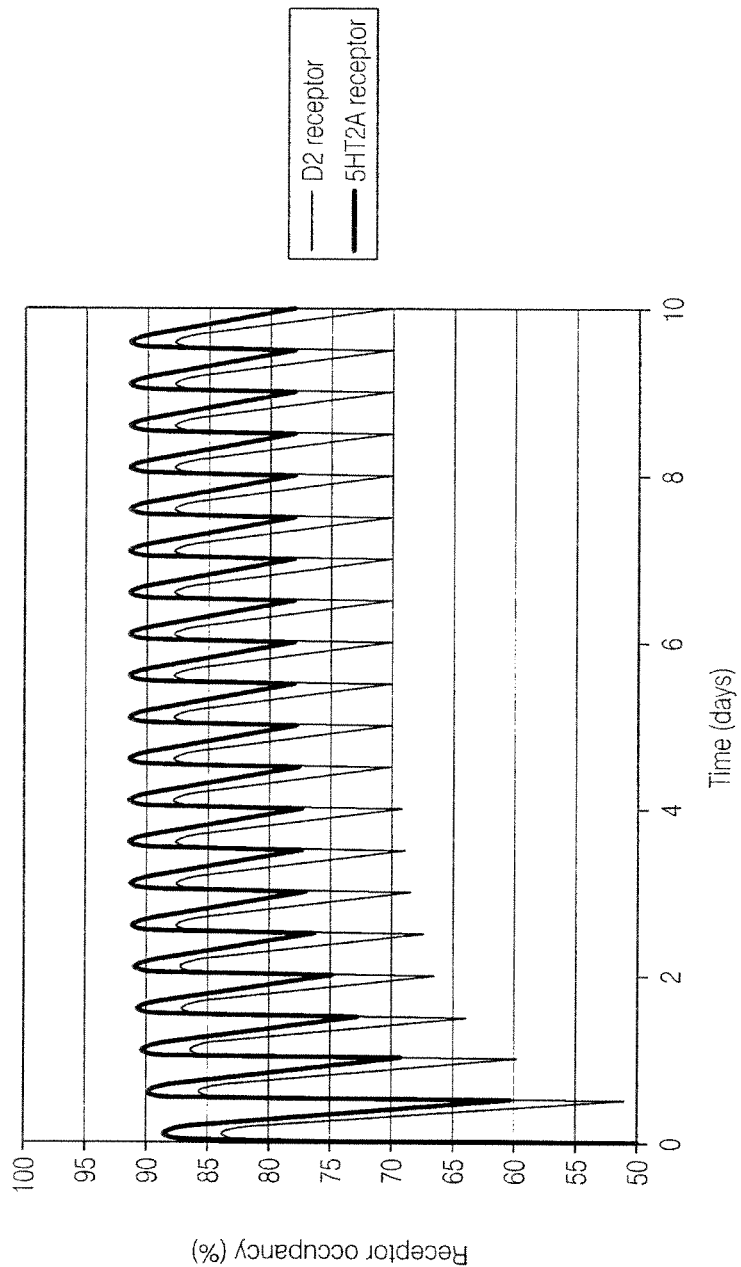
FIGS. 29A and 29B are graphs depicting 5-HT2A and D2 receptor occupancy upon administration of 1 mg risperidone twice daily alone (FIG. 29A) and in combination (FIG. 29B) with pimavanserin excluding the contribution from paliperidone.
Figure 29B:
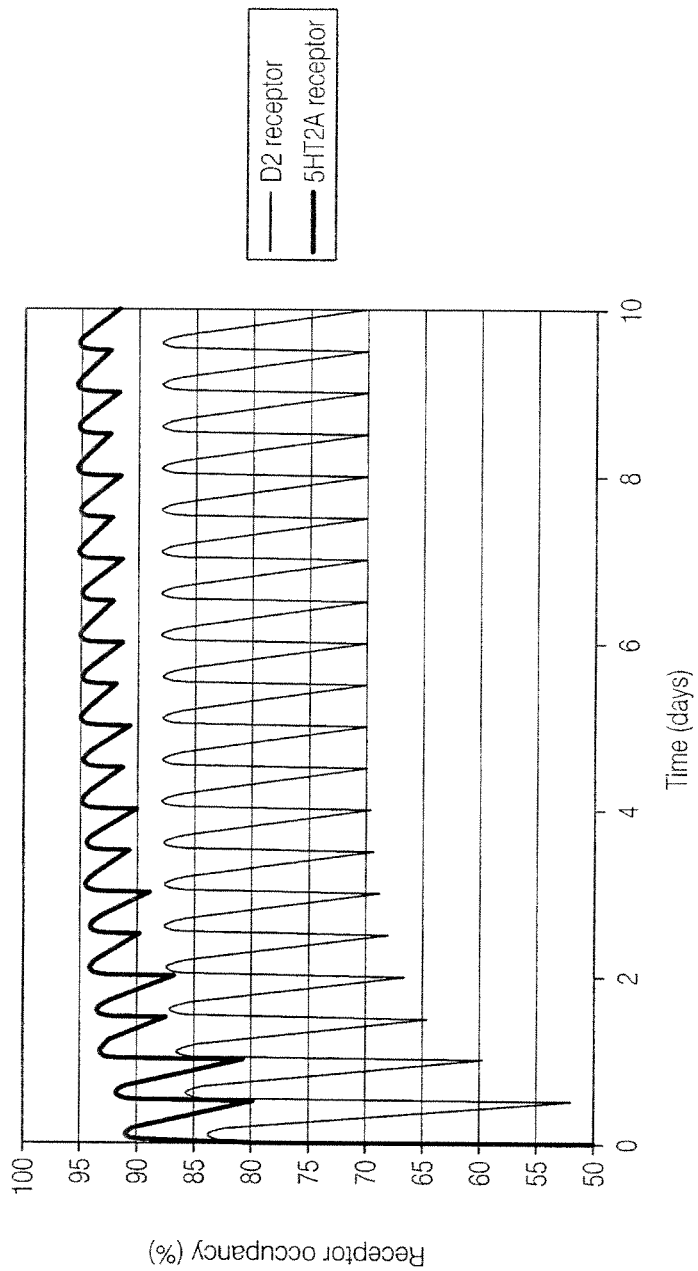

The D2 and 5HT receptor occupancy-time profiles following therapy with 1 mg twice daily of risperidone alone is shown in FIG. 29A. The D2 and 5HT receptor occupancy-time profiles following combined therapy with pimavanserin and risperidone is shown in FIG. 29B. The pimavanserin dose was maintained at 20 mg daily and the risperidone dose was maintained at 1 mg twice daily. For FIGS. 29A and 29B, the contribution from paliperidone to the receptor profiles was not taken into account. FIGS. 29A and 29B illustrate that receptor occupancy of 5HT was significantly enhanced with combined pimavanserin and risperidone therapy versus risperidone therapy alone at 1 mg twice daily dosing. The variation in 5HT receptor occupancy decreased substantially in the combination, demonstrating the beneficial effect of combining the long acting pimavanserin with the short acting risperidone. The receptor occupancy of D2 remained substantially unchanged. Comparison with FIG. 26B (illustrating a 3 mg twice daily dose of risperidone) illustrates a more significant enhancement in 5HT receptor occupancy with a decreased D2 receptor occupancy.

Figure 30A:
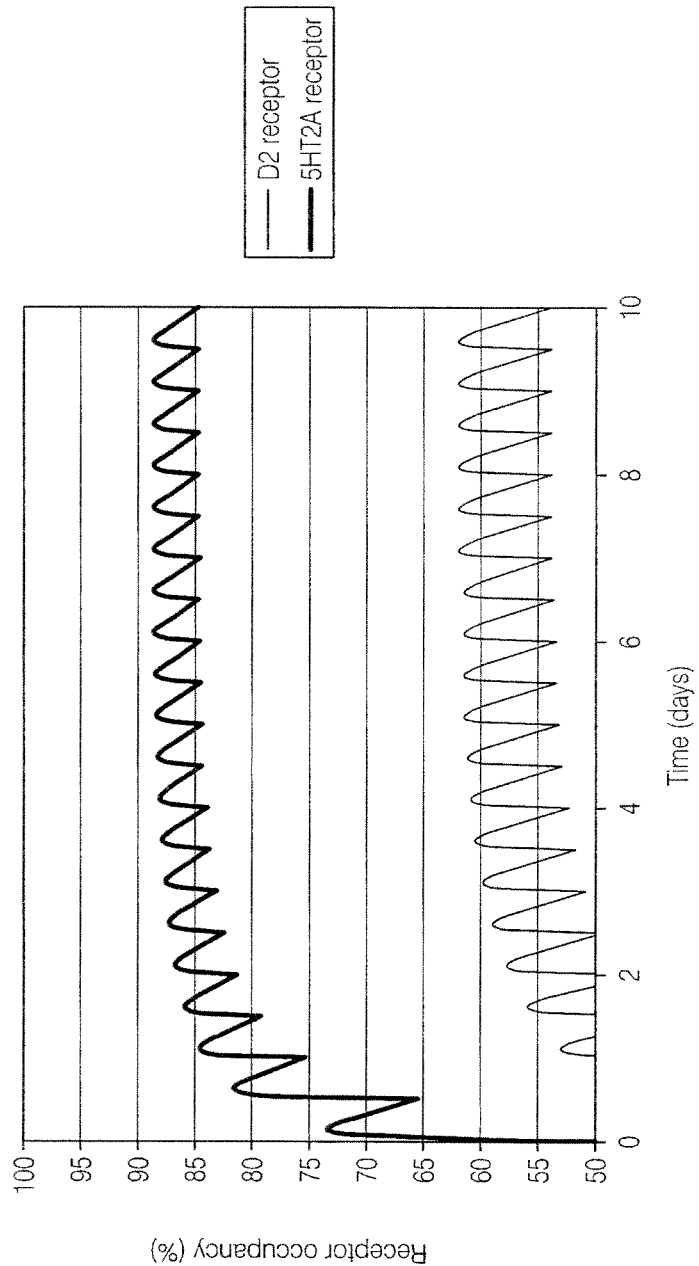
FIGS. 30A and 30B are graphs depicting 5-HT2A and D2 receptor occupancy upon administration of 1 mg risperidone twice daily alone (FIG. 30A) and in combination (FIG. 30B) with pimavanserin including the contribution from paliperidone.
Figure 30B:
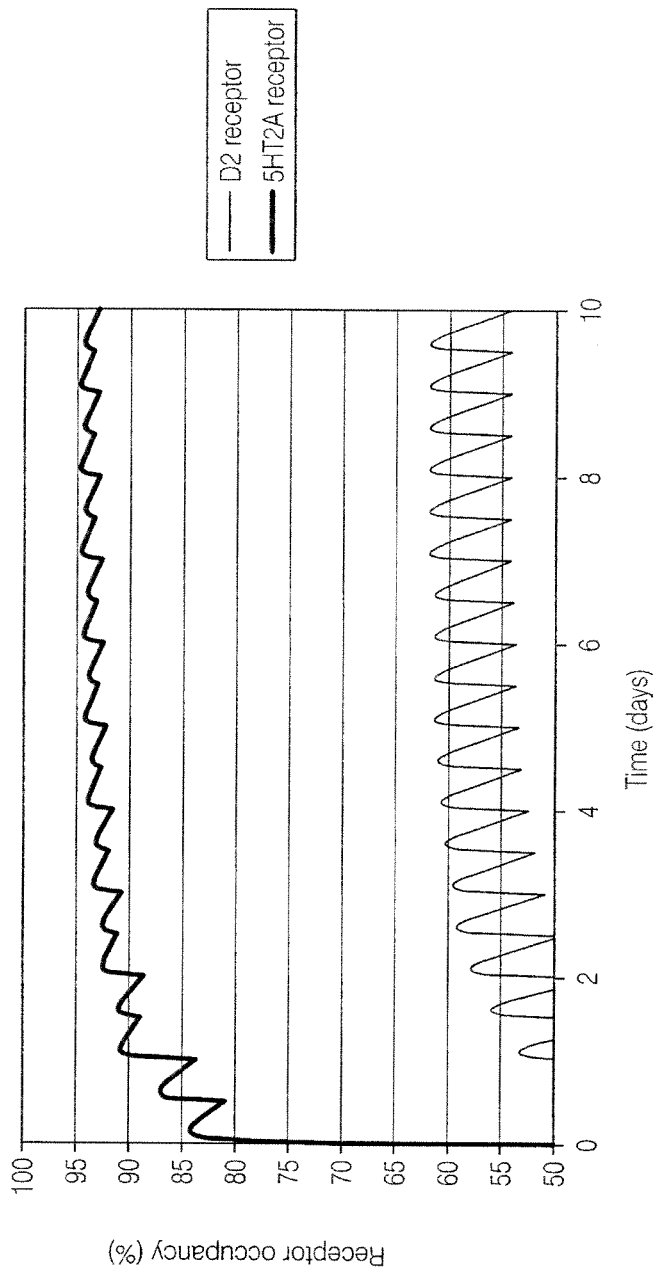

The D2 and 5HT receptor occupancy-time profiles for paliperidone following therapy with 1 mg twice daily risperidone alone is shown in FIG. 30A. The D2 and 5HT receptor occupancy-time profiles for paliperidone following combined therapy with pimavanserin and risperidone is shown in FIG. 30B. The pimavanserin dose was maintained at 20 mg daily and the risperidone dose was maintained at 1 mg twice daily. For FIGS. 30A and 30B, the contribution from risperdone to the receptor profiles was not taken into account. FIGS. 30A and 30B illustrate that receptor occupancy of 5HT was significantly enhanced with combined pimavanserin and risperidone therapy versus risperidone therapy alone at 1 mg twice daily dosing. A decrease in 5HT receptor occupancy variation was also observed in the combination. The receptor occupancy of D2 remains substantially unchanged. Comparison with FIG. 27B (illustrating a 3 mg twice daily dose of risperidone) illustrates a more significant enhancement in 5HT receptor occupancy with a decreased D2 receptor occupancy.

Figure 31A:
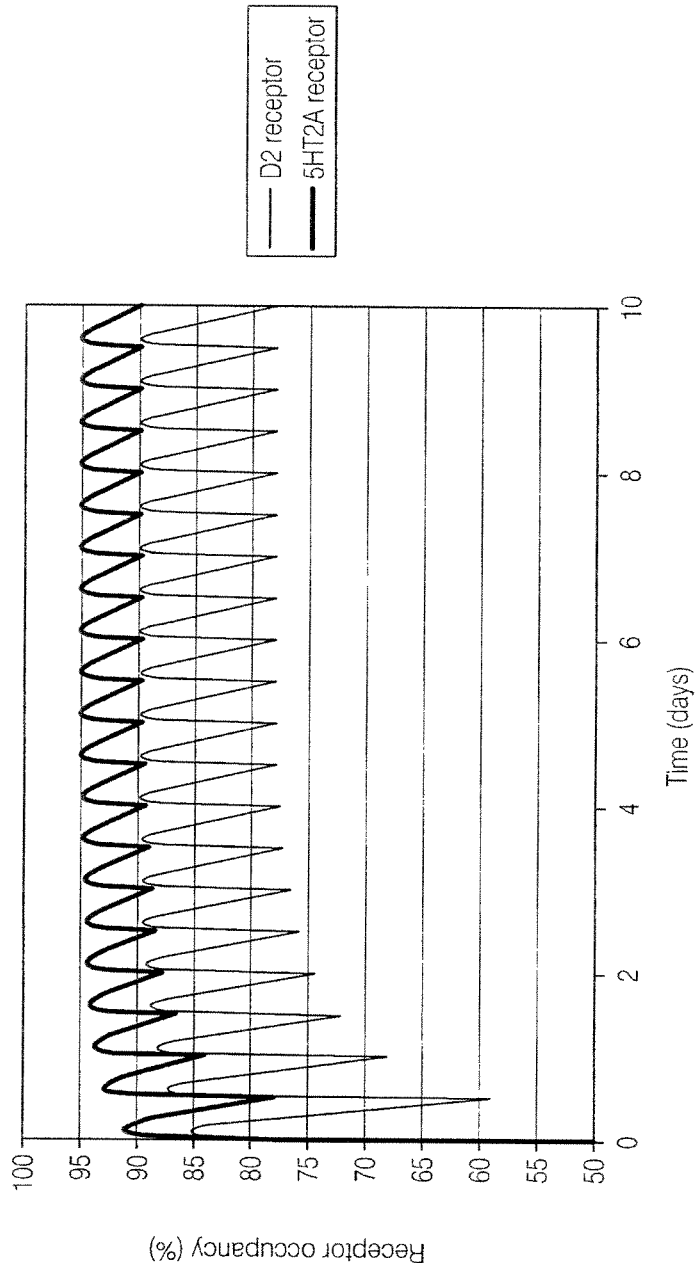

The D2 and 5HT receptor occupancy-time profiles following therapy with 1 mg twice daily taking both risperidone and paliperidone into account is shown in FIG. 31A. The D2 and 5HT receptor occupancy-time profiles following, combined therapy with pimavanserin and risperidone is shown in FIG. 31B. The pimavanserin dose was maintained at 20 mg daily and the risperidone dose was maintained at 1 mg twice daily. FIGS. 31A and 31B illustrate that receptor occupancy of 5HT was significantly enhanced with combined pimavanserin and risperidone therapy versus risperidone therapy alone at 1 mg twice daily dosing. A decrease in 5HT receptor occupancy variation was also observed in the combination. The receptor occupancy of D2 remained substantially unchanged. Comparison with FIG. 28B (illustrating a 3 mg twice daily dose of risperidone) illustrates a more significant enhancement in 5HT receptor occupancy with a decreased D2 receptor occupancy.

Taken together, FIGS. 24-31B demonstrate that combinations of pimavanserin and low doses of risperidone can result in an enhancement of the receptor occupancy of the 5HT2A receptor compared with low dose risperidone therapy alone and achieve a lower D2 receptor occupancy due to the lower dose of risperidone. Thus, a combined therapy with pimavanserin and risperidone can increase the efficacy of anti-psychotic treatment without increasing side effects due to D2 receptor occupancy. Furthermore, the results demonstrate that combining the long acting drug pimavanserin with the short acting drug risperidone results in significantly less variability in 5-HT2A receptor occupancy, allowing the high levels of occupancy to be maintained between dosings.

Although the invention has been described with reference to embodiments and examples, it should be understood that numerous and various modifications can be made without departing from the spirit of the invention. Accordingly, the invention is limited only by the following claims.

What is claimed is:

1. A method for treating acute exacerbation of psychosis in a patient having psychosis, comprising co-administering a compound of formula (I):

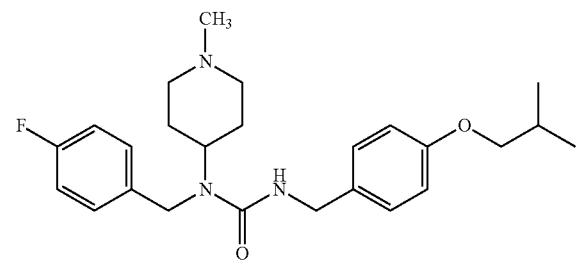 [SMILES: CC(C)COc1ccc(CNC(=O)N(Cc2ccc(F)cc2)C2CCN(C)CC2)cc1]

or a pharmaceutically acceptable salt thereof, and risperidone, wherein the dose of the compound of formula (I) is about 20 mg per day, and the dose of risperidone is less than about 6 mg per day.

2. The method of claim 1, wherein the dose of risperidone is about 2 mg per day.

3. The method of claim 1, wherein the psychosis is associated with schizophrenia.

4. The method of claim 1, wherein the psychosis is associated with Parkinson's disease.

5. The method of claim 1, wherein the psychosis is associated with Alzheimer's disease.

6. The method of claim 1, wherein the psychosis is associated with bipolar disease.

* * * * *